US008263366B2

(12) United States Patent
Chiu et al.

(10) Patent No.: US 8,263,366 B2
(45) Date of Patent: Sep. 11, 2012

(54) METHOD FOR TRACING GRAM-NEGATIVE BACTERIA INSIDE ANIMAL MODEL USING STABLE AND BIOLUMINESCENCE-BASED EXPRESSION SYSTEM THEREFOR

(75) Inventors: Cheng-Hsun Chiu, Taoyuan County (TW); Chyi-Liang Chen, Taoyuan County (TW); Yao-Kuang Huang, Taoyuan County (TW)

(73) Assignee: Chang Gung Medical Foundation, Linkou Branch, Taoyuan County (TW)

( * ) Notice: Subject to any disclaimer, the term of this patent is extended or adjusted under 35 U.S.C. 154(b) by 0 days.

(21) Appl. No.: 13/109,807

(22) Filed: May 17, 2011

(65) Prior Publication Data

US 2012/0083031 A1 Apr. 5, 2012

Related U.S. Application Data

(62) Division of application No. 12/895,849, filed on Oct. 1, 2010.

(51) Int. Cl.
*C12N 15/64* (2006.01)
*C12N 15/74* (2006.01)

(52) U.S. Cl. ........................................ 435/91.4; 435/476

(58) Field of Classification Search ........................ None
See application file for complete search history.

(56) References Cited

U.S. PATENT DOCUMENTS

2002/0137215 A1 * 9/2002 Francis et al. ................ 435/473

OTHER PUBLICATIONS

Chen et al., Functional andmolecular characterization of pSE34 encoding a type IV secretion system inSalmonella enterica serotype Enteritidis phage type 34, FEMS Immunol Med Microbiol 57 (2009) 274-283.*

Francis et al., Monitoring Bioluminescent Staphylococcus aureus Infections in Living Mice Using a Novel IuxABCDE Construct, Infection and Immunity, Jun. 2000, p. 3594-3600.*

Billard et al., Bioluminescence-Based Assays for Detection and Characterization of Bacteria and Chemicals in Clinical Laboratories, Clinical Biochemistry, vol. 31, No. 1, 1-14, 1998.*

Caliper publication, “Bioware Plasmid—pXen-5 (pAUL-A Tn4001 luxABCDE KmR, 18359bp) Overview Sheet,” Published by Caliper LifeSciences, Jan. 2008.*

Mees et al, pBluescript II: gene mapping vectors, Nucleic Acid Research V. 17, N. 22, 1989.*

* cited by examiner

*Primary Examiner* — Jim Ketter
*Assistant Examiner* — Reza Ghafoorian

(57) ABSTRACT

A method of creating a biotechnological product and an efficient and stable bio-luminescence vector which could be used for tracking Gram-negative bacteria when distributing inside animal body are provided. Through conjugation, this autoluminescence vector can be easily transmitted from bacteria to bacteria among Gram-negative bacteria, and may facilitate bacteria to be luminescence-labeled for subsequently analyzing the dynamic change of bio-luminescent bacteria within animal body in vivo. This system includes a lacZ promoter-driven luxABCDE, a high copy number of ColE1 replicon, and a high plasmid stability of the conjugative and broad host-ranged plasmid pSE34 from *Salmonella enterica* serovar *Enteritidis* Sal550. This resulting construct pSE-Lux1 can not only conjugatively transmit among bacteria with broad host range, but also stably maintain in bacteria to efficiently express the bio-luminescent luxABCDE without supplementing the subtract for luciferases and the antibiotics for plasmid selection.

1 Claim, 7 Drawing Sheets pBlueScript II KS
luxABCDE
pSE34
pSE-Lux1
46.3kb
Amp$^r$;Kan$^r$
pGEM3-Zf+

Plasmid stability tests of p3Zlux4 and pSE-Lux1

| CFU[@]/ml | p3Zlux4 in E. coli Top10 | | | pSE-Lux1 in S. enterica Typhimurium LBNP4417 | | |
|---|---|---|---|---|---|---|
| | LB broth | LB broth + Amp +Kan | Stability rate* | LB broth | LB broth + Amp +Kan | Stability rate |
| $10^2$ | ND[#] | 43 | $43 \times 10^2 / 488 \times 10^6 = 8.8 \times 10^{-4}\%$ | ND | ND | 1,550/ 2,030 = 76.3% |
| $10^3$ | ND | 4 | | ND | ND | |
| $10^4$ | ND | 0 | | ND | ND | |
| $10^5$ | ND | 0 | | ND | ND | |
| $10^6$ | 488 | 0 | | 2,030 | 1,550 | |

[@] Colony formation unit

* Stability test was determined after 79 generation.

[#] ND represents that the bacterial colonies were not detectable due to too much bacterial cells to count.

FIG. 5

SEQUENCE LISTING

```
<160> NUMBER OF SEQ ID NOS: 22

<210> SEQ ID NO 1
<211> LENGTH: 46313
<212> TYPE: DNA
<213> ORGANISM: ARTIFICIAL SEQUENCE
```

<220> FEATURE:
<223> OTHER INFORMATION: GRAM-NEGATIVE BACTERIA USING STABLE AND BIOLUMINESCENCE PLASMID

<400> SEQUENCE: 1

```
tgtcactgat ccaacgatta aaaaattact gaaagataag gataaagaca aaaaagatga     60
acatggcggt attggtacgc cagctacccg tgcagccatt ctggaaacgc tgaagaagag    120
aaactatatc acgctggaaa aagggaaact tattccgact gataccggat atgcgcttat    180
tgatgccctg ccaggtatag cggttaatcc tgatatgaca gcattatggt ctgaaaagca    240
gactgccatt gaaaatggcg acctgacggt tgaacagttt attaatgagc tgtacggtga    300
attgacaggc atgatttctg atgttgacct gggcaagatg aagattgaac ccgctgcgcc    360
agcagggcag tttcaacgcc tggactctcc ctgcccttcc tgtggtaaac atattgttat    420
caggccgaaa ggttatttct gtaccggatg tgaatttaaa atctggagtg agttttctgg    480
taagaaaatc acccaggcac aggccgaaaa actggttaaa tcagggaaaa ccgatttgat    540
taagggattt aaaaagaaaa gtggtggaac gtatgataca gttcttgtcc ttgaggataa    600
gaaaacaggg aagctgggtt ttccggcaag ggctaagaag tgaaaacaaa gcaggaatgg    660
ctttttcagt taagaaaatg tacatcaaga gatactcttg aaaaagttat tgagattaac    720
cgttacaagc tgcctttatc agaatcagag gcattttatt ctgccgcaga tcaccgccgt    780
gcagaactgg tgatgaataa actttatgat aaggttcctt ccggcgtatg gaagtacgtc    840
cattaaacaa gaggattaat tatgagcgaa ctgactaaag aagatgaata cggcattatc    900
agccggacta tgatgaatat tcgttcattg cgtgtgtttg cccgtgagat tgattttgag    960
cagttgctcg aaatgcagga aaagctcaac gttgttattg aagaacgtcg tgaagatgct   1020
gaacgtgaag cggctgaacg agcagagcgt gaacggaaac gtcaggaact gcttcagtta   1080
atcgccggag agggtttctc accggaagaa ctgcttggtc tgtccgaaga agcaccaaaa   1140
tcacgtaaaa aaacgttacc aaaagcgcca cccaagtatc aatttgaaga aaatggtgaa   1200
acgaaatact ggtctggtcg tggacgtgcg ccaaaaccga ttgatgaagc gttgaaagcc   1260
gggcgttctc tggaagattt tcgtatcaat aagagtttga acggagtaac agatgagcag   1320
taatatggca aggatatagt tttatatcat cattttgtta aggaagaaaa tccatgagta   1380
atacatccta caaacaaatt atccctgcga cagactggta tttccgtcac gataatgtct   1440
ccggtgtggc aggaaagtca acagtatacc aactggctgc atgggcgctt aaagaaaatg   1500
gtgaggtagt tggtctggtg acggttcgtg atgataatgg gcgtcctaaa ctggttactc   1560
ctcccccctgt ccctggtgat tatttgcata aagaacaact caccgatgat gaaaaagagt   1620
gggcgaagag acgctaaact atattcatat aaagcctctg ttctagagcg gccgccaccg   1680
cggtggagct ccaattcgcc ctatagtgag tcgtattacg cgcgctcact ggccgtcgtt   1740
ttacaacgtc gtgactggga aaaccctggc gttacccaac ttaatcgcct tgcagcacat   1800
ccccctttcg ccagctggcg taatagcgaa gaggcccgca ccgatcgccc ttcccaacag   1860
ttgcgcagcc tgaatggcga atggaaattg taagcgttaa tattttgtta aaattcgcgt   1920
taaatttttg ttaaatcagc tcatttttta accaataggc cgaaatcggc aaaatccctt   1980
ataaatcaaa agaatagacc gagatagggt tgagtgttgt tccagtttgg aacaagagtc   2040
cactattaaa gaacgtggac tccaacgtca aagggcgaaa aaccgtctat cagggcgatg   2100
gcccactacg tgaaccatca ccctaatcaa gtttttttggg gtcgaggtgc cgtaaagcac   2160
taaatcggaa ccctaaaggg agcccccgat ttagagcttg acggggaaag ccggcgaacg   2220
```

```
tggcgagaaa ggaagggaag aaagcgaaag gagcgggcgc tagggcgctg gcaagtgtag   2280
cggtcacgct gcgcgtaacc accacacccg ccgcgcttaa tgcgccgcta cagggcgcgt   2340
caggtggcac ttttcgggga aatgtgcgcg gaacccctat ttgtttattt ttctaaatac   2400
attcaaatat gtatccgctc atgagacaat aaccctgata aatgcttcaa taatattgaa   2460
aaaggaagag tatgagtatt caacatttcc gtgtcgccct tattcccttt tttgcggcat   2520
tttgccttcc tgtttttgct cacccagaaa cgctggtgaa agtaaaagat gctgaagatc   2580
agttgggtgc acgagtgggt tacatcgaac tggatctcaa cagcggtaag atccttgaga   2640
gttttcgccc cgaagaacgt tttccaatga tgagcacttt taaagttctg ctatgtggcg   2700
cggtattatc ccgtattgac gccgggcaag agcaactcgg tcgccgcata cactattctc   2760
agaatgactt ggttgagtac tcaccagtca cagaaaagca tcttacggat ggcatgacag   2820
taagagaatt atgcagtgct gccataacca tgagtgataa cactgcggcc aacttacttc   2880
tgacaacgat cggaggaccg aaggagctaa ccgctttttt gcacaacatg ggggatcatg   2940
taactcgcct tgatcgttgg gaaccggagc tgaatgaagc cataccaaac gacgagcgtg   3000
acaccacgat gcctgtagca atggcaacaa cgttgcgcaa actattaact ggcgaactac   3060
ttactctagc ttcccggcaa caattaatag actggatgga ggcggataaa gttgcaggac   3120
cacttctgcg ctcggccctt ccggctggct ggtttattgc tgataaatct ggagccggtg   3180
agcgtgggtc tcgcggtatc attgcagcac tggggccaga tggtaagccc tcccgtatcg   3240
tagttatcta cacgacgggg agtcaggcaa ctatggatga acgaaataga cagatcgctg   3300
agataggtgc ctcactgatt aagcattggt aactgtcaga ccaagtttac tcatatatac   3360
tttagattga tttaaaactt catttttaat ttaaaaggat ctaggtgaag atcctttttg   3420
ataatctcat gaccaaaatc ccttaacgtg agttttcgtt ccactgagcg tcagaccccg   3480
tagaaaagat caaaggatct tcttgagatc cttttttct gcgcgtaatc tgctgcttgc   3540
aaacaaaaaa accaccgcta ccagcggtgg tttgtttgcc ggatcaagag ctaccaactc   3600
tttttccgaa ggtaactggc ttcagcagag cgcagatacc aaatactgtc cttctagtgt   3660
agccgtagtt aggccaccac ttcaagaact ctgtagcacc gcctacatac ctcgctctgc   3720
taatcctgtt accagtggct gctgccagtg gcgataagtc gtgtcttacc gggttggact   3780
caagacgata gttaccggat aaggcgcagc ggtcgggctg aacggggggt tcgtgcacac   3840
agcccagctt ggagcgaacg acctacaccg aactgagata cctacagcgt gagctatgag   3900
aaagcgccac gcttcccgaa gggagaaagg cggacaggta tccggtaagc ggcagggtcg   3960
gaacaggaga gcgcacgagg gagcttccag ggggaaacgc ctggtatctt tatagtcctg   4020
tcgggtttcg ccacctctga cttgagcgtc gatttttgtg atgctcgtca ggggggcgga   4080
gcctatggaa aaacgccagc aacgcggcct ttttacggtt cctggccttt tgctggcctt   4140
ttgctcacat gttctttcct gcgttatccc ctgattctgt ggataaccgt attaccgcct   4200
ttgagtgagc tgataccgct cgccgcagcc gaacgaccga gcgcagcgag tcagtgagcg   4260
aggaagcgga agagcgccca atacgcaaac cgcctctccc cgcgcgttgg ccgattcatt   4320
aatgcagctg gcacgacagg tttcccgact ggaaagcggg cagtgagcgc aacgcaatta   4380
atgtgagtta gctcactcat taggcacccc aggctttaca ctttatgctt ccggctcgta   4440
tgttgtgtgg aattgtgagc ggataacaat ttcacacagg aaacagctat gaccatgatt   4500
acgccaagcg cgcaattaac cctcactaaa gggaacaaaa gctgggtacc gggccccccc   4560
tcgacaagct caagggattc aagtcgccaa agaaaaaggt atatataaag ggagacctgt   4620
```

-continued

```
tctgtattct cccaatgcta aagacccaca aaagcgttta gtttattacc gagttgttga   4680
attacttgaa cagggtaaat ctataagtac tatagctaaa gaagttggta ttacacgtca   4740
aactatatat agaataaaaa atagtaaata aaataacata gacaataatc tatatagatg   4800
ttaatctatt taacatctag gaggtttatt catgtcttat aaagaactat caacaatatt   4860
aaaaatttta tcagattcaa gtaggttaga aatattagat ttactttctt gtggtgagct   4920
atgcgcttgt gacttattag aacactttca attctcacaa cctacactaa gtcatcatat   4980
gaagtcatta gtagataatg aattagttac aacacgaaaa gacggcaata aacattggta   5040
tcaacttaat catgctattt tagatgatat tatccaaaac ttgaacatca ttaatacatc   5100
taatcaaaga tgtgtatgta aaaatgtgaa atcaggtgac tgttgatgac tattttagca   5160
attgtaattt ttcttttaac tttaaccttt gtgatttggc aaccaaaagg tttagatatt   5220
ggtattacag ctttaattgg agctgttgtt gctatcatta caggagtcgt aagtctttct   5280
gagataaagt ccgtataatt gtgtaaaagt aaaaaggcca tataacagtc cttttacggt   5340
acaatgtttt taacgacaaa aacataccca ggaggacttt tacatgaccc aagtacattt   5400
tacactgaaa agcgaagaga ttcaaagcat tattgaatat tctgtaaagg atgacgtttc   5460
taaaaatatt ttaacaacgg tatttaatca actaatggaa aatcaacgaa cagaatatat   5520
tcaagcaaaa gaatatgaac gaacagaaaa ccgacaaagt caacgaaatg gctattatga   5580
gcgcagcttt acgacacgtg taggcacgct agaattaaaa gtacccagaa cacgtgatgg   5640
ccatttttca cccacagtgt ttgaacgtta tcaacgaaac gaaaaagccc tcatggcttc   5700
aatgttggaa atgtatgtat caggcgtttc aactcgtaaa gtatcaaaaa ttgtggaaga   5760
actttgtggt aaatccgtct ctaagtcctt cgtttctagc ttaacagaac agctagaacc   5820
tatggttaac gagtggcaga atcgtttatt atcagaaaaa aattatcctt acttaatgac   5880
cgatgtactc tatataaaag tacgagaaga aaatcgagta ctctcaaaaa gctgtcatat   5940
agcgattgga ataaccaaag atggcgaccg tgaaattatc ggcttcatga ttcaaagtgg   6000
cgaaagcgaa gagacctgga caacattttt tgaataccta aaagaacgcg gtttacaagg   6060
tacggaactc gttatttctg atgcgcacaa aggattagtc tctgccatta gaaaatcctt   6120
caccaacgta agttggcaaa gatgccaagt tcacttccta agaaatatct ttaccaccat   6180
tcctaaaaaa aattcaaaat ctttcagaga agctgttaaa ggaattttta agttcacaga   6240
tattaactta gcgcgtgagg ctaaaaatcg attgattcat gattatatcg atcaaccaaa   6300
atattcaaaa gcttgcgcat cattggatga tggattcgaa gacgcctttc aatataccgt   6360
acaaggaaat tcccacaatc gactaaagag taccaatcta attgaacgac tgaatcaaga   6420
agtacgcaga agagaaaaga ttattcgcat cttccccaat caaacatcag ccaatcgctt   6480
aattggagcc gttcttatgg acctacatga tgaatggatt tattcttcaa gaaaatacat   6540
caattttgat aagtagaaat ggtaaaaaca ttggattcga cagttgcgga tgtacttcag   6600
aaaagattag atgtctaaaa agcttgtagt taaagctttt tagacatcta aatctaggta   6660
ctaaaacaat tcatccagta aaatataata ttttattttc tcccaatcag gcttgatccc   6720
cagtaagtca aaaaatagct cgacatactg ttcttccccg atatcctccc tgatcgaccg   6780
gacgcagaag gcaatgtcat accacttgtc cgccctgccg cttctcccaa gatcaataaa   6840
gccacttact ttgccatctt tcacaaagat gttgctgtct cccaggtcgc cgtgggaaaa   6900
gacaagttcc tcttcgggct tttccgtctt taaaaaatca tacagctcgc gcggatcttt   6960
aaatggagtg tcttcttccc agttttcgca atccacatcg gccagatcgt tattcagtaa   7020
```

```
gtaatccaat tcggctaagc ggctgtctaa gctattcgta tagggacaat ccgatatgtc   7080
gatggagtga aagagcctga tgcactccgc atacagctcg ataatctttt cagggctttg   7140
ttcatcttca tactcttccg agcaaaggac gccatcggcc tcactcatga gcagattgct   7200
ccagccatca tgccgttcaa agtgcaggac ctttggaaca ggcagctttc cttccagcca   7260
tagcatcatg tccttttccc gttccacatc ataggtggtc cctttatacc ggctgtccgt   7320
catttttaaa tataggtttt cattttctcc caccagctta tataccttag caggagacat   7380
tccttccgta tcttttacgc agcggtattt ttcgatcagt tttttcaatt ccggtgatat   7440
tctcatttta gccatttatt atttccctcc tcgacttaac tatcaaacgc ttcggttaag   7500
cttaaagcac accctttctg cgtcctcgta ttgacgcgac gtaaaatttc aacgagcacg   7560
ccgggatact taccatattc tctgctaatt atcccgacat catcggtaac aataaatgct   7620
ggataactgg ttgctgacgc atccatataa ctcatcaacc ccggcgttcc atcaggtaca   7680
ggtttcaacg tttcaggatc aagcgctcgc gcatataccc acggcggaac atgtttacgc   7740
tgcatttcat cctcaaagaa acaagtgttg agttcaactt gattaaatat atctcggatc   7800
tgactaatat cactgagatt gaaagtatca aataaaagat gattgaaatc atcacgtttc   7860
agagattctt tttcgtaact tttccagccg cctccggtta tgatataaag gcttttatct   7920
ccagaaaatg agattttttt atctttcata taatggcaga gtaaataaat aaagtatggc   7980
gaaccaataa gacaaagatc tttcccttga ttttttattc gttcaagact attcaatgtt   8040
ttaacaaaat ctattcgttc ttctgttacg gtaaatgtcg taggatataa caattccacc   8100
aaactcataa catatttaaa ccaaatatta tgagcattaa atctatctgg tcccaaattg   8160
actaattcta tttgatgatc aaaccaacta ccaacatatt tcatgccata actcacagag   8220
cctaagagtc tctcaatact taatctgtca cgcgccacct gactttttaa accattcgtg   8280
ccgctactgg taaaccaact ttcaatctcg ttttcctgag aagttaataa gcgagtaaac   8340
ttaaaaaccg atgttgggaa tacaggtatg tcatcaattt ccgtaatatt gtcatctact   8400
ttgtgtgcct gacagtagtg acgatattct cgacaatgtt tataatgatt acgaaatgca   8460
tcaagcacaa gtttctttct gatttttttcc tgctcgtcgt aagaccacac taatggatcg   8520
ctcgaaaaaa tcaaatcatc aatttctgag cttgctgtaa tttcttgttt atcaacatat   8580
gaagtcatac ctgttttcct cctcgactta agacagagaa attgcttgat tttcaatctc   8640
aattctcatt cggcgttcat tgactgtcgc aatagttaaa tgttcaaatg acggttcagt   8700
aatatcaaca tcaatatcca gatgatcatt atccatcgcg atagcggctt tcgtaaccga   8760
ttgataaaaa ttgcgcagga ccactaaatt ttcactcaag tcatgcgaac ttcctaacaa   8820
agaatatatc ttgcatcgat tactacgaat atttgataac aatgtgataa cttcatcttg   8880
cttgacccaa ttatcgttat ttgcagtaaa agcaataaac ggtatatcaa gatacatcat   8940
gttattaatt gtagaagcta aatcttccca accaaaatca agacaatctc tcgcaaagac   9000
ttcagcaccc aatttatggc cttcaaaatc tagattatcc ggcaattcat taatgggtag   9060
actgagataa tcaaacccta aagctctttc aagagaatat cttaagttaa caacaccgac   9120
tgcggtgatt aaaaacgaag cattgatttc agataggctt gcataagcta tccgcgcaga   9180
taagcttgaa gccaacatac cgaagttatt tatttttcgt gtagttaacc aatcaaccac   9240
tgctaacaag ctctgctttc ctatagacat tgtaaattca tcaattgtcc ctgaactcaa   9300
tccaacgtgg tgaagcgaat catagcggat cacatgaaat ccattccgcg ataaatattc   9360
cgccagacca gcaaaatgat ccatcctgcg ggcaaaacca gacgcaataa taatggcatt   9420
```

-continued

```
ctttctcttt gggctgtttt cttctggcag cgtttcccaa acatgaattt ttttatttcc   9480
ttcaacacaa ataacgtggt cgatggtttt atattttgat tcattttcca tacttttact   9540
cctcctcgac ttatgggaca aatacaagga acttatcttc ttccaggaat cgagtctgtt   9600
ctatttcaac cgcaacatcc ttagccgtat agttagatgg cctttcatga gaaatatatg   9660
tcactaatcg ttgcaacggt ctcattccgt catgagatcc accaactcga aatatgttat   9720
tcattcctgc ttctacaatc ctttccgcac cttttaatgc taacgcatct cgatatttaa   9780
atgatgactc ccaaggaaaa atagatatgg tttgcgtctt attttttga acataaggca   9840
atatttgctc aatattatcg acgtgatgaa ggtacacaca tctgccaagt ggttgattaa   9900
attccacacc tgcatttgac tcaataatca tccaacgttg atgaatatcc acctctactt   9960
ttaatccagc aaacaagctt tctttttgaa ctaaagaata ggccgccttt tcatcaaaat  10020
cttttttggc attcggtaat atatgcgcat atagattaag tttttctatc aacgctaact  10080
taaattcctc ataatgattt cccatgtaat atatgttttg ggcagaaaaa caagctcgct  10140
gatcgtaaaa acaaacatca tgagccgcac ctgtcgctgc ggacgtcaaa tcaacaggat  10200
tatcgataat gcaaagactc tttttagaac caaatttaat cacatcagca taagatggcg  10260
catgctctac cgcccaatta atcgcatctg gccctcccca agcgacaata acatccgcat  10320
gtcgcataat ttcttttgcg agtgatgtat caccttggtg gggccaatat ataacagata  10380
aagagcgcgt tatcggatga ttagggtcta catcaataaa acttaacgct aatgcattag  10440
cggtaaaagg atcggttgac gatgttttta taatacactg attcttagtt aaaattgcgc  10500
gtaatataga catgatccca gataatggaa cattacctgc caacagatgt acagatttac  10560
ctttcggaaa agcccgaaca taactttcat cctgaggtag ccattcatcc atgatatggc  10620
gagaaccaag ttcattttct acaacatcat aaaggccgcc tttagaacat aaaatcatag  10680
atatccaatt ggcctctagc ttagccattt cttctgaata tcccatatat ttttttaagt  10740
cacgaatgta tgtcctgcgt cttgagtatt cttcattttt ccatctttgc cctaccgtat  10800
agagaaaatt gacaatgtta tgcaaccgta attcgttatt tccattacaa tcaataatgt  10860
tttttacatg agagtcattc aatattggca ggtaaacact attatcacca aaattaatgg  10920
attgcactaa atcatcactt tcgggaaaga tttcaacctg gccgttaata atgaatgaaa  10980
ttttttagt catatttgcc atcctcctcg acttaggtat attccatgtg gtacttctta  11040
atattatcat caacaatatt gattacattt ttttggctca tcaaatcatt cattggttca  11100
aaggacagca atacactttt cgcaccacac ttttcaattg ccaacttagc cgcagttata  11160
cactccgtat aatttccgac agcgttttct gcaattattt cttcaagttt attttcgaaa  11220
ttttcattag ggtgcatttc aagaacataa tcactaataa atgcacgcgt ctcttgttta  11280
gctttattac tatcttcgtt atagttaact aatatcatta actgatggtc tatctctgat  11340
aggtcaacgt catatttatc cgcaacggct ttatatcttt cagcatattc atatctaaca  11400
tcattagaat catcccactt aaagatgaga ggaatacctt ttttggccgc ccactcaaca  11460
atatgatgac tggttgctgt tacatatttc cgaggtccgc ctggcgtata agcatgggga  11520
tttacagata ttttagggaa gctataaaaa tcgttatctg gattacaata gcctgttgtt  11580
aaagcatcgt taatgatttc ataacactct tcaaatagtt gctgttgata ttcaaccggg  11640
cgattaaaaa aatgcatttc atcttttttt tcgcaatcac taaaccctaa aataaatctc  11700
ccttcactta actgatccaa taagcaagct tcctccgcta tggcgacagg atgatgagtt  11760
gtaatgatgt gatttaatga accaatttta attttctctg ttaaaccgag cagaaaacca  11820
```

-continued

```
gaaacagtca gaggagcgcc gacaacacca ttatctgaaa aatgattttc atacactaaa  11880
atctgttcaa aattcaactt atcaacatac tccgttattt cctgcatgcg aactatactt  11940
tgttcttgaa cagttgttga attgatgaag ttaaggaaga acaatccaaa tttcatttct  12000
ttctcctcct cgacttaata taatagcgaa cgttgttttt ctttaagaaa tggcatgaca  12060
tcagactgga agagcttcat ggaagcaata atttcgtcta ctgttccatt agcttcaaat  12120
ccacaacaaa tatttgatat tcctgtagca tcaatgtctt tttgaattat gtcaatacat  12180
tcctgcggcg ttcccacggg attgatttcg taactgtaat caatacggcg attagtatct  12240
ttatgtcctt ttaatacaaa gtcacgccac tgccctttat tgaaatcata acctcttgtt  12300
tggtctgaat catcaaaaat agtcgtagca ttcacataag aatcatacca atgccccaga  12360
aatttccggc aaatctcttt cgctttaatt gagtcatgat ctacagatgt tatatatgat  12420
aagcaatggt cgatattatg aatatcgtgc ccatattctt gagccacttc attataaagc  12480
tcaagttgtg ctttcttttc gttagtattt ataatccaac ttaatatcat cggtaggcca  12540
aattgagcag cccactcagt cgtcgaagct gattcagcca ccacataaac cggtgcgcca  12600
cctctgctat acgccgcggg gtttactttt accttatgga acttgatatg ttcattatca  12660
gcttccatat atccctctgt catgccattc tttatcagcc cgtaccagca ttccgctaag  12720
gcgcgactgt tattcatatc tgtgccgaat acgcgaaagt ccttgttgta aagccctcgg  12780
caaataccaa accgaaatcg tccttttgac atttgatcca ataaattcac atcttcaagt  12840
tggcgtactg gatgggctgt gggaagaaca atagcggcag ttcctacatt caattttta  12900
gtcgcgccaa gtaaatatgc agcagcgaca taagggttac caagcaaacc aaactccgtg  12960
aaatgatgct ccagtaacca tacggtatca aaaccacact cctcagagat gcgacctaat  13020
ttaaccaaac gtttcattac ctctgtttga gaaaattggg gaggttggta tgtaagcaaa  13080
aagtttccaa atttcataga gagtcctcct cttgcttcat ctgcaggcat gcaagcttga  13140
gtattctata gtgtcaccta aatagcttgg cgtaatcatg gtcatagctg tttcctgtgt  13200
gaaattgtta tccgctcaca attccacaca acatacgagc cggaagcata aagtgtaaag  13260
cctggggtgc ctaatgagtg agctaactca cattaattgc gttgcgctca ctgcccgctt  13320
tccagtcggg aaacctgtcg tgccagctgc attaatgaat cggccaacgc gcggggagag  13380
gcggtttgcg tattgggcgc tcttccgctt cctcgctcac tgactcgctg cgctcggtcg  13440
ttcggctgcg gcgagcggta tcagctcact caaaggcggt aatacggtta tccacagaat  13500
caggggataa cgcaggaaag aacatgtgag caaaaggcca gcaaaaggcc aggaaccgta  13560
aaaaggccgc gttgctggcg tttttcgata ggctccgccc ccctgacgag catcacaaaa  13620
atcgacgctc aagtcagagg tggcgaaacc cgacaggact ataaagatac caggcgtttc  13680
cccctggaag ctccctcgtg cgctctcctg ttccgaccct gccgcttacc ggatacctgt  13740
ccgcctttct cccttcggga agcgtggcgc tttctcatag ctcacgctgt aggtatctca  13800
gttcggtgta ggtcgttcgc tccaagctgg gctgtgtgca cgaacccccc gttcagcccg  13860
accgctgcgc cttatccggt aactatcgtc ttgagtccaa cccggtaaga cacgacttat  13920
cgccactggc agcagccact ggtaacagga ttagcagagc gaggtatgta ggcggtgcta  13980
cagagttctt gaagtggtgg cctaactacg gctacactag aaggacagta tttggtatct  14040
gcgctctgct gaagccagtt accttcggaa aaagagttgg tagctcttga tccggcaaac  14100
aaaccaccgc tggtagcggt ggtttttttg tttgcaagca gcagattacg cgcagaaaaa  14160
aaggatctca agaagatcct ttgatctttt ctacggggtc tgacgctcag tggaacgaaa  14220
```

-continued

```
actcacgtta agggattttg gtcatgagat tatcaaaaag gatcttcacc tagatccttt  14280
taaattaaaa atgaagtttt aaatcaatct aaagtatata tgagtaaact tggtctgaca  14340
gttaccaatg cttaatcagt gaggcaccta tctcagcgat ctgtctattt cgttcatcca  14400
tagttgcctg actccccgtc gtgtagataa ctacgatacg ggagggctta ccatctggcc  14460
ccagtgctgc aatgataccg cgagacccac gctcaccggc tccagattta tcagcaataa  14520
accagccagc cggaagggcc gagcgcagaa gtggtcctgc aactttatcc gcctccatcc  14580
agtctattaa ttgttgccgg gaagctagag taagtagttc gccagttaat agtttgcgca  14640
acgttgttgg cattgctaca ggcatcgtgg tgtcacgctc gtcgtttggt atggcttcat  14700
tcagctccgg ttcccaacga tcaaggcgag ttacatgatc ccccatgttg tgcaaaaaag  14760
cggttagctc cttcggtcct ccgatcgttg tcagaagtaa gttggccgca gtgttatcac  14820
tcatggttat ggcagcactg cataattctc ttactgtcat gccatccgta agatgctttt  14880
ctgtgactgg tgagtactca accaagtcat tctgagaata ccgcgcccgg cgaccgagtt  14940
gctcttgccc ggcgtcaata cgggataata gtgtatgaca tagcagaact ttaaaagtgc  15000
tcatcattgg aaaacgttct tcggggcgaa aactctcaag gatcttaccg ctgttgagat  15060
ccagttcgat gtaacccact cgtgcaccca actgatcttc agcatctttt actttcacca  15120
gcgtttctgg gtgagcaaaa acaggaaggc aaaatgccgc aaaaaaggga ataagggcga  15180
cacggaaatg ttgaatactc atactcttcc tttttcaata ttattgaagc atttatcagg  15240
gttattgtct catgagcgga tacatatttg aatgtattta gaaaaataaa caaatagggg  15300
ttccgcgcac atttccccga aaagtgccac ctgacgtcta agaaaccatt attatcatga  15360
cattaaccta taaaaatagg cgtatcacga ggccctttcg tctcgcgcgt ttcggtgatg  15420
acggtgaaaa cctctgacac atgcagctcc cggagacggt cacagcttgt ctgtaagcgg  15480
atgccgggag cagacaagcc cgtcagggcg cgtcagcggg tgttggcggg tgtcggggct  15540
ggcttaacta tgcggcatca gagcagattg tactgagagt gcaccatatg cggtgtgaaa  15600
taccgcacag atgcgtaagg agaaaatacc gcatcaggcg aaattgtaaa cgttaatatt  15660
ttgttaaaat tcgcgttaaa tatttgttaa atcagctcat tttttaacca ataggccgaa  15720
atcggcaaaa tcccttataa atcaaaagaa tagaccgaga tagggttgag tgttgttcca  15780
gtttggaaca agagtccact attaaagaac gtggactcca acgtcaaagg gcgaaaaacc  15840
gtctatcagg gcgatggccc actacgtgaa ccatcaccca aatcaagttt tttgcggtcg  15900
aggtgccgta aagctctaaa tcggaaccct aaagggagcc cccgatttag agcttgacgg  15960
ggaaagccgg cgaacgtggc gagaaaggaa gggaagaaag cgaaaggagc gggcgctagg  16020
gcgctggcaa gtgtagcggt cacgctgcgc gtaaccacca cacccgccgc gcttaatgcg  16080
ccgctacagg gcgcgtccat tcgccattca ggctgcgcaa ctgttgggaa gggcgatcgg  16140
tgcgggcctc ttcgctatta cgccagctgg cgaaaggggg atgtgctgca aggcgattaa  16200
gttgggtaac gccagggttt tcccagtcac gacgttgtaa aacgacggcc agtgaattgt  16260
aatacgactc actatagggc gaattcgagc tcggtacccg ggatcctct agagtcgacg  16320
gtatcgataa gcttgatatc gaattcctgc agcccggggg atccactagt tctagaatca  16380
gaccatggta cggtgaatat tcaattcgtg cagaaaatct tcctttgtta tcatcaagtt  16440
ggtgccaaaa ttcaccatga aaaaagtatt cttttgttag ttcgtatttt tttgttgcca  16500
tgtactgctc catttgtttc tgagaatcct tcagaatagt aaaaatacta ctcaaaactc  16560
gtcttcaaga tctctggcta tctgctcatt ttcatgatgc tcaacagcat cactgatcaa  16620
```

```
attcatcatg ttattaagaa actcctctac aactttaaac gcatcattga gcgtagctgt  16680
attgaatgta tgtatctttt catccgttgt tttcgttttc ccgttacgat gaactatgtc  16740
atgcctcagt ttcatcaatt cattgatatt tttgagtgga aaacgtggat attgcttagg  16800
ttgcaggact gctttatata tttcaactac cagttggatt ctatgataaa gaatatctga  16860
aaggtactcc tgtacatatt tgtttgcatt agactcttta tttatcaact cagacagaga  16920
gatattcttt gctttcagtt catttatgtt tcttatggca ttttctacat atctgttatg  16980
tgacaataca acgcttttaa tcatttcgct aagacagttt tccattattg tcacaatgta  17040
tgcgattttc atttttatga aaacttcact tgtagattgt tttccctctt cttttatttg  17100
ttctaaaagg tttattgcta ttttataaat ttctgtatgt ggatgctgtt ttaaccattt  17160
ttcgttttca tattcttcca tagccatatc agaaagaaag tcctgatact cgtcatagtc  17220
cttttcaagt aactgccatt cttcagaatc ctcctcaaga tctgggctgg aaagccgttc  17280
tcgtatccat tcctcacggc gactttcctc gacttgcata acccaatctt ttgtagctcc  17340
cacaataccc tccttatgtt cattgctaaa tatcaatagt cactttatcg gagactacgt  17400
gaaaaatctt ctcctttccc cctgcttttt tatcagattt cacgcagcgt accgccgcta  17460
ctgtatccat caaaaaaact gatagctttt taatcatctt ttgtgctgca acttactgaa  17520
aaaaggatta atggaaacgc cgataacggc attgatctgt tggccaacgc gaccggcagc  17580
attggactta acaaaaaaac tgaaagaaaa tcccccaaat gaagggaaaa aacggaagaa  17640
cagtcgaacg acaggcacaa aaaaacccga ctggtaatcg ggctttttcg tgttttccag  17700
tcctgagttg gtggctctga ctggaggaag atactctaca tccaacatcc acaatattat  17760
ggcactagac accagttgtc tagtttgact tcagattgtc tgtcaatggc catttcttta  17820
aatgaatttt atgcgtgcat ctgtataatc tttgtgttgg cgctgtacag tgtgcctccc  17880
ttgcttctaa cccctgcgct atctggggat gaacgaatta aagtcctggc tgaacaaaca  17940
ggtggtgctg tgttcagtgc tctggcaggg ggaaggtact ctacatccaa caatgtgaga  18000
gagccgttgt gacaggcgat gtatgagcaa gcaacggtga cttcctccag tatcaaccta  18060
gagaaacgga tgatgaatct gttaatcatc gttctcaggg ctgtgctcgc cattgcaaac  18120
gcgctgattg ccattcagaa actaatcgag tgattgatgg cttaactaag ggagagacgt  18180
ttaccgcttc ctgcccttta acaaaggagt gtttatgagt tttgaacaat tatttacact  18240
aacgacccaa cgtcgttggg tttgccgcag aaaatttatt catttaaaat agatctaaat  18300
gaagcgggaa actgcagacg taaaaaaacc gactggtgag gtcggctttt ttacagttcc  18360
ggtacgagct ggtaactcgc ccggaagaga aactctctac aactgacaac agtatgataa  18420
tccgtgaagc ctgattatgc aatatgacag gcggtgacta cgcgttaacg gtttgcttga  18480
aagttagata aacgtataat cagagggtta gtgctgtggt gagtctttcc ctgcattccg  18540
ctaaatgcgg catgaacagc ttcaaagtcc tgacaggtaa tacaggtggt gctggttatc  18600
tgtgctctgg taggagtgag actctctaca actgacaaga cgaagagaag ccgtggtgac  18660
aggcagcgta agagcaagcc acggtgtctt tactccattt atggagaaaa cggatgatta  18720
acctgttaat catcgttctg agggcggtag ctgcgcttgc aaacgcgctg attgcagttc  18780
tggaactgat ccgtcagttc atcgattgat gactgcggaa acgtaactaa gggcaggaag  18840
tgcaccgctt cctgcccttt aacaaaggag gtgttatgga ttttatgagc attttggggc  18900
gctgtttact tcttcctttc cctgttgcga tgtttgtcgg ttgcctgttt ccaggcatcg  18960
atgatcgttt tactggaatg ttcatgagtt ttattgtcgg ttgtctatcg tggtatatca  19020
```

-continued

```
ccaagccaaa accgcaaaag gctgaggtcg cgtaagcggc cttttatttt gatacgcatt  19080

agttacaaca ttcaatttgc tttttaaaaa tatccacttc agcacctccc tcataaataa  19140

cgtcaaccag tttattgagc tcaccctacc ctactcaccg gaggattgca gggatttacg  19200

ttttattgcg ctactgattg tgccgcggct gcaccctagt accttctgta cctgtgtcca  19260

ggagctgcca ctttctatca acctgataat tgcatcatgt ctggcttgat taggtttacg  19320

ccctttatat ttgccgtctt tccttgcttt ctctatcccc tgtttctggc gttcccgccg  19380

ttgttcatag tcccttctag caacagcggc cagcatatcc agcagcatat cgttaatggc  19440

tgcaaacaac cggctgtcaa actcactcat accagaatta atccaggtcg tcggcacatt  19500

cacggccata acccggatat ctttctgacg gatcattttc ttcagcgtat tccagtcttc  19560

ccctgacagt cgggaaagtc tgtccacatc ctcgataagc aaaatgtcat tttgctggca  19620

atctctcaga agacggaaga gttccgggcg gtcaagacgg gagccggatt cattctcaat  19680

ataatagctg caaatgatca ggcctctttc cctggcaaaa gcctcgatag tttccagggc  19740

acgcgaagca tcctgttctg ctgttgaagc tctcagataa gcgcggacaa agtttgttgg  19800

tgcatttgaa gtcatattac agaaccagtt cgcataaggt cacaccacta tacccaaaat  19860

gaaccagaaa gtggatcgac aggaaaggca cactctaaaa gaaccgaaaa aacaaataat  19920

gagtaaatgt gacatcgtca cccatactca taaactcaca tgctcatata cacaacaaac  19980

tcaaatgagt atgtgctctt taactcataa actcatatta acctttactc atgcaaagag  20040

tatggtaaac tcaaaaactc acaagagtaa ttgagtagat acacaattga gggtttgagt  20100

atgaaagtaa tctcatttct gaatccgaaa gggggttcag gtaaaacaac tgccgtaatc  20160

aacatagcca ctgcgttgag cagaagcgga tacaacattg ctgtggtaga tacagatcca  20220

caaatgagcc tgacgaactg gagcaaagcg ggcaaggcag catttgacgt atttacagct  20280

gcatctgaaa aagacgtcta tggaatccga aaagatctgg cggactatga ctttgctatt  20340

gtggacgggg caggttcgct ctcagtaatc acctccgcag ccgtcatggt aagcgatctg  20400

gtaattatcc ctgttacacc cagccccctg gatttctccg cagcaggaag cgtcgttact  20460

gttctggaag cacaggctta cagccgcaaa gttgaagccc gctttctgat cacccgtaag  20520

atagaaatgg caaccatgct caatgtgctg aaagaaagta tcaaagacac tggtgttaaa  20580

tctttccgta cggccattac acaacgtcag gtttacgtga aatcaattct ggatggtgac  20640

agcgtgtttg aatccagtga tggcgcagca aaaggtgaaa tagaaatcct tacaaaagag  20700

atagttagca catttgagta attactcatt cactcatata atcaaataag tataacaacc  20760

ggagtaacct taatgtcact tgaaaaagcg catacggcag taaaaaaaat gacctttggt  20820

gaaaacagag atctggaacg agtagtaaca gcaccagtat catctggaaa aatcaaacgt  20880

gttaacgtca attttgacga agaaaaacac acccggttta aggctgcatg tgccaaaaaa  20940

ggtacatcga tcacagatgt ggtgaaccag cttgtagata aatggctcaa agagaacgaa  21000

taatatctga ggatatatca tggataaaaa cgtcgttgat gcgctgaaaa cgctattaga  21060

agcgttaccg gaagaggtgg taacagaagt cacatcaaaa ctaaatcctt cggcaagcca  21120

tattcctgaa gaaaacagta agcaattgac agcaaaagca agactactga atttccggct  21180

aaccgaagcc tatgaagaaa tcctggaagt cgaagctatc agaacaggcc agagcaaaac  21240

taccgttcta aaggcagcac tggcgatgta caacagccag gatgaaaaca taaagaatca  21300

ctggctactt gagtctgcaa aaattaacta attcaggata tagattatta gtaggagttc  21360

gggcaataat ggatgataac tctacgtcag taaccagcaa agaagatgtg caggatattt  21420
```

```
ctttaaaaaa ctggctaaag aataaaaaaa ccattgtatt acttatattt actgcattaa  21480
caaatgttgg caatgtcctt tcgacgattg atattatcac agataaaacc agttcttttt  21540
acacatggct tggggaatcg aaaaaattcg aaggccattg gaccaacaat acagaaggat  21600
tcatagacgg cactcctgat tttttactca agaatgcagg cgatgtcctc ataaaatttg  21660
acctgaacat caaaggtggc gaagtgaggg gagagcttca caccgacgca cgactaaaaa  21720
tgtgtgaaac tatagaagaa aagttaaaaa ctttgtgtac attaatagcc tcacatccac  21780
taatgattga gggggaaaaa tcaccatttt ccaatgaatt cgatgcctat attactgagt  21840
atagaaatgg agataaaaaa atagtcgcaa tattaaatat gaaaattaca gacgatgaca  21900
aaatgacaat aacaaataca atgagaacac cagaatcagc attattttca actaaaatat  21960
atgctataaa aataataacc gaagaataac ttaataacaa aaaaggtatt aaagtgaata  22020
ctggaataac aattgatttg accaaccttt cagaagatga attgcttgat ttatattcaa  22080
tgtataaaag tgcaaacata gcacatcaac tatggtgcag acgccatgaa aatataccag  22140
agcatttttc gataatattc gtgacgcttt tagaacgaat aaaaagggtt acagaaaaga  22200
actcagaagg ggtaaaaaca ccagatgtag acctggatgc attaattgac accatttata  22260
ttggttgtcg ttcaatgttc tgtgaaaacc ctggcttaaa aaataactac actctgcaaa  22320
actgcctgag gaaagccaat tatcacaacg aagctagagt gatagataat attttacagg  22380
aaaaaaaatt cacagattcc atcatgaaag atgagtcatt ttttagtctg gtgaaattag  22440
tttccaataa gtccattgca caccaggaga gcctttcagg aaaaaaacgg gaaaagatag  22500
actatcgata taaattctta aatgacaatt caaatatctg tgagtttcag tattacattt  22560
ttagatgtca ccgtatttat gagaatattg tgaaagaata tggggataca ttactgaatg  22620
agcttaaaat aaaaaacaat gatatataaa gaatgccccc atatgaatag aaggaagaat  22680
catactaata aattttccag cttatcgctg gtaagcaatt ctgccagcga atcacatttc  22740
ataaaatcaa tatccatttc gtccagaaca tcacagtagc tgacatcatc aagactaatg  22800
acaatcacag gaacaccctc tttgagatca aacactaaga caggtaatga aatggagttt  22860
atcttttcaa aatcactaaa aaactgttca gttccatatt cactggcagg aaaaagaatc  22920
tcacttaatc tcacacaata aaaaacatga tagtgttctt taaggttatc ctttaaaata  22980
ttaacagcct tagtatattt ttcgttaata aactctttga ccaaatattt cataaaactc  23040
tccaacaaga accgactgta ggtcatcggg caaacgttgc ggaatggcgt cagagacgtc  23100
attttgcggc gtttgcccta tcctgcatcg cagtggcatc atttctggct tatctcgcta  23160
ctgttctcgg tgctttcgtc cgcaggttcg ggaacaagta acttgtgcca gggcatagtt  23220
ttgttgagca gctccatcag aggctcagcc agcagtccca aaatccaggt tgccgtaatc  23280
accggtatag tgagattttg tggcgtccat aactggtgat cgagatgata ccaggtgatg  23340
acacacaaaa taccacccag ccagaacaca gcccatttaa acgcaccaag aatggctaac  23400
acaaaaacaa agataaaatg taaaacactc gcggcaagaa gacgaagata aaaccatccc  23460
cagtcaagcc acttaacaaa agtgctccct gttttcactg caaaacgttt cttacgctcc  23520
ctggcgattt ctttcctgaa tttagcacgt tcttccccct gagggaattg atagatttta  23580
gccatgagtt acctcatttc gatctcaaaa cgaagtttat gcaattatcc tctgaaaccg  23640
tatggtattc tgatatctag gccttcactt tctttatcta ttttataaga aaaccttagc  23700
tttgatgctc ttcttgcgac tctctcaacg attttaactt cgagatgatt aatctctgta  23760
tattgattta ttttttcaat gttttttttgc agaaaaactt tattaaagtc cttaaaattc  23820
```

-continued

```
tgataaaggt aaactttttc gccattatct attctgaata attcaagttc atcctttaat  23880

acatctactt caatgtcaaa aaatgtcttt ttaccactgc tgtattgttt cctgataaac  23940

tgataaagca tatttgaatt ttgatcagca agtcttacag acgatatcaa aacctgagta  24000

gtgtaagaat cctttaacat cgtgatatat ggctcaatga catgtgaaaa agcaatatca  24060

atatatcctt cactttcaac ataatcacaa aacgcagtca ggttcataag cctgactgca  24120

tcagaaggta atttacctct cttcttcgta tgtccagaga tttgattgcc ctgagctgtg  24180

agaagttgat ttcgaggaat gcgaataaca ctggcctgaa gttcttctgc cccctctttc  24240

aactgccggt aagcacctgt tacatcaata tcagcgataa atgcatattc ccgagccgta  24300

atacgaaagg ttgccccctc agataactct tcacgtgaat caatctgcgc catagccata  24360

aacaaaattc ttctggcaga caaaggcaac gatgagaatg tgctgttaat ttcatttctg  24420

tggcgaattt ttgttttctt tgtaacgctc agtaagttca tacattacct gtggttttta  24480

agttctaatg gtgaaatcat aaccacaaag gcggaaatat gtaaagtggt ttatccacct  24540

tatgtatttc caccaaaaca cggatcacat gaaagaattt ttatcattaa tattcaatat  24600

gatagaaatg cgcaggtatc cacctttttaa cgtcatacgt tagattagag cactataaag  24660

aactaaagaa atgaagatac aaagatacga atatctgaat aaaaacagga aaatgcgtac  24720

ccatccacct ttcagtgcgt acccatccac ctttcagtgc gcagccatcc acctttcatg  24780

aaaattacag tgcgtaccca tccacctttc agtgcgtacc catccacctt tcattttgag  24840

gcgacaaaaa acaacaccta tcttaatgaa attattgata aaaaaactgg cacaatgttt  24900

gcagaataag ttaaagtaag ttaaagatct taaagtagat ctaccgatct acatttaaga  24960

tcttaaaaac aagaagttta ataagcaaaa aaacacaaaa aatctgtgga taactttgct  25020

caaaacaaaa aattcacact acctgtggat aactttgcgt aaacccggag gacagatcac  25080

tctgaaccaa gacaaccaca cataaaaaca atatgctcac tttttaacca ctgcgcgtaa  25140

ttgcctgatg ttatccttgt gctgttccgc ttcctcgctc actaactcgc tacgctcggt  25200

cgttcggctg cggcgagcgg tgtctccttt ctcaaaacca gaagagttca gatcatacga  25260

tccgttgatt gatccttttt ggatctttca ctgagaagcc ctgaatcgct ttctgtcgct  25320

tcgttcgata caaccatggt gaaaccatgc gaaatcgaaa aaatcgctca gaatgcgata  25380

cagcgcgttt tagagggtat ttacaaaaca gtcgttgcct tgaggaaatt ttgatcaaga  25440

ttgaactcct atccggatca tggcaacaga tcacagcaac aaggccgcta aaaagcgttg  25500

agcggcgtta aacaccgtca aaccgtagcc gactacaacg aaacgggaaa aacgctcaga  25560

acgcgttaca gagcgtttta aggcgatgtc ggaaagagcc atatctcacc tgttctgatg  25620

tttttctcaa catgagcact tttaagagtg cttttaaaga tgctattatg ccaatgagac  25680

aagcggaggg cttatgagct atcaaattct gacaaccaca gcggccagta ttactgacct  25740

gaaaaaaaat cctatgggaa ccgtagctga aggtgaaggg gacgctgttg cgatcctgaa  25800

ccgaaacgaa ccggcgttct attgcgttcc accaaaactt tacgcctact atcgggaact  25860

cgctgaagat gctgagttaa acgctgttgc tgatgagcgc atgaaaaacc cggaaattgt  25920

gaaggttaac ctggatgacc tatgaactgg cttttgaccg tagagcactg aaggaatggc  25980

agaaactcgg ccacaccatc cgtgaacaat tcaaaaagaa actggcagaa cggctggaaa  26040

atccacgcgt acccgcagcc cggttacatg gtcatgctga tcgctataaa atcaaacttc  26100

gtgcatctgg ctacagactt gtatatcaag tcattgatga gaaagtcgtt ttacttgtta  26160

tttccgttgg aagaagggaa agcagcgaag tctatcagat cgcagatttg cgctaagatt  26220
```

-continued

```
aatcatcaaa ggattaactg tttactgtca gaacaagagc attaaaaatt tgccacacct  26280
gcaaatgcag gtataataaa acacaagaaa gggaaacagg ttctctttca tccagagccc  26340
aaagtgggcg ggaggttaaa aatgcaaaac tacgctaagt ctgtagccac agagatttta  26400
cgtcaacttg gtggtaatcg ttttattgtt atgactggtg ctaaaagttt ttcttacttt  26460
gatgaaaacg gtgagtgcgg gttaactttc cgtttgccgt ccaattttgc aatgaaaggc  26520
atcaacttag taaaaattaa actggatttt actgatacgt accaggtgaa attttctcgt  26580
gtacggggtg atgaagttaa agatatttca agattcgata atatctattg tgatcagtta  26640
gcgtgtttat ttacacaaga aacagggtta cataccgtgt tatagataaa aaggggcatt  26700
aagcccettt tttagttatt atgaggaata atatggataa agataagata attaagaaaa  26760
acagaggtaa ttactcatat gtaatcagaa cgatggatga agatggggat gcggtttttc  26820
acgtcttaaa atatgttaag acgattgata aaactaaaag caggaaaaca gtaagaaaat  26880
tgataatgga cgaaaaactc aacctggcat cattgatgct tctggataat gggattttgt  26940
gtgattgtct gacaaaaggg gatgaaaatg cagaataaac ctacacctga agaagtaaag  27000
aatgcacggg ttgcggcagg tcttactctt aaagaagctg ctgatatttt tggttatcaa  27060
ctgaattcct ggcagatgaa agaaagtgca ggtaaggcca gtcgttcttt atctgttggt  27120
gaatatcagt atttattgct attagcaaat atgcatccgt cttacaggct ggtaaaaaaa  27180
taacttgcta tacctgcaaa tgcaggtata ataaaacaca agaaagggaa acaggttctc  27240
tttcatccag agcccaagct gggcgggagc taaaaatgaa agtattaact tttaaaaatg  27300
atactgtctc tgttggtgat gtctttgtat catcctgggg ctatgagcaa accaatgtaa  27360
ccttctacca ggttctttct gttcacggta aaaaaaccgt caccgttcgc gagattcgcg  27420
ctaattcaga atataccgat tcaatggtcg gctttaaaac tcccgtttta aatgatttta  27480
ctggtgaatg ttttaagcgc cagataaaag attttggtga tgagctggca atcaaaatcg  27540
aagattttga aactgcgtat aaaactctac cggaagaaaa acatcgattt tcttcttact  27600
actgattaat caggggggata ttcccccttt tagtaaaggt ctgaaaatgg aaagagagtt  27660
tagcgcaaaa gcatcattaa accgaaatat aaaattttgg tttgagcaat gtgggttatc  27720
taaagaaaga gttattcgtt gtattgataa ctggtatgac cttgcatacc caccatcaga  27780
acaggagaaa gcaaaaaaag aagcaattga gaagttaata aagtaaagat aaagatggta  27840
tcaggttgtg ggcaacctg ataccgtgac acctgattct attgcgagga ataaaatgtc  27900
ggaacgcata ttatcagcaa taaatgacgt tgaaaagggt gggcgtccgg ttttcccttt  27960
gatgccattc catgtctttc ctgagtatat ggcattactc agaaaagcac tggaaaaaaa  28020
gacacaaaag agaacagata aataaaccgg aggctttatg acaaaacatg attttgtgtc  28080
ctttgtcagt ggagaattgc ggcaaggcgc tgtacgcttt tctcttgctt ttaacagcaa  28140
aggagaaatt gttctgcact ggactaataa agcaggaata cgagtatggc ggatattaag  28200
tggtaatcgt ggcaaaaaac caagcaaagc taaccttgaa agaatgagta acttccggcg  28260
ctggcttttt gatgcccgtc agggcatgga aggctacact cagcaacctg aacagagcaa  28320
ccttagctga atagccgaag ccctcccgta tttcgggagg tgctttctga tatattgcgc  28380
gggactgcgc ttgcgcttcc tgccagaccg ttcgcggagc gaacctgacg gcactgtcct  28440
taccgcattg atcgggtttc cggtcgcaga cgtacgtatg ttcagccatg acaacatcag  28500
ccctttttgca tttttgttga tgctcaagca caatttatga gcggtgccag attcactgcg  28560
atgcaggata gggcaaacgc cgcaaaatga cgtctctgac gccattccgc aacgtttgcc  28620
```

```
cggtgaccta cagtcggtta ttgtcggaga attttatgaa aaaagttcaa ttcagaattg  28680
atgaaaatca gcataatgat ttgctggatt gtcttaaaac tctttatcca gatgaaccag  28740
ctttaacagt agctaaaggc atgaaacttt tagcaaatgc tttattaaaa agtaaagctg  28800
gcagtaagga cataaatacg tttttgata ataatgattt tatcaaaaca acgatgtact  28860
taacaggtaa acaaagggct gatattgaaa gagctgctaa tcgtcacgga tggacgttat  28920
cacgagaatg tcgttaccgc atacagacga cacttgaaaa tgaactggat ttctttgacc  28980
aggaactgct gatgatgaat cgttgccgta attcaattga taagatcggt cgtaatttcc  29040
attatatcat tgttaatgat cagaccaggg ttcttgataa agatggtttc tatcaggatg  29100
cggagcgtct tacaacagaa atttttaatc ttaagaatca gtttgagaat tacattatgt  29160
tatgtaaagg gagaactgtt tcaaataaag tggagatgta attatgggcg tttacgttga  29220
taaagaatat cgtgttaaac gaaagtcatc agaaaatggt cgtaagtcag ctttcgctca  29280
caaagtcaaa aatggtggaa agaactatag ccgcaatgtt caggaacgta tcaaccgcaa  29340
gggtgccagt aaggaggttg ttgtcaaaat atctggaggt gctgttactc gtcaggggat  29400
tcggaacagt attgattata tgagccgtga gtcagagcta ccagtgatga gtgaaagcgg  29460
tcgggtatgg atgggtgccg aaattctgga ggctaaagag cacatgatag atcgtgctaa  29520
tgatcctcag catgtgatga atgataaagg taaagaaaat aaaaaaatca cacagaatat  29580
tgtcttctcg cctccagttt tagcgaaagt aaagcctgaa gatttgttgg agtctgtcag  29640
gaaaacgatg cagaaaaaat atcctaatca ccgttttgtt cttggatacc actgtgacaa  29700
gaaagaacat cctcacgttc atgttgtttt tcgtatccga gataatgacg gtaaacgcgc  29760
tgatatcagg aaaaaagatt tacgggaaat tcgtacaggt ttttgtgaag agttgaagtt  29820
aaaaggttat gacgttaaag cgacccataa gcaacagcat ggacttaatc agtctgttaa  29880
agatgcacat aatacagcac caaaaagaca gaaaggtgtt tatgaggttg ttgatattgg  29940
ctatgaccat tatcagaacg ataaaacaaa gtctaagcaa cattttataa agctaaagac  30000
tcttaacaag gggggttgaga aaacatactg gggggctgat tttggggact tatgttcgcg  30060
ggaaagtgtt aaagcaggtg atcttgtcag gctgaagaaa cttggtcaga aagaagtaaa  30120
aatcccggcg ctcgataaaa acggtgttca gcatggctgg aaaacggttc acagaaatga  30180
gtggcagtta gaaaatctgg gggttaaggg cgtagacaga acaccttcag ccagcaaaga  30240
gctggtactt aacagccctg atatgctgct gaagcaacaa cagcgaatgg cgcagtttac  30300
gcagcagaaa gcatccacgt tacagtcaga acagaagctg aaaacaggga ttaagttttt  30360
gggcttataa gatttaatgt attgattatg cgagaaaaat atttatttta gttcgcttgc  30420
tcatcttttc accttaaaaa cagatcgaaa ttctgcgttt tagctatcat tcgatctatc  30480
gatctaaaaa acagatctgc aaaagatgaa tattctgtgt ttcattgcat acatggaata  30540
aatgaaagta aaattgattt atcaagatcg aaagatctgt tttatgtgtt gaacttagca  30600
taagccactt gtagtataaa cttcgcgcaa tagtaaaaag tctctcttca taggggcgtg  30660
atttctcaca agcaaccacg gttggcttgt gttttgtcac atctgtatat cggggattga  30720
gtatgaaagg acagaaacag ttttacctgc ttcagtgttc tccgcatttt catcagtcgg  30780
ttctgttgca gttatcccgg agcggtatcg cttactacaa tccagttata cgcactttct  30840
ataagaggcg tgactgtagt gcatacaggg gacaaatcat gccaatgttt cccggttatg  30900
tattcgttct tctggatttt gaggttgtac atccatcctg ctttacccgg atgaaaaatg  30960
tttatggact ggtcagtttt ggtgaatatc ctgctgaagt tcctctgagt gtcataaatg  31020
```

```
aagtaaaaga gcaggagaag attttttcga tgaatttaag cctgatgaat aactcctgtc  31080
tggcaaaaat acttctcctt gcagacgctt caaagcgtgg acgagtcttt gccgactatg  31140
tgtgtaacag aaaatacgac aggttaaaaa atgacagcta taaaaggaaa gcggaaaccg  31200
caacgcaatg tactctacct tcctacagaa gttcgtgttg aagttgaaaa aattgcaatt  31260
gaaataagct tcaagagggg gcgacgtatc tctgattctg gttttgttca gtatcttatt  31320
aaaaaataca aatctcaggc gatgaaagaa cttattcatg gggctgatat tcctgacgag  31380
taatattgtc ccaatgttct gaatgtggaa tatttatgtt atctacttct acttttcttg  31440
cgcttgccat gcaatgcgct gccagcgttc atcccgacac aacgcacgaa gtcgccaggg  31500
ttgaatcagg ttttaaccca tatgcgattg cggaaataat accaaaggtt aaacgtaaaa  31560
ctggtgataa aggcgtagta tcttactttc ctgaatcaaa ggaggcagca cttaagatcg  31620
ttaaaaacat tgaattacgg aatcatcgtt actctgtagg acttatgcaa ataacgagta  31680
ccaattttgc aaagttcggt acaacagcag agaaaatgtt tgatccatgc gaaaatctta  31740
aggtatcaga aaaaatactg gttgactgtt ataaacgagg tggcgactta gtgcgtgggc  31800
tgagttgcta ttattctggc aatcaagaaa caggagtaaa gccagaacct gaatttaata  31860
atacaagtta tgtacaacgt ataggattta gccctcctga taataaaaaa agttttattg  31920
ttccctctgt aaaggaaatg attaaaaagg agaataagac gactatcaca cctgaagaaa  31980
tcattatata tcctcaatac gccatgcgtg gcactgtatc aaatgaaaag gaaacaaaag  32040
atgttgaaat taaatctgaa taaacgttat ttaacgcttt ctctatttat ggctgcgttg  32100
atgctttgtg ttgcagaacc tgcttttgcg gatgatgtgt ctacgaagac aactggtttt  32160
ttacagaaaa taattgattt tttaacggat attcgtaaac ctgcaattac aattattgct  32220
cttgttattg ggtatattgc gatattttct cgtcaacata cctcatggat agtcccactt  32280
gttatcggaa ttatcatctt tattgttgca ccatatattc ctgactggct tgcgtaatta  32340
aaggatgggc gcactatgag tactcttttt aaaggtctta cgcgccctgc tttaataagg  32400
gggctgggcg ttccgctcta ccccttttctt ggaatgtgca ttatttgtgt tctgcttggt  32460
gtctggattc atgaggctat gtatgccctt attcttcctg gctggtatgc catcaggcgt  32520
gtaacacagt ttgatgaacg ctttttttgac cttctgtatc tgagaactct tgtcaaaggg  32580
catcctttat caaacaagcg attcagcgca gtccattatg cggggagcca gtacaatgaa  32640
gttgatattt caaaagtgga taactttatg aagctgaaag accagtcttc tgttgaagag  32700
ttaattccgt actcttcaca tatcactgat aatattatcg ttacaaaaaa ccgggatttg  32760
ctggcaacct ggcagataga cggtgcttac tttgagtgtg ttgattctga agatttgtca  32820
attctgacag atcagcttaa tacgcttata cgtagctttg aagggaaatt tgttacgctt  32880
tatcctcatc gtatcaggtg taaaaagggc gtcagaccag tatttaacag taaaattcct  32940
tttgtgaaca gagtaatgaa tgattattac gagtcattcc ctcagtctga atttttcgag  33000
aataaattat ttctgacgat ttgttttaaa ccttttacta cggaagataa agtaacacat  33060
ttcttttcac gcagtaaaaa acaaaaagat atctttaaag agcctgttaa tgaaatgaat  33120
gaaatttgcg acaggttgaa tacctatctg tcccgttttc attcccgacg tcttgggctt  33180
tatgaagatc atggggttgt ttattcagat cagttatctc tgttccagta tctgctttct  33240
ggtcgatggc aaaaggtcag ggttagcagt agtccgtttt atacatatct gggaggaaaa  33300
gacctgttct ttggtaatga tgccggacaa attaccgcgt cagaccatgc ccggtatttt  33360
cgttgcatag agattaagga ttattttcag gagacggatg ccggtattct ggatgctctg  33420
```

-continued

```
atgtatctcc ccgttgagta tgtcgtgaca tcgtccttta ctgcgatgga taagcagtca  33480
gcgattaagg cgctggatga tcagatcgat aagctggaaa tgacagatga tgctgccaaa  33540
tctttgctgg cagatctgaa agtcggactg gatatggttt ccagtggata tatttctttc  33600
ggaaaatcgc atcagaccct ggttgtcttt gcggattcac cggagcggct ggtgaaagac  33660
accaatatcg tgacttccac tctggaagat ttggggctga ttgtcactta ttcaacactg  33720
agtcttggcg cagcttattt tgctcagcta ccaggaaatt atacgcttcg ccctcgtctg  33780
agtaccctca gtagtcttaa ttttgccgaa atggaaagtt ttcataattt cttttcagga  33840
aaagaaaaag gaaatacctg gggggaaaaa ctgattactc ttcgggggtc aggtaatgat  33900
atctaccatc tgaattacca tatgacgact gaacatcaga atttcttcgg taagaacccg  33960
acgctggggc ataccgaaat tctcggtacg tctaacgtgg gtaaaaccgt attactgatg  34020
acaaaagcat ttgccgccca gcagttcggt acgccggaat cattccctgc aaacagaaaa  34080
ctgaaaaaac tgaccacggt ttttttgat aaagaccggg caggtgaagt cggtatacgg  34140
gcaatggggg gatcttatta ccgggtgaag gagggagagc cgacaggctg gaatcccgcc  34200
gcactgccgc caacaaagcg taatatcgct tttatgaagg acctggtgag gctgctttgt  34260
actctcaaca gtgagccgct cgatgattac cagaacagcc tgatttcaga tgcggttgaa  34320
cgtcttatgc aacggtcaga tcgctcttat cctgtcagta aactacggcc tcttatccag  34380
gagccggatg atactgaaac caaacgtcat ggacttaaag cccgtcttaa gccgtggacg  34440
caggggggaag agtttggctg ggtgttcgac aatcgggaag acacgtttga tgtcgataac  34500
ctggatgttt tcggtattga tggaacggag ttcctggata ataaggtgct ggccagtgct  34560
gcttcattct atctcatcta tcgggtcacc atgctggccg atggtcgcag gcttcttatc  34620
tacatggatg agttctggca atggatcaat aacgaagcgt tcagggactt tgtttacaac  34680
aagctgaaaa ccggacgtaa actcgatatg gtgcttgtcg tagccacaca gtcaccggat  34740
gaactgatta aatcacccat tgcggcagcg gttcgtgagc aatgcgccac tcatatctat  34800
ctggcaaacc cgaaagccaa acgtagtgaa tatgttgatg gtttgcaggt cagggagctt  34860
tattttgaca aaattaaagc tatcgatccg ctgtcccgcc agttccttgt tgttaagaac  34920
ccacagagga aaggtgaaag tgatgatttt gctgcttttg ccagactgga gctgggaaaa  34980
gcagcgtatt acttaccggt tctcagtgca tcaaaacccc agttagaact gttcgatgaa  35040
atctggaaag aaggaatgaa gccggaagag tggcttgata cctatctgga acaggcgaac  35100
ctgatttgag gaatcaccaa tgaaaaagca aattatggcg gcattcgtcg cttcactgat  35160
tgttatttcc ggcgctcagg cagggatacc tgttgccatc gacgccaacc ctgaatgggc  35220
gattgaagcc ggacgatgga cagaacgcct taagcaatgg gcggaaacgg taaaacatta  35280
cgaaaatcag ataaatgcgt acaaacagga gctgctgtca aaaacgggta tccgtgatgt  35340
gcagggactg gtgcagtccg cacagtcagt gagtcaggaa ctgatgcaga tttatgatca  35400
ggggaatgct tttattgacg attacattaa aaatcctgaa ggggcgttat cggaacaggc  35460
caaatcgtta ttgtcagatt acaaagtaac ggatacctgc cagaacctgg gatattccgg  35520
cgacctggta cggggatgtg aagcgacgtt cctttctcaa ctggcaagcg tggaatacgg  35580
taacaagctg gagagcaagc ttcgtcagga caaccagacg atgaaagacc ttattgatca  35640
agtcaaaaat gcgaaggata cgaaggccac gcaggatgca acaaacgctg ttgcacttga  35700
acaactgaag ttcgagaagc tcaaatttca gtatcaaatg tatcgcgata agcagcgaga  35760
tcttgcagaa tataaagaga agatggctca ggcagctttc agaaaacagc aacgtgaagc  35820
```

-continued

```
cgtgccacct tcttacagaa aagcttatat ggcaatgaaa tcatatgagg atgattaaat  35880
gaaaagtatc gctactgctg gccttgtcat tatatctgtt tttagtcttt ctggatgttt  35940
tgaagaaaca aaatcggttg attggtggct tgcacatccg aaggagacat acaaaaaatt  36000
tgaagagtgt cagaagtctg gtagcgattc tgataattgt aagaacgtta agcgagcaca  36060
tttgtctttt gaacggagaa aggcggttgg tttaccaata aattgagggt gatgtatggg  36120
gattgtcact ggtataccgg atggtactga tttatcaggt aatgtaacct ctcccgcaaa  36180
tgcgggaggt gtttctggat ttgattctga tttttttcag acaactcatg aagttatatt  36240
taatattctc aacaagagta tatctggaaa attaagtgaa tattcagatg tggcttatac  36300
tcttggtaaa tatggagttt ctctgtatgt tttatggtat gcttttactg tattagcaag  36360
gaaacaacag acacctgtac ctgattttat ctggaatatc tgtaggtttt acataatatt  36420
gctttttgtt aagaatacag gggaatact tacatcagca acagatgcta ttgatggatt  36480
gaaaaataca ttggcagggg gagatccgtg ggtatggatg gatcagttat gggtgaaggt  36540
tatacaagtt gcaactctta tttttgataa agatacatct actgtgcctg ttgccggtgg  36600
gattggtgct ttattaactt atgtcggtgg tgttttggca ttattgcttt gttctatagt  36660
atttgcatct gctgaattaa cattactatt actttctgtc actgcgccaa tatttatcat  36720
gtgtctgatg tttggtttac ttcggcaaat gtttaatagc tggctacagc ttaattttag  36780
ctcgttactg gtttttctat ttgcagcatt agcactaaga gctgggacat ggcaattaaa  36840
catggcatta agtacgtcta ttgctacagc atcagaaaac aatcttcttc aaacgggagt  36900
aacttcatta gctgctggca ttttcatggc ctggattatc tggcaggcga aaagttatgc  36960
ttcacagatt gcaggtgtgg gtgttgaagg tgccatgcag ggcgcagccg ctatggggat  37020
tggtgctggc gttttcggtg catcccgtat ggcgcgtggc gcacttggta tgggcagaaa  37080
tgccggtatt ggtgcatgga aaggtctgcg tcgtcaggaa gacgggtttg gtcagtctcc  37140
gggaataacg ggtaagaccg ctaacctggc cggacagggc gttaatattg gtgccaaaaa  37200
gcttcgtcag gcagctattg agagagcaaa gaaaatgtat ggtgggtaat ttaattatga  37260
gcgcctttta atgttctttt cataattgtc attgtcgggc ctggcgcgct ctattatctt  37320
ttctgttcac actgagtctt ctgtaaatat taatctgtta tacaggtgtt catattatga  37380
aactacttat tgtggctttc gtgacgcttt gtctcgctgg ttgtcaggcg tcacataaac  37440
taccgcccgt ttccgggaaa agcgaacctg ttaattctgc tgaggtaatg caaaatggaa  37500
tttaaacttc ccggatttaa aaataaaaaa gacgttactg actcatcagt ttcatttgaa  37560
gaaaaaaaca ttgcactaca ggagagaatg aatcgtattt ataaattcgg tggtatcgga  37620
ggcatgttaa ttggtgggct gtctttactt gcattaaatg cagcattacc actgaaaaca  37680
acagttgttg atgcctacct tatcgataag gttacaggtg tggctgaacg tctgacttct  37740
gttaaaaaag aaaatctttc tgaaaacgaa gccattgccc gatattttat cacccagtat  37800
ataaaacatc gtgaaggtta taattttttc agtctccagc atgattatga ttatgtaatg  37860
gcttacagcg cggagaatgt cgcggcagat tataacgcat tatttaacag tgaacaggca  37920
ccaaaacttg tttataacaa agcagaaaaa acggcaatgg ttcaggataa tccatctgtc  37980
ataatttcac cttcgtcacg ggcagatgat aaagatatcg gtgcgtatat tcgttttcgt  38040
ctgaccatca gggatgttgc taccggacaa acccgccagg agttctggaa tgttcgcctg  38100
acttatcgta tcgaaccgca ggttgaaatg gtgtcagggg aacgtaataa caatcctctt  38160
aaattcgttg taacaagcta cgttcgcgat aaagaagcca gaggttaata atatgaaaat  38220
```

```
gaataaagga gcgttaatta tggcgcttct gatggcggcg cacgtctgtc atgcagctgt  38280
tcttccttca ggcagtcgct ttgacccacg caatcagata gtcagttata accccaataa  38340
taccaccata attaacagtg ccgttggata caccaccaca ctggtatttg atgaagatga  38400
aacagttatc agtgccagaa ctggttttcc gcagggatgg gcggttaata aagaagataa  38460
cctggtatac ctggaagttc gtcctgttaa acagactgtt cagaaaaata atatggatga  38520
aaacggtaat acctcttctg aatccgtcag tgttgctctt gacccggaaa atgagcttga  38580
acgctggcga acgaatttgt ttgttcgcac cacgaagcgt aattacagca tggagctgaa  38640
cgcccggacg ttccggcagc cggagaaaat tgcgtttgtg gtgaattacc agtatccgca  38700
ggaacgccgg aaggaacagg ccgaaattga gaagaaacgc acagaggctc ttgccagacg  38760
ccaggaggag caggcaatca accgttccct ggaaaatgcg aaatcgcccc gtaactggca  38820
gtactggaag cgggttgctg aaggcagcca ggatatcagc cctgattatg catatgacga  38880
tggccgttat acctggttcg gcttcagtcc gttaaagaaa attcccagcg tctttgtgat  38940
gaacggtatg caggagactc ttaccaatcc tgtgattaaa cagagcggga gttttacggc  39000
tgttggcgta ccggttgata agcgttttgt tttacgtctt ggtgagcagg tggtggggat  39060
tgagaaccag ggcttcggaa aagtacgttt accagccgga gatacggtat ccccggatgt  39120
taagaaagag gtgatccagt gactgaacag gaaaataaaa tcccgactgc aaccgaaatt  39180
gaacagcagc tacgggaacg cagacagaaa gaactggaac aggccgggaa gactccggaa  39240
gaagagcctg gcaagccagc attgcagctt ggtattgaaa aacttaaaaa gtcacgtaaa  39300
gggatgatta tcctcgtcgt gggttttctt ctgcttgctg ccggtgtttc tgtttattat  39360
atcccgtcca ttatccgttc tgtgtcgtca ggggatgaga aacccgcaag tcagccgctt  39420
gcaaccggaa cggctaaacg tcagaccgga ctgagcgaag atatcgatcc ttttaatacc  39480
gcacagaaaa aaacagagaa accagaggaa gaaaaagtca tttcttctga aaagactgaa  39540
ccgccggaaa ataaacagca gagcttcagc cgtgcacttg acgtttctct tgatggcagc  39600
cagacaggaa acagcagcag ttcagcggga acgtcagttt cacatactgc ggccagtgag  39660
ccagaaagcg ataaaaagga tgaagcaaaa gcaaccgcac agactacaga atctgcgcca  39720
ctggcgaaaa taacgaaact tccatatgac ccaaatttgt ttatcccgga agggacatca  39780
attccctgtt cactggacag gcgttttgtt tctgacctgg cggggaaact ggaatgtacg  39840
gtcaacagcg atatatacag cgccagcggt aatgtaaaac ttatcgaaag aggaaccgcc  39900
gcaaaactga tgtataaggc cgggtcttta aatcatggac aagggcgtgt gtttgttatg  39960
gcttacaagc tacgtacccg cagtaagcct tttattgata ttcccctggt tgactcacag  40020
gcggctggcg cgttaggcga agccggtgct tctgggtgga ttgacactca tttcagtgaa  40080
cgttttcttg gtgcaatgat ggtcgggatg ataccggatt taagtcaggc cgccagtggt  40140
attgcacaga acaacaggga cagccagacc gactatacgg caaacagtcg ccaggctttt  40200
gctgatatag cacgcgaagc attttctaat agtgtgaata ttccgccaac gctttataaa  40260
aatcagggcg aaattattac tctgattgtc ggtcaggatc tggatttttc aggcatttat  40320
aaactgaaaa tgaaaggggg ttaatgtgaa taacgaaaac agacatctga tttatgatgt  40380
ggtcaacgat tatttttatc actggctgaa tgagattgag ggtgtcacgg aaattgctgt  40440
taaccgacca ggagaaatat ttataaaggt caggggaaag tggcaatggt atgaacaaaa  40500
gatgagttac agtgattgtc tttcttttgc atccacactg gccgattttc atgacggcgg  40560
ttctgtgact cctgaatatc ccctgcgctc tgccacgctt ccgggtggag aacgtgttca  40620
```

-continued

```
ggttgtgatc ccaccggcaa ctgaaaaaga cactgtttct ataacaatcc gtaagccgtc  40680
aggtattttt atcagtcatg acaaatttat aaaacaggga ttttattcac gcgtcagtgg  40740
tttaagtggt gactcggtta tggaagataa tatttctgct ttaatcactt ccggatattt  40800
tgatcgggtt atacctgaat cactgcgtca ggggaaaacg atagttttct gtggagggac  40860
gggttcaggt aaaactacct ttgcaaatgc ctgtctggaa tatataccgc atcatctgcg  40920
gtgtatttct attgaagata ctgatgaggc aaaattcaga ttccataaaa accatgtaaa  40980
actttactat ccggcagagg gtgagagtaa ggttattacc tcagcgagtc ttctgcgttc  41040
ctgttttcgt atgaatccgg acaggattct gatgacagaa atcagggggg ctgaggcatg  41100
ggattttctg aaagcatcga gttcaggcca tgcaggaaac attaccaccg ttcacgaaag  41160
tagtcctgaa tatgctgtgc ttgggattgt tcagcgatgt tatatgaatc ctgaatgtca  41220
gaatctacca ttcaatgtca ttttaagacg tgtactgagt aatattgata ttatcatgag  41280
tattaaatac cttgatgatg aagattttcg tttcgcttcc ggtatttatt acaaacaact  41340
tcattttgat gactatttca gaaaactgaa ggagtgatta tgtctttaaa actccccgat  41400
aaaggccagt gggtttttat cggtctggtt atgtgtctcg tgacatatta tactggttct  41460
gttgctgttt acttcctgaa cggaaaaacg ccgctttata tatggaaaaa ttttgattcc  41520
atgctcctgt ggcgaataat aacagagagt aatatacgga cagatatcag gttaaccgct  41580
atcccctctc ttttatcagg tatggtttcg tctctcatcg tgcctgtttt tattatctgg  41640
caactgaata aaacggctgt tgctctttat ggtgacgcga agtttgccag tgataatgat  41700
ttaaggaaat cgaaacttct gaaatgggag aaagaaaacg atactgatat tctcgtcgga  41760
gcatataaag gtaaatacct gtggtatacc gcaccagatt ttgtatcact tggcgcagga  41820
acccgcgcag gtaaaggtgc cgccattggt atccctaatc ttctggtcag aaaacactct  41880
ctgattgcgt tagatccaaa acaggaattg tggaaaatca ccagtaaggt gcgtgaaata  41940
ctgctgggta ataaagttta tctgctcgac cctttcaaca gtaaaacaca ccagtttaat  42000
ccccttttct atattgattt aaaagcggag agtggggcta aggatctgct taaactgatt  42060
gaaattctgt ttccgtctta tggcatgaca ggggcagaag cgcactttaa taatcttgcg  42120
ggtcaatact ggacaggact ggctaagttg cttcatttct ttattaacta tgagccgtcc  42180
tggcttaatg agttcgggct taaacccgtt ttctcaatcg gttctgtcgt cgacttgtac  42240
agcaatattg accgggaact gatactcagt aagcgggaag aactggaggg aacaaacggg  42300
cttgatgaaa acgcgttgta tcatttgcgc gatgccctga ccaaaatcag ggaatatcac  42360
gaaacggaag atgaacagcg ttcaagcatt gatggttctt tccgtaagaa aatgagcctg  42420
ttttatctcc caaccgttcg taaatgtact gatggtaatg atttcgatct ccgtcagttg  42480
cgacgggaag atatcactgt ttatgtcggt gttaatgcgg aagatatatc actggcttac  42540
gattttctga acctgttttt caacttcgtt gttgaagtga cattgcgtga aaatcctgat  42600
tttgatccca ccctgaaaca tgactgcctg atgtttcttg atgagttccc ttcgattggt  42660
tatatgccaa ttattaaaaa gggatcaggg tatattgcag gttttaaact taaactgctg  42720
acaatttatc agaatatcag tcagctaaat gaaatctatg gtattgaggg agccaaaacg  42780
ctgatgagtg ctcatccctg ccgtattatc tatgctgtca gcgaagagga tgatgccgcg  42840
aagatatcag aaaaacttgg gtatattacc actacatcaa agagcacaag caagaaccgg  42900
ggacgatcaa cttcacaggg cgaatcagaa agtgaagccc gaagagcact ggtgcttcca  42960
caggaactgg gaacgctgga ctttaaagaa gagtttatca tcctgaaggg ggagaaccct  43020
```

```
gttaaagcag aaaaggcact ttattacctt gatccgtatt ttatggacag gttaatgaag  43080
gtcagtccta aactggcatc attgacgatg aaactaaata agacgaaaaa aatatttggt  43140
gtgaaagggc ttaaatatcc gtcaaaagaa aaaatgctct ccgtaggaga gctggagtct  43200
gaggttttgc tatgaaaaaa atacttatga tcagtattct tgtcctcaca gcctgttcct  43260
ctccacctga accgccacag gttgaatggg aaaaaaggcc tgaagttatg aatacacaaa  43320
taatgaactg gaaaccaaca tccggtgtta ttaaatcaaa taatataaat tcctcatgga  43380
gtaaggtgtt gcctgatttt aaaccagaaa accatcttta cgatgattct gttttttatg  43440
ccgttgccca ttctgaaaaa atagttgtaa ggacatcttc ttttgatagt tactggtcag  43500
cgaaagactg gctaagaaaa aatggtgcaa caggtgttat tgaatatcag ccactaaaaa  43560
gatggttgaa taatgactat gttgaaattt atctgtcaag aataaatatt cagaggttac  43620
tatgaaaagg atatgcaaag gtctaatcgt aatttttact gtgtcctgtt ttatagcgcc  43680
aacgtatgcc gctgatccct gtaaatccgt tttttgtctt tatggtaaag ctgtcggtag  43740
tagtggaggg agtgagtgca gcagtgcaga aaaggatttt tttaaaaatg ttgaaaagaa  43800
aaaggggaaa atccgctggg gtaaaacatt tgatctccgt aagaattttt taaatcagtg  43860
ttcaacggca gacccggctg caatctcact gatcatgagt aagtttggtc gcgtcagagg  43920
ttgattaaaa cctgataccc gcgccaacgg gtatcagggg actgcaagta tcacataccg  43980
cgccaacgaa atgtgatgat tagttacaat cactgaggtt agaaatgaaa gtaaccaaat  44040
ctattatatc tattttattg tgcttatctg ctggtagtgc ataagtggat gtaataaaaa  44100
atgctcgtac ctttttgaaa ggaacccttg atctgagcgt gcaggaagca gatgaaaggg  44160
aagaacttta taagaagaac ggggcgcaac ctgactattt aagttacctg gaggattaac  44220
acatgcaata tgcattattt gatgggatgg aacgaaagtt tttgctggat gctcttgaat  44280
ttggtgttct gaaggactgg aaagaaaatc cggtaaaaga acttcctgat attgatgaat  44340
ctgttcaccc cttccatgtc tgttatggtg gatatttatt aaaccctgat gtttcagatt  44400
tagatattag cagaaaaata aaagaccaga caggattctg gctggcagct attgatgata  44460
cccgtatgga ttgtcattca atagcttatt atgatattca caccctccct ttaatttcgt  44520
gtggtcatca gaagatagtt ccttttgcag cgttaataaa agctgatgaa tgcatcattt  44580
caaaaattgc ttcgtattct ggttttgccg taacagcctt tttgagaatt aaagaccaga  44640
atatcgcaac gaatatactt aaccgtgagg gaatttttgc ctttaatggc tgtgagcaca  44700
gattcagaca acctgtaagt gaagataact ggcaacaggc agtgtcagaa gaacgcgcta  44760
tccgttgtgc caaaagatta attcaatgta aaggataaca aaatgagact ttttatcgct  44820
gaaaaacccg cagtagcaaa tgatattgtt aaggcacttg gtggcaattt tacccgccat  44880
gatggctggt ttgaaagtga taacgccatt gtgactaact gttttggtca tattatcgaa  44940
tcacaaccgc cggaaaacta taatcctgaa tacaaagcct ggaaggttga aacgcttcct  45000
ttacgtcttt atcccgtgaa gtatcagcct gttgaaagtg cagcaaaaca ggttaaaacg  45060
attctcgaac ttatcagacg tggagacgtg actgaaattg ttcacgctgg cgatcctgat  45120
gatgagggac agctacttgt tgatgaagtc ctggaatatg caggaaacac aaaacccgta  45180
aagcgcgttc tgataaacga caacacgctt ccggcagtga aaaaggcact ggcaaatctt  45240
aaagataatc gtgatttcaa agggctttac cttaaggcgc tggcgcgttc agttgccgat  45300
gccgtctatg gattctccat gacgcgtgct tacaccattc ctgcaaaagc cagaggatat  45360
cagggcgttc tgtctgtcgg gcgcgtccag acacccgttc ttggcctgat tgtgaatcgt  45420
```

acccgtgcta accagaacca taaatccagt ttttactaca ccatgaccgg agtttttcag 45480
cgtggtgctg atgttctcag ggcgaactgg aaaccaggtg aatttgctcc gctgaccgac 45540
cgtaaattac ttgataaggc gtgggcagac ggaacggcag catcccttgc aggaaaaccg 45600
gctacagttg aagcagcagc aactgatgat aaaaaaacgg ctgcgccgtt gccgtttaac 45660
ctggtcagac tccagcaata catgaacaag aagtttaaaa tgacggcaca aaaaacgctg 45720
gatattacgc aacaactacg tgaaaaatat aaagcaatta cttataaccg ctcagattgc 45780
tcatatcttt ctgatgaaca attcagtgaa gcgccgcagg ttatcgatgc cctgaaatca 45840
gtctttcctc agtcgctgga tattgattct tcacgtaaaa gcaaagcgtt taacagtgca 45900
aaggtgactg cgcatactgc gataatcccg acctccagtg tgcctgatgt taacgcactc 45960
agcaccgacg agcgcaatgt ttacctggcg atcgcacaac actatcttgt tcagttcatg 46020
cctgaaaaag cataccagga agtatcggtt gccattcagt gtggtgatga gtcgttctat 46080
gcccgtgcca gaaaaacaac tgacagcgga tttgaggcgt ttcttggcgc ggaaatcaca 46140
gacgaaggtg aatcagaaga taatgatgat tccgcttttg aactgctctg taaaattcgc 46200
acaggagaaa cactgacgac aaaagaagtt gttgttaatg agaagaaaac aacaccgctg 46260
ccgttattca ccgaagcctc cttgcttgct gcgcttgttc gtgtcgcgga ttt 46313

<210> SEQ ID NO 2
<211> LENGTH: 32950
<212> TYPE: DNA
<213> ORGANISM: SALMONELLA ENTERICA SEROTYPE ENTERITIDIS

<400> SEQUENCE: 2
aaccaagaca accacacata aaaacaatat gctcactttt taaccactgc gcgtaattgc 60
ctgatgttat ccttgtgctg ttccgcttcc tcgctcacta actcgctacg ctcggtcgtt 120
cggctgcggc gagcggtgtc tcctttctca aaaccagaag agttcagatc atacgatccg 180
ttgattgatc ctttttggat ctttcactga gaagccctga atcgctttct gtcgcttcgt 240
tcgatacaac catggtgaaa ccatgcgaaa tcgaaaaaat cgctcagaat gcgatacagc 300
gcgttttaga gggtatttac aaaacagtcg ttgccttgag gaaattttga tcaagattga 360
actcctatcc ggatcatggc aacagatcac agcaacaagg ccgctaaaaa gcgttgagcg 420
gcgttaaaca ccgtcaaacc gtagccgact acaacgaaac gggaaaaacg ctcagaacgc 480
gttacagagc gttttaaggc gatgtcggaa agagccatat ctcacctgtt ctgatgtttt 540
tctcaacatg agcactttta agagtgcttt taaagatgct attatgccaa tgagacaagc 600
ggagggctta tgagctatca aattctgaca accacagcgg ccagtattac tgacctgaaa 660
aaaaatccta tgggaaccgt agctgaaggt gaaggggacg ctgttgcgat cctgaaccga 720
aacgaaccgg cgttctattg cgttccacca aaactttacg cctactatcg ggaactcgct 780
gaagatgctg agttaaacgc tgttgctgat gagcgcatga aaaacccgga aattgtgaag 840
gttaacctgg atgacctatg aactggcttt tgaccgtaga gcactgaagg aatggcagaa 900
actcggccac accatccgtg aacaattcaa aaagaaactg gcagaacggc tggaaaatcc 960
acgcgtaccc gcagcccggt tacatggtca tgctgatcgc tataaaatca aacttcgtgc 1020
atctggctac agacttgtat atcaagtcat tgatgagaaa gtcgttttac ttgttatttc 1080
cgttggaaga agggaaagca gcgaagtcta tcagatcgca gatttgcgct aagattaatc 1140
atcaaaggat taactgttta ctgtcagaac aagagcatta aaaatttgcc acacctgcaa 1200
atgcaggtat aataaaacac aagaaaggga aacaggttct ctttcatcca gagcccaaag 1260

```
tgggcgggag gttaaaaatg caaaactacg ctaagtctgt agccacagag attttacgtc   1320
aacttggtgg taatcgtttt attgttatga ctggtgctaa aagtttttct tactttgatg   1380
aaaacggtga gtgcgggtta actttccgtt tgccgtccaa ttttgcaatg aaaggcatca   1440
acttagtaaa aattaaactg gattttactg atacgtacca ggtgaaattt tctcgtgtac   1500
ggggtgatga agttaaagat atttcaagat tcgataatat ctattgtgat cagttagcgt   1560
gtttatttac acaagaaaca gggttacata ccgtgttata gataaaaagg ggcattaagc   1620
ccctttttta gttattatga ggaataatat ggataaagat aagataatta agaaaaacag   1680
aggtaattac tcatatgtaa tcagaacgat ggatgaagat ggggatgcgg tttttcacgt   1740
cttaaaatat gttaagacga ttgataaaac taaaagcagg aaaacagtaa gaaaattgat   1800
aatggacgaa aaactcaacc tggcatcatt gatgcttctg gataatggga ttttgtgtga   1860
ttgtctgaca aaaggggatg aaaatgcaga ataaacctac acctgaagaa gtaaagaatg   1920
cacgggttgc ggcaggtctt actcttaaag aagctgctga tatttttggt tatcaactga   1980
attcctggca gatgaaagaa agtgcaggta aggccagtcg ttctttatct gttggtgaat   2040
atcagtattt attgctatta gcaaatatgc atccgtctta caggctggta aaaaaataac   2100
ttgctatacc tgcaaatgca ggtataataa aacacaagaa agggaaacag gttctctttc   2160
atccagagcc caagctgggc gggagctaaa aatgaaagta ttaactttta aaaatgatac   2220
tgtctctgtt ggtgatgtct ttgtatcatc ctggggctat gagcaaacca atgtaacctt   2280
ctaccaggtt ctttctgttc acggtaaaaa aaccgtcacc gttcgcgaga ttcgcgctaa   2340
ttcagaatat accgattcaa tggtcggctt taaaactccc gttttaaatg attttactgg   2400
tgaatgtttt aagcgccaga taaaagattt tggtgatgag ctggcaatca aaatcgaaga   2460
ttttgaaact gcgtataaaa ctctaccgga agaaaaacat cgattttctt cttactactg   2520
attaatcagg gggatattcc cccttttagt aaaggtctga aaatggaaag agagtttagc   2580
gcaaaagcat cattaaaccg aaatataaaa ttttggtttg agcaatgtgg gttatctaaa   2640
gaaagagtta ttcgttgtat tgataactgg tatgaccttg catacccacc atcagaacag   2700
gagaaagcaa aaaaagaagc aattgagaag ttaataaagt aaagataaag atggtatcag   2760
gttgtggggc aacctgatac cgtgacacct gattctattg cgaggaataa aatgtcggaa   2820
cgcatattat cagcaataaa tgacgttgaa aagggtgggc gtccggtttt ccctttgatg   2880
ccattccatg tctttcctga gtatatggca ttactcagaa aagcactgga aaaaaagaca   2940
caaaagagaa cagataaata aaccggaggc tttatgacaa aacatgattt tgtgtccttt   3000
gtcagtggag aattgcggca aggcgctgta cgcttttctc ttgcttttaa cagcaaagga   3060
gaaattgttc tgcactggac taataaagca ggaatacgag tatggcggat attaagtggt   3120
aatcgtggca aaaaaccaag caaagctaac cttgaaagaa tgagtaactt ccggcgctgg   3180
ctttttgatg cccgtcaggg catggaaggc tacactcagc aacctgaaca gagcaacctt   3240
agctgaatag ccgaagccct cccgtatttc gggaggtgct ttctgatata ttgcgcggga   3300
ctgcgcttgc gcttcctgcc agaccgttcg cggagcgaac ctgacggcac tgtccttacc   3360
gcattgatcg ggtttccggt cgcagacgta cgtatgttca gccatgacaa catcagcctt   3420
tttgcatttt tgttgatgct caagcacaat ttatgagcgg tgccagattc actgcgatgc   3480
aggatagggc aaacgccgca aaatgacgtc tctgacgcca ttccgcaacg tttgcccggt   3540
gacctacagt cggttattgt cggagaattt tatgaaaaaa gttcaattca gaattgatga   3600
aaatcagcat aatgatttgc tggattgtct taaaactctt tatccagatg aaccagcttt   3660
```

```
aacagtagct aaaggcatga aacttttagc aaatgcttta ttaaaaagta aagctggcag   3720
taaggacata aatacgtttt ttgataataa tgattttatc aaaacaacga tgtacttaac   3780
aggtaaacaa agggctgata ttgaaagagc tgctaatcgt cacggatgga cgttatcacg   3840
agaatgtcgt taccgcatac agacgacact tgaaaatgaa ctggatttct ttgaccagga   3900
actgctgatg atgaatcgtt gccgtaattc aattgataag atcggtcgta atttccatta   3960
tatcattgtt aatgatcaga ccagggttct tgataaagat ggtttctatc aggatgcgga   4020
gcgtcttaca acagaaattt ttaatcttaa gaatcagttt gagaattaca ttatgttatg   4080
taaagggaga actgtttcaa ataaagtgga gatgtaatta tgggcgttta cgttgataaa   4140
gaatatcgtg ttaaacgaaa gtcatcagaa aatggtcgta agtcagcttt cgctcacaaa   4200
gtcaaaaatg gtggaaagaa ctatagccgc aatgttcagg aacgtatcaa ccgcaagggt   4260
gccagtaagg aggttgttgt caaaatatct ggaggtgctg ttactcgtca ggggattcgg   4320
aacagtattg attatatgag ccgtgagtca gagctaccag tgatgagtga aagcggtcgg   4380
gtatggatgg gtgccgaaat tctggaggct aaagagcaca tgatagatcg tgctaatgat   4440
cctcagcatg tgatgaatga taaaggtaaa gaaaataaaa aatcacacaa gaatattgtc   4500
ttctcgcctc cagttttagc gaaagtaaag cctgaagatt tgttggagtc tgtcaggaaa   4560
acgatgcaga aaaaatatcc taatcaccgt tttgttcttg gataccactg tgacaagaaa   4620
gaacatcctc acgttcatgt tgtttttcgt atccgagata atgacggtaa acgcgctgat   4680
atcaggaaaa aagatttacg ggaaattcgt acaggttttt gtgaagagtt gaagttaaaa   4740
ggttatgacg ttaaagcgac ccataagcaa cagcatggac ttaatcagtc tgttaaagat   4800
gcacataata cagcaccaaa aagacagaaa ggtgtttatg aggttgttga tattggctat   4860
gaccattatc agaacgataa aacaaagtct aagcaacatt ttataaagct aaagactctt   4920
aacaaggggg ttgagaaaac atactggggg gctgattttg gggacttatg ttcgcgggaa   4980
agtgttaaag caggtgatct tgtcaggctg aagaaacttg gtcagaaaga agtaaaaatc   5040
ccggcgctcg ataaaaacgg tgttcagcat ggctggaaaa cggttcacag aaatgagtgg   5100
cagttagaaa atctgggggt taagggcgta gacagaacac cttcagccag caaagagctg   5160
gtacttaaca gccctgatat gctgctgaag caacaacagc gaatggcgca gtttacgcag   5220
cagaaagcat ccacgttaca gtcagaacag aagctgaaaa cagggattaa gtttttgggc   5280
ttataagatt taatgtattg attatgcgag aaaaatattt attttagttc gcttgctcat   5340
cttttcacct taaaaacaga tcgaaattct gcgttttagc tatcattcga tctatcgatc   5400
taaaaaacag atctgcaaaa gatgaatatt ctgtgtttca ttgcatacat ggaataaatg   5460
aaagtaaaat tgatttatca agatcgaaag atctgtttta tgtgttgaac ttagcataag   5520
ccacttgtag tataaacttc gcgcaatagt aaaaagtctc tcttcatagg ggcgtgattt   5580
ctcacaagca accacggttg gcttgtgttt tgtcacatct gtatatcggg gattgagtat   5640
gaaaggacag aaacagtttt acctgcttca gtgttctccg cattttcatc agtcggttct   5700
gttgcagtta tcccggagcg gtatcgctta ctacaatcca gttatacgca ctttctataa   5760
gaggcgtgac tgtagtgcat acaggggaca aatcatgcca atgtttcccg gttatgtatt   5820
cgttcttctg gattttgagg ttgtacatcc atcctgcttt acccggatga aaaatgttta   5880
tggactggtc agttttggtg aatatcctgc tgaagttcct ctgagtgtca taaatgaagt   5940
aaaagagcag gagaagattt tttcgatgaa tttaagcctg atgaataact cctgtctggc   6000
aaaaatactt ctccttgcag acgcttcaaa gcgtggacga gtctttgccg actatgtgtg   6060
```

-continued

```
taacagaaaa tacgacaggt taaaaaatga cagctataaa aggaaagcgg aaaccgcaac   6120
gcaatgtact ctaccttcct acagaagttc gtgttgaagt tgaaaaaatt gcaattgaaa   6180
taagcttcaa gagggggcga cgtatctctg attctggttt tgttcagtat cttattaaaa   6240
aatacaaatc tcaggcgatg aaagaactta ttcatggggc tgatattcct gacgagtaat   6300
attgtcccaa tgttctgaat gtggaatatt tatgttatct acttctactt ttcttgcgct   6360
tgccatgcaa tgcgctgcca gcgttcatcc cgacacaacg cacgaagtcg ccagggttga   6420
atcaggtttt aacccatatg cgattgcgga aataatacca aaggttaaac gtaaaactgg   6480
tgataaaggc gtagtatctt actttcctga atcaaaggag gcagcactta agatcgttaa   6540
aaacattgaa ttacggaatc atcgttactc tgtaggactt atgcaaataa cgagtaccaa   6600
ttttgcaaag ttcggtacaa cagcagagaa aatgtttgat ccatgcgaaa atcttaaggt   6660
atcagaaaaa atactggttg actgttataa acgaggtggc gacttagtgc gtgggctgag   6720
ttgctattat tctggcaatc aagaaacagg agtaaagcca gaacctgaat ttaataatac   6780
aagttatgta caacgtatag gatttagccc tcctgataat aaaaaaagtt ttattgttcc   6840
ctctgtaaag gaaatgatta aaaaggagaa taagacgact atcacacctg aagaaatcat   6900
tatatatcct caatacgcca tgcgtggcac tgtatcaaat gaaaaggaaa caaaagatgt   6960
tgaaattaaa tctgaataaa cgttatttaa cgctttctct atttatggct gcgttgatgc   7020
tttgtgttgc agaacctgct tttgcggatg atgtgtctac gaagacaact ggtttttttac   7080
agaaaataat tgattttttta acggatattc gtaaacctgc aattacaatt attgctcttg   7140
ttattgggta tattgcgata ttttctcgtc aacatacctc atggatagtc ccacttgtta   7200
tcggaattat catctttatt gttgcaccat atattcctga ctggcttgcg taattaaagg   7260
atgggcgcac tatgagtact ctttttaaag gtcttacgcg ccctgcttta ataagggggc   7320
tgggcgttcc gctctacccc tttcttggaa tgtgcattat ttgtgttctg cttggtgtct   7380
ggattcatga ggctatgtat gcccttattc ttcctggctg gtatgccatc aggcgtgtaa   7440
cacagtttga tgaacgcttt tttgaccttc tgtatctgag aactcttgtc aaagggcatc   7500
ctttatcaaa caagcgattc agcgcagtcc attatgcggg gagccagtac aatgaagttg   7560
atatttcaaa agtggataac tttatgaagc tgaaagacca gtcttctgtt gaagagttaa   7620
ttccgtactc ttcacatatc actgataata ttatcgttac aaaaaaccgg gatttgctgg   7680
caacctggca gatagacggt gcttactttg agtgtgttga ttctgaagat ttgtcaattc   7740
tgacagatca gcttaatacg cttatacgta gctttgaagg gaaatttgtt acgctttatc   7800
ctcatcgtat caggtgtaaa aagggcgtca gaccagtatt taacagtaaa attccttttg   7860
tgaacagagt aatgaatgat tattacgagt cattccctca gtctgaattt ttcgagaata   7920
aattatttct gacgatttgt tttaaacctt ttactacgga agataaagta acacatttct   7980
tttcacgcag taaaaaacaa aaagatatct ttaaagagcc tgttaatgaa atgaatgaaa   8040
tttgcgacag gttgaatacc tatctgtccc gttttcattc ccgacgtctt gggctttatg   8100
aagatcatgg ggttgtttat tcagatcagt tatctctgtt ccagtatctg ctttctggtc   8160
gatggcaaaa ggtcagggtt agcagtagtc cgttttatac atatctggga ggaaaagacc   8220
tgttctttgg taatgatgcc ggacaaatta ccgcgtcaga ccatgcccgg tattttcgtt   8280
gcatagagat taaggattat tttcaggaga cggatgccgg tattctggat gctctgatgt   8340
atctccccgt tgagtatgtc gtgacatcgt cctttactgc gatggataag cagtcagcga   8400
ttaaggcgct ggatgatcag atcgataagc tggaaatgac agatgatgct gccaaatctt   8460
```

-continued

```
tgctggcaga tctgaaagtc ggactggata tggtttccag tggatatatt tctttcggaa   8520

aatcgcatca gaccctggtt gtctttgcgg attcaccgga gcggctggtg aaagacacca   8580

atatcgtgac ttccactctg gaagatttgg ggctgattgt cacttattca acactgagtc   8640

ttggcgcagc ttattttgct cagctaccag gaaattatac gcttcgccct cgtctgagta   8700

ccctcagtag tcttaatttt gccgaaatgg aaagttttca taatttcttt tcaggaaaag   8760

aaaaaggaaa tacctggggg gaaaaactga ttactcttcg ggggtcaggt aatgatatct   8820

accatctgaa ttaccatatg acgactgaac atcagaattt cttcggtaag aacccgacgc   8880

tggggcatac cgaaattctc ggtacgtcta acgtgggtaa aaccgtatta ctgatgacaa   8940

aagcatttgc cgcccagcag ttcggtacgc cggaatcatt ccctgcaaac agaaaactga   9000

aaaaactgac cacggttttt tttgataaag accgggcagg tgaagtcggt atacgggcaa   9060

tggggggatc ttattaccgg gtgaaggagg gagagccgac aggctggaat cccgccgcac   9120

tgccgccaac aaagcgtaat atcgctttta tgaaggacct ggtgaggctg ctttgtactc   9180

tcaacagtga gccgctcgat gattaccaga acagcctgat ttcagatgcg gttgaacgtc   9240

ttatgcaacg gtcagatcgc tcttatcctg tcagtaaact acggcctctt atccaggagc   9300

cggatgatac tgaaaccaaa cgtcatggac ttaaagcccg tcttaagccg tggacgcagg   9360

gggaagagtt tggctgggtg ttcgacaatc gggaagacac gtttgatgtc gataacctgg   9420

atgttttcgg tattgatgga acggagttcc tggataataa ggtgctggcc agtgctgctt   9480

cattctatct catctatcgg gtcaccatgc tggccgatgg tcgcaggctt cttatctaca   9540

tggatgagtt ctggcaatgg atcaataacg aagcgttcag ggactttgtt tacaacaagc   9600

tgaaaaccgg acgtaaactc gatatggtgc ttgtcgtagc cacacagtca ccggatgaac   9660

tgattaaatc acccattgcg gcagcggttc gtgagcaatg cgccactcat atctatctgg   9720

caaacccgaa agccaaacgt agtgaatatg ttgatggttt gcaggtcagg gagctttatt   9780

ttgacaaaat taaagctatc gatccgctgt cccgccagtt ccttgttgtt aagaacccac   9840

agaggaaagg tgaaagtgat gattttgctg cttttgccag actggagctg ggaaaagcag   9900

cgtattactt accggttctc agtgcatcaa aaccccagtt agaactgttc gatgaaatct   9960

ggaaagaagg aatgaagccg gaagagtggc ttgataccta tctggaacag gcgaacctga  10020

tttgaggaat caccaatgaa aaagcaaatt atggcggcat tcgtcgcttc actgattgtt  10080

atttccggcg ctcaggcagg gatacctgtt gccatcgacg ccaaccctga atgggcgatt  10140

gaagccggac gatggacaga acgccttaag caatgggcgg aaacggtaaa acattacgaa  10200

aatcagataa atgcgtacaa acaggagctg ctgtcaaaaa cgggtatccg tgatgtgcag  10260

ggactggtgc agtccgcaca gtcagtgagt caggaactga tgcagattta tgatcagggg  10320

aatgctttta ttgacgatta cattaaaaat cctgaagggg cgttatcgga acaggccaaa  10380

tcgttattgt cagattacaa agtaacggat acctgccaga acctgggata ttccggcgac  10440

ctggtacggg gatgtgaagc gacgttcctt tctcaactgg caagcgtgga atacggtaac  10500

aagctggaga gcaagcttcg tcaggacaac cagacgatga aagaccttat tgatcaagtc  10560

aaaaatgcga aggatacgaa ggccacgcag gatgcaacaa acgctgttgc acttgaacaa  10620

ctgaagttcg agaagctcaa atttcagtat caaatgtatc gcgataagca gcgagatctt  10680

gcagaatata aagagaagat ggctcaggca gctttcagaa aacagcaacg tgaagccgtg  10740

ccaccttctt acagaaaagc ttatatggca atgaaatcat atgaggatga ttaaatgaaa  10800

agtatcgcta ctgctggcct tgtcattata tctgttttta gtctttctgg atgttttgaa  10860
```

```
gaaacaaaat cggttgattg gtggcttgca catccgaagg agacatacaa aaaatttgaa  10920

gagtgtcaga agtctggtag cgattctgat aattgtaaga acgttaagcg agcacatttg  10980

tcttttgaac ggagaaaggc ggttggttta ccaataaatt gagggtgatg tatggggatt  11040

gtcactggta taccggatgg tactgattta tcaggtaatg taacctctcc cgcaaatgcg  11100

ggaggtgttt ctggatttga ttctgatttt tttcagacaa ctcatgaagt tatatttaat  11160

attctcaaca agagtatatc tggaaaatta agtgaatatt cagatgtggc ttatactctt  11220

ggtaaatatg gagtttctct gtatgtttta tggtatgctt ttactgtatt agcaaggaaa  11280

caacagacac ctgtacctga ttttatctgg aatatctgta ggttttacat aatattgctt  11340

tttgttaaga atacaggggg aatacttaca tcagcaacag atgctattga tggattgaaa  11400

aatacattgg caggggggaga tccgtgggta tggatggatc agttatgggt gaaggttata  11460

caagttgcaa ctcttatttt tgataaagat acatctactg tgcctgttgc cggtgggatt  11520

ggtgctttat taacttatgt cggtggtgtt ttggcattat tgctttgttc tatagtattt  11580

gcatctgctg aattaacatt actattactt tctgtcactg cgccaatatt tatcatgtgt  11640

ctgatgtttg gtttacttcg gcaaatgttt aatagctggc tacagcttaa ttttagctcg  11700

ttactggttt ttctatttgc agcattagca ctaagagctg ggacatggca attaaacatg  11760

gcattaagta cgtctattgc tacagcatca gaaaacaatc ttcttcaaac gggagtaact  11820

tcattagctg ctggcatttt catggcctgg attatctggc aggcgaaaag ttatgcttca  11880

cagattgcag gtgtgggtgt tgaaggtgcc atgcagggcg cagccgctat ggggattggt  11940

gctggcgttt tcggtgcatc ccgtatggcg cgtggcgcac ttggtatggg cagaaatgcc  12000

ggtattggtg catggaaagg tctgcgtcgt caggaagacg ggtttggtca gtctccggga  12060

ataacgggta agaccgctaa cctggccgga cagggcgtta atattggtgc caaaaagctt  12120

cgtcaggcag ctattgagag agcaaagaaa atgtatggtg ggtaatttaa ttatgagcgc  12180

cttttaatgt tcttttcata attgtcattg tcgggcctgg cgcgctctat tatcttttct  12240

gttcacactg agtcttctgt aaatattaat ctgttataca ggtgttcata ttatgaaact  12300

acttattgtg gctttcgtga cgctttgtct cgctggttgt caggcgtcac ataaactacc  12360

gcccgtttcc gggaaaagcg aacctgttaa ttctgctgag gtaatgcaaa atggaattta  12420

aacttcccgg atttaaaaat aaaaaagacg ttactgactc atcagtttca tttgaagaaa  12480

aaaacattgc actacaggag agaatgaatc gtatttataa attcggtggt atcggaggca  12540

tgttaattgg tgggctgtct ttacttgcat taaatgcagc attaccactg aaaacaacag  12600

ttgttgatgc ctaccttatc gataaggtta caggtgtggc tgaacgtctg acttctgtta  12660

aaaaagaaaa tctttctgaa aacgaagcca ttgcccgata ttttatcacc cagtatataa  12720

aacatcgtga aggttataat tttttcagtc tccagcatga ttatgattat gtaatggctt  12780

acagcgcgga gaatgtcgcg gcagattata acgcattatt taacagtgaa caggcaccaa  12840

aacttgttta taacaaagca gaaaaaacgg caatggttca ggataatcca tctgtcataa  12900

tttcaccttc gtcacgggca gatgataaag atatcggtgc gtatattcgt tttcgtctga  12960

ccatcaggga tgttgctacc ggacaaaccc gccaggagtt ctggaatgtt cgcctgactt  13020

atcgtatcga accgcaggtt gaaatggtgt caggggaacg taataacaat cctcttaaat  13080

tcgttgtaac aagctacgtt cgcgataaag aagccagagg ttaataatat gaaaatgaat  13140

aaaggagcgt taattatggc gcttctgatg gcggcgcacg tctgtcatgc agctgttctt  13200

ccttcaggca gtcgctttga cccacgcaat cagatagtca gttataaccc caataatacc  13260
```

```
accataatta acagtgccgt tggatacacc accacactgg tatttgatga agatgaaaca  13320

gttatcagtg ccagaactgg ttttccgcag ggatgggcgg ttaataaaga agataacctg  13380

gtatacctgg aagttcgtcc tgttaaacag actgttcaga aaaataatat ggatgaaaac  13440

ggtaatacct cttctgaatc cgtcagtgtt gctcttgacc cggaaaatga gcttgaacgc  13500

tggcgaacga atttgtttgt tcgcaccacg aagcgtaatt acagcatgga gctgaacgcc  13560

cggacgttcc ggcagccgga gaaaattgcg tttgtggtga attaccagta tccgcaggaa  13620

cgccggaagg aacaggccga aattgagaag aaacgcacag aggctcttgc cagacgccag  13680

gaggagcagg caatcaaccg ttccctggaa aatgcgaaat cgccccgtaa ctggcagtac  13740

tggaagcggg ttgctgaagg cagccaggat atcagccctg attatgcata tgacgatggc  13800

cgttatacct ggttcggctt cagtccgtta aagaaaattc ccagcgtctt tgtgatgaac  13860

ggtatgcagg agactcttac caatcctgtg attaaacaga gcgggagttt tacggctgtt  13920

ggcgtaccgg ttgataagcg ttttgtttta cgtcttggtg agcaggtggt ggggattgag  13980

aaccagggct tcggaaaagt acgtttacca gccggagata cggtatcccc ggatgttaag  14040

aaagaggtga tccagtgact gaacaggaaa ataaaatccc gactgcaacc gaaattgaac  14100

agcagctacg ggaacgcaga cagaaagaac tggaacaggc cgggaagact ccggaagaag  14160

agcctggcaa gccagcattg cagcttggta ttgaaaaact taaaaagtca cgtaaaggga  14220

tgattatcct cgtcgtgggt tttcttctgc ttgctgccgg tgtttctgtt tattatatcc  14280

cgtccattat ccgttctgtg tcgtcagggg atgagaaacc cgcaagtcag ccgcttgcaa  14340

ccggaacggc taaacgtcag accggactga gcgaagatat cgatcctttt aataccgcac  14400

agaaaaaaac agagaaacca gaggaagaaa aagtcatttc ttctgaaaag actgaaccgc  14460

cggaaaataa acagcagagc ttcagccgtg cacttgacgt ttctcttgat ggcagccaga  14520

caggaaacag cagcagttca gcgggaacgt cagtttcaca tactgcggcc agtgagccag  14580

aaagcgataa aaaggatgaa gcaaaaagcaa ccgcacagac tacagaatct gcgccactgg  14640

cgaaaataac gaaacttcca tatgacccaa atttgtttat cccggaaggg acatcaattc  14700

cctgttcact ggacaggcgt tttgtttctg acctggcggg gaaactggaa tgtacggtca  14760

acagcgatat atacagcgcc agcggtaatg taaaacttat cgaaagagga accgccgcaa  14820

aactgatgta taaggccggg tctttaaatc atggacaagg gcgtgtgttt gttatggctt  14880

acaagctacg tacccgcagt aagcctttta ttgatattcc cctggttgac tcacaggcgg  14940

ctggcgcgtt aggcgaagcc ggtgcttctg ggtggattga cactcatttc agtgaacgtt  15000

ttcttggtgc aatgatggtc gggatgatac cggatttaag tcaggccgcc agtggtattg  15060

cacagaacaa cagggacagc cagaccgact atacggcaaa cagtcgccag gcttttgctg  15120

atatagcacg cgaagcattt tctaatagtg tgaatattcc gccaacgctt tataaaaatc  15180

agggcgaaat tattactctg attgtcggtc aggatctgga tttttcaggc atttataaac  15240

tgaaaatgaa agggggttaa tgtgaataac gaaaacagac atctgattta tgatgtggtc  15300

aacgattatt tttatcactg gctgaatgag attgagggtg tcacggaaat tgctgttaac  15360

cgaccaggag aaatatttat aaaggtcagg ggaaagtggc aatggtatga acaaaagatg  15420

agttacagtg attgtctttc ttttgcatcc acactggccg attttcatga cggcggttct  15480

gtgactcctg aatatcccct gcgctctgcc acgcttccgg gtggagaacg tgttcaggtt  15540

gtgatcccac cggcaactga aaaagacact gtttctataa caatccgtaa gccgtcaggt  15600

atttttatca gtcatgacaa atttataaaa cagggatttt attcacgcgt cagtggttta  15660
```

```
agtggtgact cggttatgga agataatatt tctgctttaa tcacttccgg atattttgat  15720
cgggttatac ctgaatcact gcgtcagggg aaaacgatag ttttctgtgg agggacgggt  15780
tcaggtaaaa ctacctttgc aaatgcctgt ctggaatata taccgcatca tctgcggtgt  15840
atttctattg aagatactga tgaggcaaaa ttcagattcc ataaaaacca tgtaaaactt  15900
tactatccgg cagagggtga gagtaaggtt attacctcag cgagtcttct gcgttcctgt  15960
tttcgtatga atccggacag gattctgatg acagaaatca ggggggctga ggcatgggat  16020
tttctgaaag catcgagttc aggccatgca ggaaacatta ccaccgttca cgaaagtagt  16080
cctgaatatg ctgtgcttgg gattgttcag cgatgttata tgaatcctga atgtcagaat  16140
ctaccattca atgtcatttt aagacgtgta ctgagtaata ttgatattat catgagtatt  16200
aaataccttg atgatgaaga ttttcgtttc gcttccggta tttattacaa acaacttcat  16260
tttgatgact atttcagaaa actgaaggag tgattatgtc tttaaaactc cccgataaag  16320
gccagtgggt ttttatcggt ctggttatgt gtctcgtgac atattatact ggttctgttg  16380
ctgtttactt cctgaacgga aaaacgccgc tttatatatg gaaaaatttt gattccatgc  16440
tcctgtggcg aataataaca gagagtaata tacggacaga tatcaggtta accgctatcc  16500
cctctctttt atcaggtatg gtttcgtctc tcatcgtgcc tgtttttatt atctggcaac  16560
tgaataaaac ggctgttgct ctttatggtg acgcgaagtt tgccagtgat aatgatttaa  16620
ggaaatcgaa acttctgaaa tgggagaaag aaaacgatac tgatattctc gtcggagcat  16680
ataaaggtaa atacctgtgg tataccgcac cagattttgt atcacttggc gcaggaaccc  16740
gcgcaggtaa aggtgccgcc attggtatcc ctaatcttct ggtcagaaaa cactctctga  16800
ttgcgttaga tccaaaacag gaattgtgga aatcaccag taaggtgcgt gaaatactgc  16860
tgggtaataa agtttatctg ctcgaccctt tcaacagtaa aacacaccag tttaatcccc  16920
ttttctatat tgatttaaaa gcggagagtg gggctaagga tctgcttaaa ctgattgaaa  16980
ttctgtttcc gtcttatggc atgacagggg cagaagcgca ctttaataat cttgcgggtc  17040
aatactggac aggactggct aagttgcttc atttctttat taactatgag ccgtcctggc  17100
ttaatgagtt cgggcttaaa cccgttttct caatcggttc tgtcgtcgac ttgtacagca  17160
atattgaccg ggaactgata ctcagtaagc gggaagaact ggagggaaca aacgggcttg  17220
atgaaaacgc gttgtatcat ttgcgcgatg ccctgaccaa aatcagggaa tatcacgaaa  17280
cggaagatga acagcgttca agcattgatg gttctttccg taagaaaatg agcctgtttt  17340
atctcccaac cgttcgtaaa tgtactgatg gtaatgattt cgatctccgt cagttgcgac  17400
gggaagatat cactgtttat gtcggtgtta atgcggaaga tatatcactg gcttacgatt  17460
ttctgaacct gtttttcaac ttcgttgttg aagtgacatt gcgtgaaaat cctgattttg  17520
atcccaccct gaaacatgac tgcctgatgt ttcttgatga gttcccttcg attggttata  17580
tgccaattat taaaaaggga tcagggtata ttgcaggttt taaacttaaa ctgctgacaa  17640
tttatcagaa tatcagtcag ctaaatgaaa tctatggtat tgagggagcc aaaacgctga  17700
tgagtgctca tccctgccgt attatctatg ctgtcagcga agaggatgat gccgcgaaga  17760
tatcagaaaa acttgggtat attaccacta catcaaagag cacaagcaag aaccggggac  17820
gatcaacttc acagggcgaa tcagaaagtg aagcccgaag agcactggtg cttccacagg  17880
aactgggaac gctggacttt aaagaagagt ttatcatcct gaagggggag aaccctgtta  17940
aagcagaaaa ggcactttat taccttgatc cgtattttat ggacaggtta atgaaggtca  18000
gtcctaaact ggcatcattg acgatgaaac taaataagac gaaaaaaata tttggtgtga  18060
```

```
aagggcttaa atatccgtca aaagaaaaaa tgctctccgt aggagagctg gagtctgagg  18120

ttttgctatg aaaaaaatac ttatgatcag tattcttgtc ctcacagcct gttcctctcc  18180

acctgaaccg ccacaggttg aatgggaaaa aaggcctgaa gttatgaata cacaaataat  18240

gaactggaaa ccaacatccg gtgttattaa atcaaataat ataaattcct catggagtaa  18300

ggtgttgcct gattttaaac cagaaaacca tctttacgat gattctgttt tttatgccgt  18360

tgcccattct gaaaaaatag ttgtaaggac atcttctttt gatagttact ggtcagcgaa  18420

agactggcta agaaaaaatg gtgcaacagg tgttattgaa tatcagccac taaaaagatg  18480

gttgaataat gactatgttg aaatttatct gtcaagaata aatattcaga ggttactatg  18540

aaaaggatat gcaaaggtct aatcgtaatt tttactgtgt cctgttttat agcgccaacg  18600

tatgccgctg atccctgtaa atccgttttt tgtctttatg gtaaagctgt cggtagtagt  18660

ggagggagtg agtgcagcag tgcagaaaag gattttttta aaaatgttga aaagaaaaag  18720

gggaaaatcc gctggggtaa aacatttgat ctccgtaaga attttttaaa tcagtgttca  18780

acggcagacc cggctgcaat ctcactgatc atgagtaagt ttggtcgcgt cagaggttga  18840

ttaaaacctg atacccgcgc caacgggtat caggggactg caagtatcac ataccgcgcc  18900

aacgaaatgt gatgattagt tacaatcact gaggttagaa atgaaagtaa ccaaatctat  18960

tatatctatt ttattgtgct tatctgctgg tagtgcataa gtggatgtaa taaaaaatgc  19020

tcgtaccttt ttgaaaggaa cccttgatct gagcgtgcag gaagcagatg aaagggaaga  19080

actttataag aagaacgggg cgcaacctga ctatttaagt tacctggagg attaacacat  19140

gcaatatgca ttatttgatg ggatggaacg aaagtttttg ctggatgctc ttgaatttgg  19200

tgttctgaag gactggaaag aaaatccggt aaaagaactt cctgatattg atgaatctgt  19260

tcaccccttc catgtctgtt atggtggata tttattaaac cctgatgttt cagatttaga  19320

tattagcaga aaaataaaag accagacagg attctggctg gcagctattg atgatacccg  19380

tatggattgt cattcaatag cttattatga tattcacacc ctccctttaa tttcgtgtgg  19440

tcatcagaag atagttcctt ttgcagcgtt aataaaagct gatgaatgca tcatttcaaa  19500

aattgcttcg tattctggtt ttgccgtaac agccttttg agaattaaag accagaatat  19560

cgcaacgaat atacttaacc gtgagggaat tttgcctttt aatggctgtg agcacagatt  19620

cagacaacct gtaagtgaag ataactggca acaggcagtg tcagaagaac gcgctatccg  19680

ttgtgccaaa agattaattc aatgtaaagg ataacaaaat gagacttttt atcgctgaaa  19740

aacccgcagt agcaaatgat attgttaagg cacttggtgg caattttacc cgccatgatg  19800

gctggtttga aagtgataac gccattgtga ctaactgttt tggtcatatt atcgaatcac  19860

aaccgccgga aaactataat cctgaataca aagcctggaa ggttgaaacg cttcctttac  19920

gtctttatcc cgtgaagtat cagcctgttg aaagtgcagc aaaacaggtt aaaacgattc  19980

tcgaacttat cagacgtgga gacgtgactg aaattgttca cgctggcgat cctgatgatg  20040

agggacagct acttgttgat gaagtcctgg aatatgcagg aaacacaaaa cccgtaaagc  20100

gcgttctgat aaacgacaac acgcttccgg cagtgaaaaa ggcactggca aatcttaaag  20160

ataatcgtga tttcaaaggg ctttacctta aggcgctggc gcgttcagtt gccgatgccg  20220

tctatggatt ctccatgacg cgtgcttaca ccattcctgc aaaagccaga ggatatcagg  20280

gcgttctgtc tgtcgggcgc gtccagacac ccgttcttgg cctgattgtg aatcgtaccc  20340

gtgctaacca gaaccataaa tccagttttt actacaccat gaccggagtt tttcagcgtg  20400

gtgctgatgt tctcagggcg aactggaaac caggtgaatt tgctccgctg accgaccgta  20460
```

```
aattacttga taaggcgtgg gcagacggaa cggcagcatc ccttgcagga aaaccggcta  20520
cagttgaagc agcagcaact gatgataaaa aaacggctgc gccgttgccg tttaacctgg  20580
tcagactcca gcaatacatg aacaagaagt ttaaaatgac ggcacaaaaa acgctggata  20640
ttacgcaaca actacgtgaa aaatataaag caattactta taaccgctca gattgctcat  20700
atctttctga tgaacaattc agtgaagcgc cgcaggttat cgatgccctg aaatcagtct  20760
ttcctcagtc gctggatatt gattcttcac gtaaaagcaa agcgtttaac agtgcaaagg  20820
tgactgcgca tactgcgata atcccgacct ccagtgtgcc tgatgttaac gcactcagca  20880
ccgacgagcg caatgtttac ctggcgatcg cacaacacta tcttgttcag ttcatgcctg  20940
aaaaagcata ccaggaagta tcggttgcca ttcagtgtgg tgatgagtcg ttctatgccc  21000
gtgccagaaa aacaactgac agcggatttg aggcgtttct tggcgcggaa atcacagacg  21060
aaggtgaatc agaagataat gatgattccg cttttgaact gctctgtaaa attcgcacag  21120
gagaaacact gacgacaaaa gaagttgttg ttaatgagaa gaaaacaaca ccgctgccgt  21180
tattcaccga agcctccttg cttgctgcgc ttgttcgtgt cgcggatttt gtcactgatc  21240
caacgattaa aaaattactg aaagataagg ataaagacaa aaaagatgaa catggcggta  21300
ttggtacgcc agctacccgt gcagccattc tggaaacgct gaagaagaga aactatatca  21360
cgctggaaaa agggaaactt attccgactg ataccggata tgcgcttatt gatgccctgc  21420
caggtatagc ggttaatcct gatatgacag cattatggtc tgaaaagcag actgccattg  21480
aaaatggcga cctgacggtt gaacagttta ttaatgagct gtacggtgaa ttgacaggca  21540
tgatttctga tgttgacctg ggcaagatga agattgaacc cgctgcgcca gcagggcagt  21600
ttcaacgcct ggactctccc tgcccttcct gtggtaaaca tattgttatc aggccgaaag  21660
gttatttctg taccggatgt gaatttaaaa tctggagtga gttttctggt aagaaaatca  21720
cccaggcaca ggccgaaaaa ctggttaaat cagggaaaac cgatttgatt aagggattta  21780
aaaagaaaag tggtggaacg tatgatacag ttcttgtcct tgaggataag aaaacaggga  21840
agctgggttt tccggcaagg gctaagaagt gaaaacaaag caggaatggc tttttcagtt  21900
aagaaaatgt acatcaagag atactcttga aaaagttatt gagattaacc gttacaagct  21960
gcctttatca gaatcagagg cattttattc tgccgcagat caccgccgtg cagaactggt  22020
gatgaataaa ctttatgata aggttccttc cggcgtatgg aagtacgtcc attaaacaag  22080
aggattaatt atgagcgaac tgactaaaga agatgaatac ggcattatca gccggactat  22140
gatgaatatt cgttcattgc gtgtgtttgc ccgtgagatt gattttgagc agttgctcga  22200
aatgcaggaa aagctcaacg ttgttattga agaacgtcgt gaagatgctg aacgtgaagc  22260
ggctgaacga gcagagcgtg aacggaaacg tcaggaactg cttcagttaa tcgccggaga  22320
gggtttctca ccggaagaac tgcttggtct gtccgaagaa gcaccaaaat cacgtaaaaa  22380
aacgttacca aaagcgccac ccaagtatca atttgaagaa aatggtgaaa cgaaatactg  22440
gtctggtcgt ggacgtgcgc caaaaccgat tgatgaagcg ttgaaagccg ggcgttctct  22500
ggaagatttt cgtatcaata agagtttgaa cggagtaaca gatgagcagt aatatggcaa  22560
ggatatagtt ttatatcatc attttgttaa ggaagaaaat ccatgagtaa tacatcctac  22620
aaacaaatta tccctgcgac agactggtat ttccgtcacg ataatgtctc cggtgtggca  22680
ggaaagtcaa cagtatacca actggctgca tgggcgctta aagaaaatgg tgaggtagtt  22740
ggtctggtga cggttcgtga tgataatggg cgtcctaaac tggttactcc tccccctgtc  22800
cctggtgatt atttgcataa agaacaactc accgatgatg aaaaagagtg ggcgaagaga  22860
```

```
cgctaaacta tattcatata aagcctctgt tctagaggct ttattagcat gtttagttgc  22920
actggagttg ataatggctt caatgctcaa attgaggtaa attgatattg attttacttt  22980
tccgttgctc gtttctcgtc ttattatatt taaatgacaa ttgtaattgt ataatgtttt  23040
attactcttg aattgtctga gcctgatatt tttcaataat aatgttattg attcctaaat  23100
ctgatagcag ataagatgtt acaattgttt ttaggtagtt tccaatttta acataatcac  23160
caatcgtcaa tatgttcatt aactcctttt tgcggtcaac atgtgctaat tcatttctga  23220
gtgtggcaat attttcacca atagatttat tgttgaattt cttaaaaaac atctctatct  23280
cttgaataag aaacaaactt gcatattcat taatgggttt catgtatttt tcattttttg  23340
agccacctat tgttttgttt attgcttcta attgagtcgc aaacaatata atatcagtat  23400
gagcttgatg cagtgttcga aaaccggttt catactgata tgttattgtc aatggcatat  23460
atctttctgc tattttgaac catttgcaga atatctttcc aagattaata tgcttcctgt  23520
ttattggaag gagttgatgt tttatttccc tcagcgctag gtcaatagtt ctttgttcaa  23580
accccgttgt taagagacat ggtgtcttcg aatcatttcc cttgaacttt atgtttattt  23640
cttcaggaag agtcggtttg ttcagaagaa ttgaaaataa cccggaaata tcccagcact  23700
ttgatatatg gtcttttatt cctaaatcat tagatgattt tatcctaaag tagaaaacaa  23760
gttcttttct aatggagaaa aaagcatcag ggtataactc ttttgtcttt tttagttgat  23820
gaattatgtt ctccagtgcg gctttgtttt ggcaatttat tatgtttaat agatcatcac  23880
caattacgct aaaagataca tggttgacaa gttgaagagt ccaatggttt ccttttgcga  23940
taaatattgg atgttctaaa tgtttcaatt gagtgaaaaa accgtgaggg tggataaatt  24000
cttgcaatcc gtgcaaggat aaatcacaat attctatctt tgagtcgggg gcataaaaat  24060
cattgaatag cattatggga aatccatgcc ttccagtatg gataatccct ttaccaaaat  24120
gaatattccc ttgtgtgaaa tcaaatttcc caattagagt acatctttct ccagtattta  24180
agactccata taatatttca catgttctgg ggctttcact gtcagaaata caataatcta  24240
gaatcagacc atggtacggt gaatattcaa ttcgtgcaga aaatcttcct ttgttatcat  24300
caagttggtg ccaaaattca ccatgaaaaa agtattcttt tgttagttcg tatttttttg  24360
ttgccatgta ctgctccatt tgtttctgag aatccttcag aatagtaaaa atactactca  24420
aaactcgtct tcaagatctc tggctatctg ctcattttca tgatgctcaa cagcatcact  24480
gatcaaattc atcatgttat taagaaactc ctctacaact ttaaacgcat cattgagcgt  24540
agctgtattg aatgtatgta tcttttcatc cgttgttttc gttttcccgt tacgatgaac  24600
tatgtcatgc ctcagtttca tcaattcatt gatatttttg agtggaaaac gtggatattg  24660
cttaggttgc aggactgctt tatatatttc aactaccagt tggattctat gataaagaat  24720
atctgaaagg tactcctgta catatttgtt tgcattagac tctttattta tcaactcaga  24780
cagagagata ttctttgctt tcagttcatt tatgtttctt atggcatttt ctacatatct  24840
gttatgtgac aatacaacgc ttttaatcat ttcgctaaga cagttttcca ttattgtcac  24900
aatgtatgcg attttcattt ttatgaaaac ttcacttgta gattgttttc cctcttcttt  24960
tatttgttct aaaaggttta ttgctatttt ataaatttct gtatgtggat gctgttttaa  25020
ccatttttcg ttttcatatt cttccatagc catatcagaa agaaagtcct gatactcgtc  25080
atagtccttt tcaagtaact gccattcttc agaatcctcc tcaagatctg ggctggaaag  25140
ccgttctcgt atccattcct cacggcgact ttcctcgact tgcataaccc aatcttttgt  25200
agctcccaca ataccctcct tatgttcatt gctaaatatc aatagtcact ttatcggaga  25260
```

```
ctacgtgaaa aatcttctcc tttccccctg ctttttttatc agatttcacg cagcgtaccg  25320
ccgctactgt atccatcaaa aaaactgata gctttttaat catcttttgt gctgcaactt  25380
actgaaaaaa ggattaatgg aaacgccgat aacggcattg atctgttggc caacgcgacc  25440
ggcagcattg gacttaacaa aaaaactgaa agaaaatccc ccaaatgaag ggaaaaaacg  25500
gaagaacagt cgaacgacag gcacaaaaaa acccgactgg taatcgggct ttttcgtgtt  25560
ttccagtcct gagttggtgg ctctgactgg aggaagatac tctacatcca acatccacaa  25620
tattatggca ctagacacca gttgtctagt ttgacttcag attgtctgtc aatggccatt  25680
tctttaaatg aattttatgc gtgcatctgt ataatctttg tgttggcgct gtacagtgtg  25740
cctcccttgc ttctaacccc tgcgctatct ggggatgaac gaattaaagt cctggctgaa  25800
caaacaggtg gtgctgtgtt cagtgctctg gcagggggaa ggtactctac atccaacaat  25860
gtgagagagc cgttgtgaca ggcgatgtat gagcaagcaa cggtgacttc ctccagtatc  25920
aacctagaga aacggatgat gaatctgtta atcatcgttc tcagggctgt gctcgccatt  25980
gcaaacgcgc tgattgccat tcagaaacta atcgagtgat tgatggctta actaagggag  26040
agacgtttac cgcttcctgc cctttaacaa aggagtgttt atgagttttg aacaattatt  26100
tacactaacg acccaacgtc gttgggtttg ccgcagaaaa tttattcatt taaaatagat  26160
ctaaatgaag cgggaaactg cagacgtaaa aaaaccgact ggtgaggtcg gctttttttac  26220
agttccggta cgagctggta actcgcccgg aagagaaact ctctacaact gacaacagta  26280
tgataatccg tgaagcctga ttatgcaata tgacaggcgg tgactacgcg ttaacggttt  26340
gcttgaaagt tagataaacg tataatcaga gggttagtgc tgtggtgagt ctttccctgc  26400
attccgctaa atgcggcatg aacagcttca aagtcctgac aggtaataca ggtggtgctg  26460
gttatctgtg ctctggtagg agtgagactc tctacaactg acaagacgaa gagaagccgt  26520
ggtgacaggc agcgtaagag caagccacgg tgtctttact ccatttatgg agaaaacgga  26580
tgattaacct gttaatcatc gttctgaggg cggtagctgc gcttgcaaac gcgctgattg  26640
cagttctgga actgatccgt cagttcatcg attgatgact gcggaaacgt aactaagggc  26700
aggaagtgca ccgcttcctg ccctttaaca aaggaggtgt tatggatttt atgagcattt  26760
tggggcgctg tttacttctt cctttccctg ttgcgatgtt tgtcggttgc ctgtttccag  26820
gcatcgatga tcgttttact ggaatgttca tgagttttat tgtcggttgt ctatcgtggt  26880
atatcaccaa gccaaaaccg caaaaggctg aggtcgcgta agcggccttt tattttgata  26940
cgcattagtt acaacattca atttgctttt taaaaatatc cacttcagca cctccctcat  27000
aaataacgtc aaccagttta ttgagctcac cctaccctac tcaccggagg attgcaggga  27060
tttacgtttt attgcgctac tgattgtgcc gcggctgcac cctagtacct tctgtacctg  27120
tgtccaggag ctgccacttt ctatcaacct gataattgca tcatgtctgg cttgattagg  27180
tttacgccct ttatatttgc cgtctttcct tgctttctct atcccctgtt tctggcgttc  27240
ccgccgttgt tcatagtccc ttctagcaac agcggccagc atatccagca gcatatcgtt  27300
aatggctgca aacaaccggc tgtcaaactc actcatacca gaattaatcc aggtcgtcgg  27360
cacattcacg gccataaccc ggatatcttt ctgacggatc attttcttca gcgtattcca  27420
gtcttcccct gacagtcggg aaagtctgtc cacatcctcg ataagcaaaa tgtcattttg  27480
ctggcaatct ctcagaagac ggaagagttc cgggcggtca agacgggagc cggattcatt  27540
ctcaatataa tagctgcaaa tgatcaggcc tctttccctg gcaaaagcct cgatagtttc  27600
cagggcacgc gaagcatcct gttctgctgt tgaagctctc agataagcgc ggacaaagtt  27660
```

```
tgttggtgca tttgaagtca tattacagaa ccagttcgca taaggtcaca ccactatacc  27720

caaaatgaac cagaaagtgg atcgacagga aaggcacact ctaaaagaac cgaaaaaaca  27780

aataatgagt aaatgtgaca tcgtcaccca tactcataaa ctcacatgct catatacaca  27840

acaaactcaa atgagtatgt gctctttaac tcataaactc atattaacct ttactcatgc  27900

aaagagtatg gtaaactcaa aaactcacaa gagtaattga gtagatacac aattgagggt  27960

ttgagtatga aagtaatctc atttctgaat ccgaaagggg gttcaggtaa aacaactgcc  28020

gtaatcaaca tagccactgc gttgagcaga agcggataca acattgctgt ggtagataca  28080

gatccacaaa tgagcctgac gaactggagc aaagcgggca aggcagcatt tgacgtattt  28140

acagctgcat ctgaaaaaga cgtctatgga atccgaaaag atctggcgga ctatgacttt  28200

gctattgtgg acggggcagg ttcgctctca gtaatcacct ccgcagccgt catggtaagc  28260

gatctggtaa ttatccctgt tacacccagc cccctggatt tctccgcagc aggaagcgtc  28320

gttactgttc tggaagcaca ggcttacagc cgcaaagttg aagcccgctt tctgatcacc  28380

cgtaagatag aaatggcaac catgctcaat gtgctgaaag aaagtatcaa agacactggt  28440

gttaaatctt tccgtacggc cattacacaa cgtcaggttt acgtgaaatc aattctggat  28500

ggtgacagcg tgtttgaatc cagtgatggc gcagcaaaag gtgaaataga aatccttaca  28560

aaagagatag ttagcacatt tgagtaatta ctcattcact catataatca aataagtata  28620

acaaccggag taaccttaat gtcacttgaa aaagcgcata cggcagtaaa aaaaatgacc  28680

tttggtgaaa acagagatct ggaacgagta gtaacagcac cagtatcatc tggaaaaatc  28740

aaacgtgtta acgtcaattt tgacgaagaa aaacacaccc ggtttaaggc tgcatgtgcc  28800

aaaaaaggta catcgatcac agatgtggtg aaccagcttg tagataaatg gctcaaagag  28860

aacgaataat atctgaggat atatcatgga taaaaacgtc gttgatgcgc tgaaaacgct  28920

attagaagcg ttaccggaag aggtggtaac agaagtcaca tcaaaactaa atccttcggc  28980

aagccatatt cctgaagaaa acagtaagca attgacagca aaagcaagac tactgaattt  29040

ccggctaacc gaagcctatg aagaaatcct ggaagtcgaa gctatcagaa caggccagag  29100

caaaactacc gttctaaagg cagcactggc gatgtacaac agccaggatg aaaacataaa  29160

gaatcactgg ctacttgagt ctgcaaaaat taactaattc aggatataga ttattagtag  29220

gagttcgggc aataatggat gataactcta cgtcagtaac cagcaaagaa gatgtgcagg  29280

atatttcttt aaaaaactgg ctaaagaata aaaaaaccat tgtattactt atatttactg  29340

cattaacaaa tgttggcaat gtcctttcga cgattgatat tatcacagat aaaaccagtt  29400

ctttttacac atggcttggg gaatcgaaaa aattcgaagg ccattggacc aacaatacag  29460

aaggattcat agacggcact cctgattttt tactcaagaa tgcaggcgat gtcctcataa  29520

aatttgacct gaacatcaaa ggtggcgaag tgaggggaga gcttcacacc gacgcacgac  29580

taaaaatgtg tgaaactata gaagaaaagt taaaaacttt gtgtacatta atagcctcac  29640

atccactaat gattgagggg gaaaaatcac cattttccaa tgaattcgat gcctatatta  29700

ctgagtatag aaatggagat aaaaaaatag tcgcaatatt aaatatgaaa attacagacg  29760

atgacaaaat gacaataaca aatacaatga gaacaccaga atcagcatta ttttcaacta  29820

aaatatatgc tataaaaata ataaccgaag aataacttaa taacaaaaaa ggtattaaag  29880

tgaatactgg aataacaatt gatttgacca acctttcaga agatgaattg cttgatttat  29940

attcaatgta taaaagtgca aacatagcac atcaactatg gtgcagacgc catgaaaata  30000

taccagagca tttttcgata atattcgtga cgcttttaga acgaataaaa agggttacag  30060
```

```
aaaagaactc agaaggggta aaaacaccag atgtagacct ggatgcatta attgacacca  30120
tttatattgg ttgtcgttca atgttctgtg aaaaccctgg cttaaaaaat aactacactc  30180
tgcaaaactg cctgaggaaa gccaattatc acaacgaagc tagagtgata gataatattt  30240
tacaggaaaa aaaattcaca gattccatca tgaaagatga gtcatttttt agtctggtga  30300
aattagtttc caataagtcc attgcacacc aggagagcct ttcaggaaaa aaacgggaaa  30360
agatagacta tcgatataaa ttcttaaatg acaattcaaa tatctgtgag tttcagtatt  30420
acatttttag atgtcaccgt atttatgaga atattgtgaa agaatatggg gatacattac  30480
tgaatgagct taaaataaaa aacaatgata tataaagaat gcccccatat gaatagaagg  30540
aagaatcata ctaataaatt ttccagctta tcgctggtaa gcaattctgc cagcgaatca  30600
catttcataa aatcaatatc catttcgtcc agaacatcac agtagctgac atcatcaaga  30660
ctaatgacaa tcacaggaac accctctttg agatcaaaca ctaagacagg taatgaaatg  30720
gagtttatct tttcaaaatc actaaaaaac tgttcagttc catattcact ggcaggaaaa  30780
agaatctcac ttaatctcac acaataaaaa acatgatagt gttctttaag gttatccttt  30840
aaaatattaa cagccttagt atatttttcg ttaataaact ctttgaccaa atatttcata  30900
aaactctcca acaagaaccg actgtaggtc atcgggcaaa cgttgcggaa tggcgtcaga  30960
gacgtcattt tgcggcgttt gccctatcct gcatcgcagt ggcatcattt ctggcttatc  31020
tcgctactgt tctcggtgct ttcgtccgca ggttcgggaa caagtaactt gtgccagggc  31080
atagttttgt tgagcagctc catcagaggc tcagccagca gtcccaaaat ccaggttgcc  31140
gtaatcaccg gtatagtgag attttgtggc gtccataact ggtgatcgag atgataccag  31200
gtgatgacac acaaaatacc acccagccag aacacagccc atttaaacgc accaagaatg  31260
gctaacacaa aaacaaagat aaaatgtaaa acactcgcgg caagaagacg aagataaaac  31320
catccccagt caagccactt aacaaaagtg ctccctgttt tcactgcaaa acgtttctta  31380
cgctccctgg cgatttcttt cctgaattta gcacgttctt ccccctgagg gaattgatag  31440
attttagcca tgagttacct catttcgatc tcaaaacgaa gtttatgcaa ttatcctctg  31500
aaaccgtatg gtattctgat atctaggcct tcactttctt tatctatttt ataagaaaac  31560
cttagctttg atgctcttct tgcgactctc tcaacgattt taacttcgag atgattaatc  31620
tctgtatatt gatttatttt ttcaatgttt ttttgcagaa aaactttatt aaagtcctta  31680
aaattctgat aaaggtaaac tttttcgcca ttatctattc tgaataattc aagttcatcc  31740
tttaatacat ctacttcaat gtcaaaaaat gtctttttac cactgctgta ttgtttcctg  31800
ataaactgat aaagcatatt tgaattttga tcagcaagtc ttacagacga tatcaaaacc  31860
tgagtagtgt aagaatcctt taacatcgtg atatatggct caatgacatg tgaaaaagca  31920
atatcaatat atccttcact ttcaacataa tcacaaaacg cagtcaggtt cataagcctg  31980
actgcatcag aaggtaattt acctctcttc ttcgtatgtc cagagatttg attgccctga  32040
gctgtgagaa gttgatttcg aggaatgcga ataacactgg cctgaagttc ttctgccccc  32100
tctttcaact gccggtaagc acctgttaca tcaatatcag cgataaatgc atattcccga  32160
gccgtaatac gaaaggttgc cccctcagat aactcttcac gtgaatcaat ctgcgccata  32220
gccataaaca aaattcttct ggcagacaaa ggcaacgatg agaatgtgct gttaatttca  32280
tttctgtggc gaatttttgt tttctttgta acgctcagta agttcataca ttacctgtgg  32340
tttttaagtt ctaatggtga aatcataacc acaaaggcgg aaatatgtaa agtggtttat  32400
ccaccttatg tatttccacc aaaacacgga tcacatgaaa gaatttttat cattaatatt  32460
```

caatatgata gaaatgcgca ggtatccacc ttttaacgtc atacgttaga ttagagcact 32520
ataaagaact aaagaaatga agatacaaag atacgaatat ctgaataaaa acaggaaaat 32580
gcgtacccat ccacctttca gtgcgtaccc atccaccttt cagtgcgcag ccatccacct 32640
ttcatgaaaa ttacagtgcg tacccatcca cctttcagtg cgtacccatc cacctttcat 32700
tttgaggcga caaaaaacaa cacctatctt aatgaaatta ttgataaaaa aactggcaca 32760
atgtttgcag aataagttaa agtaagttaa agatcttaaa gtagatctac cgatctacat 32820
ttaagatctt aaaaacaaga agtttaataa gcaaaaaaac acaaaaaatc tgtggataac 32880
tttgctcaaa acaaaaaatt cacactacct gtggataact ttgcgtaaac ccggaggaca 32940
gatcactctg 32950

<210> SEQ ID NO 3
<211> LENGTH: 837
<212> TYPE: DNA
<213> ORGANISM: SALMONELLA ENTERICA SEROTYPE ENTERITIDIS

<400> SEQUENCE: 3
atgaacttac tgagcgttac aaagaaaaca aaaattcgcc acagaaatga aattaacagc 60
acattctcat cgttgccttt gtctgccaga agaattttgt ttatggctat ggcgcagatt 120
gattcacgtg aagagttatc tgagggggca acctttcgta ttacggctcg ggaatatgca 180
tttatcgctg atattgatgt aacaggtgct taccggcagt tgaaagaggg ggcagaagaa 240
cttcaggcca gtgttattcg cattcctcga aatcaacttc tcacagctca gggcaatcaa 300
atctctggac atacgaagaa gagaggtaaa ttaccttctg atgcagtcag gcttatgaac 360
ctgactgcgt tttgtgatta tgttgaaagt gaaggatata ttgatattgc tttttcacat 420
gtcattgagc catatatcac gatgttaaag gattcttaca ctactcaggt tttgatatcg 480
tctgtaagac ttgctgatca aaattcaaat atgctttatc agtttatcag gaaacaatac 540
agcagtggta aaaagacatt ttttgacatt gaagtagatg tattaaagga tgaacttgaa 600
ttattcagaa tagataatgg cgaaaaagtt tacctttatc agaattttaa ggactttaat 660
aaagtttttc tgcaaaaaaa cattgaaaaa ataaatcaat atacagagat taatcatctc 720
gaagttaaaa tcgttgagag agtcgcaaga agagcatcaa agctaaggtt ttcttataaa 780
atagataaag aaagtgaagg cctagatatc agaataccat acggtttcag aggataa 837

<210> SEQ ID NO 4
<211> LENGTH: 231
<212> TYPE: DNA
<213> ORGANISM: SALMONELLA ENTERICA SEROTYPE ENTERITIDIS

<400> SEQUENCE: 4
atgtcacttg aaaaagcgca tacggcagta aaaaaaatga cctttggtga aaacagagat 60
ctggaacgag tagtaacagc accagtatca tctggaaaaa tcaaacgtgt taacgtcaat 120
tttgacgaag aaaaacacac ccggtttaag gctgcatgtg ccaaaaaagg tacatcgatc 180
acagatgtgg tgaaccagct tgtagataaa tggctcaaag agaacgaata a 231

<210> SEQ ID NO 5
<211> LENGTH: 621
<212> TYPE: DNA
<213> ORGANISM: SALMONELLA ENTERICA SEROTYPE ENTERITIDIS

<400> SEQUENCE: 5
atgaaagtaa tctcatttct gaatccgaaa gggggttcag gtaaaacaac tgccgtaatc 60

```
aacatagcca ctgcgttgag cagaagcgga tacaacattg ctgtggtaga tacagatcca    120

caaatgagcc tgacgaactg gagcaaagcg ggcaaggcag catttgacgt atttacagct    180

gcatctgaaa aagacgtcta tggaatccga aaagatctgg cggactatga ctttgctatt    240

gtggacgggg caggttcgct ctcagtaatc acctccgcag ccgtcatggt aagcgatctg    300

gtaattatcc ctgttacacc cagccccctg gatttctccg cagcaggaag cgtcgttact    360

gttctggaag cacaggctta cagccgcaaa gttgaagccc gctttctgat cacccgtaag    420

atagaaatgg caaccatgct caatgtgctg aaagaaagta tcaaagacac tggtgttaaa    480

tctttccgta cggccattac acaacgtcag gtttacgtga aatcaattct ggatggtgac    540

agcgtgtttg aatccagtga tggcgcagca aaaggtgaaa tagaaatcct tacaaaagag    600

atagttagca catttgagta a                                               621


<210> SEQ ID NO 6
<211> LENGTH: 252
<212> TYPE: DNA
<213> ORGANISM: SALMONELLA ENTERICA SEROTYPE ENTERITIDIS

<400> SEQUENCE: 6

atgagctatc aaattctgac aaccacagcg gccagtatta ctgacctgaa aaaaaatcct     60

atgggaaccg tagctgaagg tgaaggggac gctgttgcga tcctgaaccg aaacgaaccg    120

gcgttctatt gcgttccacc aaaactttac gcctactatc gggaactcgc tgaagatgct    180

gagttaaacg ctgttgctga tgagcgcatg aaaaacccgg aaattgtgaa ggttaacctg    240

gatgacctat ga                                                         252


<210> SEQ ID NO 7
<211> LENGTH: 282
<212> TYPE: DNA
<213> ORGANISM: SALMONELLA ENTERICA SEROTYPE ENTERITIDIS

<400> SEQUENCE: 7

atgacctatg aactggcttt tgaccgtaga gcactgaagg aatggcagaa actcggccac     60

accatccgtg aacaattcaa aaagaaactg gcagaacggc tggaaaaatcc acgcgtaccc    120

gcagcccggt tacatggtca tgctgatcgc tataaaatca aacttcgtgc atctggctac    180

agacttgtat atcaagtcat tgatgagaaa gtcgttttac ttgttatttc cgttggaaga    240

agggaaagca gcgaagtcta tcagatcgca gatttgcgct aa                        282


<210> SEQ ID NO 8
<211> LENGTH: 648
<212> TYPE: DNA
<213> ORGANISM: SALMONELLA ENTERICA SEROTYPE ENTERITIDIS

<400> SEQUENCE: 8

atgttatcta cttctacttt tcttgcgctt gccatgcaat gcgctgccag cgttcatccc     60

gacacaacgc acgaagtcgc cagggttgaa tcaggtttta acccatatgc gattgcggaa    120

ataataccaa aggttaaacg taaaactggt gataaaggcg tagtatctta ctttcctgaa    180

tcaaaggagg cagcacttaa gatcgttaaa aacattgaat tacggaatca tcgttactct    240

gtaggactta tgcaaataac gagtaccaat tttgcaaagt tcggtacaac agcagagaaa    300

atgtttgatc catgcgaaaa tcttaaggta tcagaaaaaa tactggttga ctgttataaa    360

cgaggtggcg acttagtgcg tgggctgagt tgctattatt ctggcaatca agaaacagga    420

gtaaagccag aacctgaatt taataataca agttatgtac aacgtatagg atttagccct    480
```

```
cctgataata aaaaaagttt tattgttccc tctgtaaagg aaatgattaa aaaggagaat    540

aagacgacta tcacacctga agaaatcatt atatatcctc aatacgccat gcgtggcact    600

gtatcaaatg aaaaggaaac aaaagatgtt gaaattaaat ctgaataa                  648
```

<210> SEQ ID NO 9
<211> LENGTH: 297
<212> TYPE: DNA
<213> ORGANISM: SALMONELLA ENTERICA SEROTYPE ENTERITIDIS

<400> SEQUENCE: 9

```
atgttgaaat taaatctgaa taaacgttat ttaacgcttt ctctatttat ggctgcgttg     60

atgctttgtg ttgcagaacc tgcttttgcg gatgatgtgt ctacgaagac aactggtttt    120

ttacagaaaa taattgattt tttaacggat attcgtaaac ctgcaattac aattattgct    180

cttgttattg ggtatattgc gatattttct cgtcaacata cctcatggat agtcccactt    240

gttatcggaa ttatcatctt tattgttgca ccatatattc ctgactggct tgcgtaa       297
```

<210> SEQ ID NO 10
<211> LENGTH: 2754
<212> TYPE: DNA
<213> ORGANISM: SALMONELLA ENTERICA SEROTYPE ENTERITIDIS

<400> SEQUENCE: 10

```
atgagtactc tttttaaagg tcttacgcgc cctgctttaa taagggggct gggcgttccg     60

ctctacccct ttcttggaat gtgcattatt tgtgttctgc ttggtgtctg gattcatgag    120

gctatgtatg cccttattct tcctggctgg tatgccatca ggcgtgtaac acagtttgat    180

gaacgctttt ttgaccttct gtatctgaga actcttgtca aagggcatcc tttatcaaac    240

aagcgattca gcgcagtcca ttatgcgggg agccagtaca atgaagttga tatttcaaaa    300

gtggataact ttatgaagct gaaagaccag tcttctgttg aagagttaat tccgtactct    360

tcacatatca ctgataatat tatcgttaca aaaaaccggg atttgctggc aacctggcag    420

atagacggtg cttactttga gtgtgttgat tctgaagatt tgtcaattct gacagatcag    480

cttaatacgc ttatacgtag ctttgaaggg aaatttgtta cgctttatcc tcatcgtatc    540

aggtgtaaaa agggcgtcag accagtattt aacagtaaaa ttccttttgt gaacagagta    600

atgaatgatt attacgagtc attccctcag tctgaatttt tcgagaataa attatttctg    660

acgatttgtt ttaaaccttt tactacggaa gataaagtaa cacatttctt ttcacgcagt    720

aaaaaacaaa aagatatctt taaagagcct gttaatgaaa tgaatgaaat ttgcgacagg    780

ttgaatacct atctgtcccg ttttcattcc cgacgtcttg ggctttatga agatcatggg    840

gttgtttatt cagatcagtt atctctgttc cagtatctgc tttctggtcg atggcaaaag    900

gtcagggtta gcagtagtcc gttttataca tatctgggag gaaaagacct gttctttggt    960

aatgatgccg gacaaattac cgcgtcagac catgcccggt attttcgttg catagagatt   1020

aaggattatt ttcaggagac ggatgccggt attctggatg ctctgatgta tctccccgtt   1080

gagtatgtcg tgacatcgtc ctttactgcg atggataagc agtcagcgat taaggcgctg   1140

gatgatcaga tcgataagct ggaaatgaca gatgatgctg ccaaatcttt gctggcagat   1200

ctgaaagtcg gactggatat ggtttccagt ggatatattt ctttcggaaa atcgcatcag   1260

accctggttg tctttgcgga ttcaccggag cggctggtga aagacaccaa tatcgtgact   1320

tccactctgg aagatttggg gctgattgtc acttattcaa cactgagtct tggcgcagct   1380

tattttgctc agctaccagg aaattatacg cttcgccctc gtctgagtac cctcagtagt   1440
```

```
cttaattttg ccgaaatgga aagttttcat aatttctttt caggaaaaga aaaaggaaat   1500

acctgggggg aaaaactgat tactcttcgg gggtcaggta atgatatcta ccatctgaat   1560

taccatatga cgactgaaca tcagaatttc ttcggtaaga acccgacgct ggggcatacc   1620

gaaattctcg gtacgtctaa cgtgggtaaa accgtattac tgatgacaaa agcatttgcc   1680

gcccagcagt tcggtacgcc ggaatcattc cctgcaaaca gaaaactgaa aaaactgacc   1740

acggtttttt ttgataaaga ccgggcaggt gaagtcggta tacgggcaat ggggggatct   1800

tattaccggg tgaaggaggg agagccgaca ggctggaatc ccgccgcact gccgccaaca   1860

aagcgtaata tcgcttttat gaaggacctg gtgaggctgc tttgtactct caacagtgag   1920

ccgctcgatg attaccagaa cagcctgatt tcagatgcgg ttgaacgtct tatgcaacgg   1980

tcagatcgct cttatcctgt cagtaaacta cggcctctta tccaggagcc ggatgatact   2040

gaaaccaaac gtcatggact taaagcccgt cttaagccgt ggacgcaggg ggaagagttt   2100

ggctgggtgt tcgacaatcg ggaagacacg tttgatgtcg ataacctgga tgttttcggt   2160

attgatggaa cggagttcct ggataataag gtgctggcca gtgctgcttc attctatctc   2220

atctatcggg tcaccatgct ggccgatggt cgcaggcttc ttatctacat ggatgagttc   2280

tggcaatgga tcaataacga agcgttcagg gactttgttt acaacaagct gaaaaccgga   2340

cgtaaactcg atatggtgct tgtcgtagcc acacagtcac cggatgaact gattaaatca   2400

cccattgcgg cagcggttcg tgagcaatgc gccactcata tctatctggc aaacccgaaa   2460

gccaaacgta gtgaatatgt tgatggtttg caggtcaggg agctttattt tgacaaaatt   2520

aaagctatcg atccgctgtc ccgccagttc cttgttgtta agaacccaca gaggaaaggt   2580

gaaagtgatg attttgctgc ttttgccaga ctggagctgg gaaaagcagc gtattactta   2640

ccggttctca gtgcatcaaa accccagtta gaactgttcg atgaaatctg gaaagaagga   2700

atgaagccgg aagagtggct tgatacctat ctggaacagg cgaacctgat ttga         2754
```

```
<210> SEQ ID NO 11
<211> LENGTH: 759
<212> TYPE: DNA
<213> ORGANISM: SALMONELLA ENTERICA SEROTYPE ENTERITIDIS

<400> SEQUENCE: 11

atgaaaaagc aaattatggc ggcattcgtc gcttcactga ttgttatttc cggcgctcag     60

gcagggatac ctgttgccat cgacgccaac cctgaatggg cgattgaagc cggacgatgg    120

acagaacgcc ttaagcaatg ggcggaaacg gtaaaacatt acgaaaatca gataaatgcg    180

tacaaacagg agctgctgtc aaaaacgggt atccgtgatg tgcagggact ggtgcagtcc    240

gcacagtcag tgagtcagga actgatgcag atttatgatc aggggaatgc ttttattgac    300

gattacatta aaaatcctga aggggcgtta tcggaacagg ccaaatcgtt attgtcagat    360

tacaaagtaa cggatacctg ccagaacctg ggatattccg gcgacctggt acggggatgt    420

gaagcgacgt tcctttctca actggcaagc gtggaatacg gtaacaagct ggagagcaag    480

cttcgtcagg acaaccagac gatgaaagac cttattgatc aagtcaaaaa tgcgaaggat    540

acgaaggcca cgcaggatgc aacaaacgct gttgcacttg aacaactgaa gttcgagaag    600

ctcaaatttc agtatcaaat gtatcgcgat aagcagcgag atcttgcaga atataaagag    660

aagatggctc aggcagcttt cagaaaacag caacgtgaag ccgtgccacc ttcttacaga    720

aaagcttata tggcaatgaa atcatatgag gatgattaa                           759

<210> SEQ ID NO 12
```

<211> LENGTH: 1134
<212> TYPE: DNA
<213> ORGANISM: SALMONELLA ENTERICA SEROTYPE ENTERITIDIS

<400> SEQUENCE: 12

```
atggggattg tcactggtat accggatggt actgatttat caggtaatgt aacctctccc     60
gcaaatgcgg gaggtgtttc tggatttgat tctgattttt ttcagacaac tcatgaagtt    120
atatttaata ttctcaacaa gagtatatct ggaaaattaa gtgaatattc agatgtggct    180
tatactcttg gtaaatatgg agtttctctg tatgttttat ggtatgcttt tactgtatta    240
gcaaggaaac aacagacacc tgtacctgat tttatctgga atatctgtag gttttacata    300
atattgcttt ttgttaagaa tacaggggga atacttacat cagcaacaga tgctattgat    360
ggattgaaaa atacattggc agggggagat ccgtgggtat ggatggatca gttatgggtg    420
aaggttatac aagttgcaac tcttattttt gataaagata catctactgt gcctgttgcc    480
ggtgggattg gtgctttatt aacttatgtc ggtggtgttt tggcattatt gctttgttct    540
atagtatttg catctgctga attaacatta ctattacttt ctgtcactgc gccaatattt    600
atcatgtgtc tgatgtttgg tttacttcgg caaatgttta atagctggct acagcttaat    660
tttagctcgt tactggtttt tctatttgca gcattagcac taagagctgg gacatggcaa    720
ttaaacatgg cattaagtac gtctattgct acagcatcag aaaacaatct tcttcaaacg    780
ggagtaactt cattagctgc tggcattttc atggcctgga ttatctggca ggcgaaaagt    840
tatgcttcac agattgcagg tgtgggtgtt gaaggtgcca tgcagggcgc agccgctatg    900
gggattggtg ctggcgtttt cggtgcatcc cgtatggcgc gtggcgcact tggtatgggc    960
agaaatgccg gtattggtgc atggaaaggt ctgcgtcgtc aggaagacgg gtttggtcag   1020
tctccgggaa taacgggtaa gaccgctaac ctggccggac agggcgttaa tattggtgcc   1080
aaaaagcttc gtcaggcagc tattgagaga gcaaagaaaa tgtatggtgg gtaa         1134
```

<210> SEQ ID NO 13
<211> LENGTH: 129
<212> TYPE: DNA
<213> ORGANISM: SALMONELLA ENTERICA SEROTYPE ENTERITIDIS

<400> SEQUENCE: 13

```
atgaaactac ttattgtggc tttcgtgacg ctttgtctcg ctggttgtca ggcgtcacat     60
aaactaccgc ccgtttccgg gaaaagcgaa cctgttaatt ctgctgaggt aatgcaaaat    120
ggaatttaa                                                            129
```

<210> SEQ ID NO 14
<211> LENGTH: 714
<212> TYPE: DNA
<213> ORGANISM: SALMONELLA ENTERICA SEROTYPE ENTERITIDIS

<400> SEQUENCE: 14

```
atggaattta aacttcccgg atttaaaaat aaaaaagacg ttactgactc atcagtttca     60
tttgaagaaa aaaacattgc actacaggag agaatgaatc gtatttataa attcggtggt    120
atcggaggca tgttaattgg tgggctgtct ttacttgcat taaatgcagc attaccactg    180
aaaacaacag ttgttgatgc ctaccttatc gataaggtta caggtgtggc tgaacgtctg    240
acttctgtta aaaaagaaaa tctttctgaa aacgaagcca ttgcccgata ttttatcacc    300
cagtatataa aacatcgtga aggttataat tttttcagtc tccagcatga ttatgattat    360
gtaatggctt acagcgcgga gaatgtcgcg gcagattata acgcattatt taacagtgaa    420
```

```
caggcaccaa aacttgttta taacaaagca gaaaaaacgg caatggttca ggataatcca    480

tctgtcataa tttcaccttc gtcacgggca gatgataaag atatcggtgc gtatattcgt    540

tttcgtctga ccatcaggga tgttgctacc ggacaaaccc gccaggagtt ctggaatgtt    600

cgcctgactt atcgtatcga accgcaggtt gaaatggtgt caggggaacg taataacaat    660

cctcttaaat tcgttgtaac aagctacgtt cgcgataaag aagccagagg ttaa          714


<210> SEQ ID NO 15
<211> LENGTH: 930
<212> TYPE: DNA
<213> ORGANISM: SALMONELLA ENTERICA SEROTYPE ENTERITIDIS

<400> SEQUENCE: 15

atgaaaatga ataaaggagc gttaattatg gcgcttctga tggcggcgca cgtctgtcat     60

gcagctgttc ttccttcagg cagtcgcttt gacccacgca atcagatagt cagttataac    120

cccaataata ccaccataat taacagtgcc gttggataca ccaccacact ggtatttgat    180

gaagatgaaa cagttatcag tgccagaact ggttttccgc agggatgggc ggttaataaa    240

gaagataacc tggtatacct ggaagttcgt cctgttaaac agactgttca gaaaaataat    300

atggatgaaa acggtaatac ctcttctgaa tccgtcagtg ttgctcttga cccggaaaat    360

gagcttgaac gctggcgaac gaatttgttt gttcgcacca cgaagcgtaa ttacagcatg    420

gagctgaacg cccggacgtt ccggcagccg gagaaaattg cgtttgtggt gaattaccag    480

tatccgcagg aacgccggaa ggaacaggcc gaaattgaga agaaacgcac agaggctctt    540

gccagacgcc aggaggagca ggcaatcaac cgttccctgg aaaatgcgaa atcgccccgt    600

aactggcagt actggaagcg ggttgctgaa ggcagccagg atatcagccc tgattatgca    660

tatgacgatg gccgttatac ctggttcggc ttcagtccgt taaagaaaat tcccagcgtc    720

tttgtgatga acggtatgca ggagactctt accaatcctg tgattaaaca gagcgggagt    780

tttacggctg ttggcgtacc ggttgataag cgttttgttt tacgtcttgg tgagcaggtg    840

gtggggattg agaaccaggg cttcggaaaa gtacgtttac cagccggaga tacggtatcc    900

ccggatgtta agaaagaggt gatccagtga                                      930


<210> SEQ ID NO 16
<211> LENGTH: 1206
<212> TYPE: DNA
<213> ORGANISM: SALMONELLA ENTERICA SEROTYPE ENTERITIDIS

<400> SEQUENCE: 16

gtgactgaac aggaaaataa aatcccgact gcaaccgaaa ttgaacagca gctacgggaa     60

cgcagacaga aagaactgga acaggccggg aagactccgg aagaagagcc tggcaagcca    120

gcattgcagc ttggtattga aaaacttaaa aagtcacgta aagggatgat tatcctcgtc    180

gtgggttttc ttctgcttgc tgccggtgtt tctgtttatt atatcccgtc cattatccgt    240

tctgtgtcgt caggggatga gaaacccgca agtcagccgc ttgcaaccgg aacggctaaa    300

cgtcagaccg gactgagcga agatatcgat ccttttaata ccgcacagaa aaaaacagag    360

aaaccagagg aagaaaaagt catttcttct gaaaagactg aaccgccgga aaataaacag    420

cagagcttca gccgtgcact tgacgtttct cttgatggca gccagacagg aaacagcagc    480

agttcagcgg gaacgtcagt ttcacatact gcggccagtg agccagaaag cgataaaaag    540

gatgaagcaa aagcaaccgc acagactaca gaatctgcgc cactggcgaa aataacgaaa    600

cttccatatg acccaaattt gtttatcccg gaagggacat caattccctg ttcactggac    660
```

```
aggcgttttg tttctgacct ggcggggaaa ctggaatgta cggtcaacag cgatatatac    720

agcgccagcg gtaatgtaaa acttatcgaa agaggaaccg ccgcaaaact gatgtataag    780

gccgggtctt taaatcatgg acaagggcgt gtgtttgtta tggcttacaa gctacgtacc    840

cgcagtaagc cttttattga tattcccctg gttgactcac aggcggctgg cgcgttaggc    900

gaagccggtg cttctgggtg gattgacact catttcagtg aacgttttct tggtgcaatg    960

atggtcggga tgataccgga tttaagtcag gccgccagtg gtattgcaca gaacaacagg   1020

gacagccaga ccgactatac ggcaaacagt cgccaggctt ttgctgatat agcacgcgaa   1080

gcattttcta atagtgtgaa tattccgcca acgctttata aaaatcaggg cgaaattatt   1140

actctgattg tcggtcagga tctggatttt tcaggcattt ataaactgaa aatgaaaggg   1200

ggttaa                                                              1206
```

<210> SEQ ID NO 17
<211> LENGTH: 1032
<212> TYPE: DNA
<213> ORGANISM: SALMONELLA ENTERICA SEROTYPE ENTERITIDIS

<400> SEQUENCE: 17

```
gtgaataacg aaaacagaca tctgatttat gatgtggtca acgattattt ttatcactgg     60

ctgaatgaga ttgagggtgt cacggaaatt gctgttaacc gaccaggaga aatatttata    120

aaggtcaggg gaaagtggca atggtatgaa caaaagatga gttacagtga ttgtctttct    180

tttgcatcca cactggccga ttttcatgac ggcggttctg tgactcctga atatcccctg    240

cgctctgcca cgcttccggg tggagaacgt gttcaggttg tgatcccacc ggcaactgaa    300

aaagacactg tttctataac aatccgtaag ccgtcaggta tttttatcag tcatgacaaa    360

tttataaaac agggatttta ttcacgcgtc agtggtttaa gtggtgactc ggttatggaa    420

gataatattt ctgctttaat cacttccgga tattttgatc gggttatacc tgaatcactg    480

cgtcagggga aaacgatagt ttctgtgga gggacgggtt caggtaaaac tacctttgca    540

aatgcctgtc tggaatatat accgcatcat ctgcggtgta tttctattga agatactgat    600

gaggcaaaat tcagattcca taaaaaccat gtaaaacttt actatccggc agagggtgag    660

agtaaggtta ttacctcagc gagtcttctg cgttcctgtt ttcgtatgaa tccggacagg    720

attctgatga cagaaatcag gggggctgag gcatgggatt ttctgaaagc atcgagttca    780

ggccatgcag gaaacattac caccgttcac gaaagtagtc ctgaatatgc tgtgcttggg    840

attgttcagc gatgttatat gaatcctgaa tgtcagaatc taccattcaa tgtcatttta    900

agacgtgtac tgagtaatat tgatattatc atgagtatta aataccttga tgatgaagat    960

tttcgtttcg cttccggtat ttattacaaa caacttcatt ttgatgacta tttcagaaaa   1020

ctgaaggagt ga                                                       1032
```

<210> SEQ ID NO 18
<211> LENGTH: 615
<212> TYPE: DNA
<213> ORGANISM: SALMONELLA ENTERICA SEROTYPE ENTERITIDIS

<400> SEQUENCE: 18

```
atgacgtctc tgacgccatt ccgcaacgtt tgcccggtga cctacagtcg gttattgtcg     60

gagaatttta tgaaaaaagt tcaattcaga attgatgaaa atcagcataa tgatttgctg    120

gattgtctta aaactcttta tccagatgaa ccagctttaa cagtagctaa aggcatgaaa    180

cttttagcaa atgctttatt aaaaagtaaa gctggcagta aggacataaa tacgtttttt    240
```

```
gataataatg attttatcaa aacaacgatg tacttaacag gtaaacaaag ggctgatatt    300
gaaagagctg ctaatcgtca cggatggacg ttatcacgag aatgtcgtta ccgcatacag    360
acgacacttg aaaatgaact ggatttcttt gaccaggaac tgctgatgat gaatcgttgc    420
cgtaattcaa ttgataagat cggtcgtaat ttccattata tcattgttaa tgatcagacc    480
agggttcttg ataaagatgg tttctatcag gatgcggagc gtcttacaac agaaattttt    540
aatcttaaga atcagtttga gaattacatt atgttatgta aagggagaac tgtttcaaat    600
aaagtggaga tgtaa                                                     615
```

<210> SEQ ID NO 19
<211> LENGTH: 1842
<212> TYPE: DNA
<213> ORGANISM: SALMONELLA ENTERICA SEROTYPE ENTERITIDIS

<400> SEQUENCE: 19

```
gtgattatgt ctttaaaact ccccgataaa ggccagtggg tttttatcgg tctggttatg     60
tgtctcgtga catattatac tggttctgtt gctgtttact tcctgaacgg aaaaacgccg    120
ctttatatat ggaaaaattt tgattccatg ctcctgtggc gaataataac agagagtaat    180
atacggacag atatcaggtt aaccgctatc ccctctcttt tatcaggtat ggtttcgtct    240
ctcatcgtgc ctgtttttat tatctggcaa ctgaataaaa cggctgttgc tctttatggt    300
gacgcgaagt ttgccagtga taatgattta aggaaatcga aacttctgaa atgggagaaa    360
gaaaacgata ctgatattct cgtcggagca tataaaggta aatacctgtg gtataccgca    420
ccagattttg tatcacttgg cgcaggaacc cgcgcaggta aaggtgccgc cattggtatc    480
cctaatcttc tggtcagaaa acactctctg attgcgttag atccaaaaca ggaattgtgg    540
aaaatcacca gtaaggtgcg tgaaatactg ctgggtaata aagtttatct gctcgaccct    600
ttcaacagta aaacacacca gtttaatccc cttttctata ttgatttaaa agcggagagt    660
ggggctaagg atctgcttaa actgattgaa attctgtttc cgtcttatgg catgacaggg    720
gcagaagcgc actttaataa tcttgcgggt caatactgga caggactggc taagttgctt    780
catttcttta ttaactatga gccgtcctgg cttaatgagt tcgggcttaa acccgttttc    840
tcaatcggtt ctgtcgtcga cttgtacagc aatattgacc gggaactgat actcagtaag    900
cgggaagaac tggagggaac aaacgggctt gatgaaaacg cgttgtatca tttgcgcgat    960
gccctgacca aaatcaggga atatcacgaa acggaagatg aacagcgttc aagcattgat   1020
ggttctttcc gtaagaaaat gagcctgttt tatctcccaa ccgttcgtaa atgtactgat   1080
ggtaatgatt tcgatctccg tcagttgcga cgggaagata tcactgttta tgtcggtgtt   1140
aatgcggaag atatatcact ggcttacgat tttctgaacc tgtttttcaa cttcgttgtt   1200
gaagtgacat tgcgtgaaaa tcctgatttt gatcccaccc tgaaacatga ctgcctgatg   1260
tttcttgatg agttcccttc gattggttat atgccaatta ttaaaaaggg atcagggtat   1320
attgcaggtt ttaaacttaa actgctgaca atttatcaga atatcagtca gctaaatgaa   1380
atctatggta ttgagggagc caaaacgctg atgagtgctc atccctgccg tattatctat   1440
gctgtcagcg aagaggatga tgccgcgaag atatcagaaa aacttgggta tattaccact   1500
acatcaaaga gcacaagcaa gaaccgggga cgatcaactt cacagggcga atcagaaagt   1560
gaagcccgaa gagcactggt gcttccacag gaactgggaa cgctggactt taaagaagag   1620
tttatcatcc tgaaggggga gaaccctgtt aaagcagaaa aggcacttta ttaccttgat   1680
ccgtatttta tggacaggtt aatgaaggtc agtcctaaac tggcatcatt gacgatgaaa   1740
```

ctaaataaga cgaaaaaaat atttggtgtg aaagggctta aatatccgtc aaaagaaaaa 1800
atgctctccg taggagagct ggagtctgag gttttgctat ga 1842

<210> SEQ ID NO 20
<211> LENGTH: 1167
<212> TYPE: DNA
<213> ORGANISM: SALMONELLA ENTERICA SEROTYPE ENTERITIDIS

<400> SEQUENCE: 20
atgggcgttt acgttgataa agaatatcgt gttaaacgaa agtcatcaga aaatggtcgt 60
aagtcagctt tcgctcacaa agtcaaaaat ggtggaaaga actatagccg caatgttcag 120
gaacgtatca accgcaaggg tgccagtaag gaggttgttg tcaaaatatc tggaggtgct 180
gttactcgtc aggggattcg gaacagtatt gattatatga gccgtgagtc agagctacca 240
gtgatgagtg aaagcggtcg ggtatggatg ggtgccgaaa ttctggaggc taaagagcac 300
atgatagatc gtgctaatga tcctcagcat gtgatgaatg ataaaggtaa agaaaataaa 360
aaaatcacac agaatattgt cttctcgcct ccagttttag cgaaagtaaa gcctgaagat 420
ttgttggagt ctgtcaggaa aacgatgcag aaaaaatatc ctaatcaccg ttttgttctt 480
ggataccact gtgacaagaa agaacatcct cacgttcatg ttgtttttcg tatccgagat 540
aatgacggta aacgcgctga tatcaggaaa aaagatttac gggaaattcg tacaggtttt 600
tgtgaagagt tgaagttaaa aggttatgac gttaaagcga cccataagca acagcatgga 660
cttaatcagt ctgttaaaga tgcacataat acagcaccaa aaagacagaa aggtgtttat 720
gaggttgttg atattggcta tgaccattat cagaacgata aaacaaagtc taagcaacat 780
tttataaagc taaagactct taacaagggg gttgagaaaa catactgggg ggctgatttt 840
ggggacttat gttcgcggga aagtgttaaa gcaggtgatc ttgtcaggct gaagaaactt 900
ggtcagaaag aagtaaaaat cccggcgctc gataaaaacg gtgttcagca tggctggaaa 960
acggttcaca gaaatgagtg gcagttagaa aatctggggg ttaagggcgt agacagaaca 1020
ccttcagcca gcaaagagct ggtacttaac agccctgata tgctgctgaa gcaacaacag 1080
cgaatggcgc agtttacgca gcagaaagca tccacgttac agtcagaaca gaagctgaaa 1140
acagggatta agtttttggg cttataa 1167

<210> SEQ ID NO 21
<211> LENGTH: 5655
<212> TYPE: DNA
<213> ORGANISM: PHOTOBACTERIUM

<400> SEQUENCE: 21
atgcctgcag atgaagcaag aggaggactc tctatgaaat ttggaaactt tttgcttaca 60
taccaacctc cccaattttc tcaaacagag gtaatgaaac gtttggttaa attaggtcgc 120
atctctgagg agtgtggttt tgataccgta tggttactgg agcatcattt cacggagttt 180
ggtttgcttg gtaaccctta tgtcgctgct gcatatttac ttggcgcgac taaaaaattg 240
aatgtaggaa ctgccgctat tgttcttccc acagcccatc cagtacgcca acttgaagat 300
gtgaatttat tggatcaaat gtcaaaagga cgatttcggt ttggtatttg ccgagggctt 360
tacaacaagg actttcgcgt attcggcaca gatatgaata acagtcgcgc cttagcggaa 420
tgctggtacg ggctgataaa gaatggcatg acagagggat atatggaagc tgataatgaa 480
catatcaagt tccataaggt aaaagtaaac cccgcggcgt atagcagagg tggcgcaccg 540
gtttatgtgg tggctgaatc agcttcgacg actgagtggg ctgctcaatt tggcctaccg 600

```
atgatattaa gttggattat aaatactaac gaaaagaaag cacaacttga gctttataat    660
gaagtggctc aagaatatgg gcacgatatt cataatatcg accattgctt atcatatata    720
acatctgtag atcatgactc aattaaagcg aaagagattt gccggaaatt tctggggcat    780
tggtatgatt cttatgtgaa tgctacgact atttttgatg attcagacca aacaagaggt    840
tatgatttca ataaagggca gtggcgtgac tttgtattaa aggacataa agatactaat    900
cgccgtattg attacagtta cgaaatcaat cccgtgggaa cgccgcagga atgtattgac    960
ataattcaaa aagacattga tgctacagga atatcaaata tttgttgtgg atttgaagct   1020
aatggaacag tagacgaaat tattgcttcc atgaagctct tccagtctga tgtcatgcca   1080
tttcttaaag aaaaacaacg ttcgctatta tattaagtcg aggaggagaa agaaatgaaa   1140
tttggattgt tcttccttaa cttcatcaat tcaacaactg ttcaagaaca aagtatagtt   1200
cgcatgcagg aaataacgga gtatgttgat aagttgaatt ttgaacagat tttagtgtat   1260
gaaaatcatt tttcagataa tggtgttgtc ggcgctcctc tgactgtttc tggttttctg   1320
ctcggtttaa cagagaaaat taaaattggt tcattaaatc acatcattac aactcatcat   1380
cctgtcgcca tagcggagga agcttgctta ttggatcagt taagtgaagg gagatttatt   1440
ttagggttta gtgattgcga aaaaaaagat gaaatgcatt tttttaatcg cccggttgaa   1500
tatcaacagc aactatttga agagtgttat gaaatcatta acgatgcttt aacaacaggc   1560
tattgtaatc cagataacga tttttatagc ttccctaaaa tatctgtaaa tccccatgct   1620
tatacgccag gcggacctcg gaaatatgta acagcaacca gtcatcatat tgttgagtgg   1680
gcggccaaaa aaggtattcc tctcatcttt aagtgggatg attctaatga tgttagatat   1740
gaatatgctg aaagatataa agccgttgcg gataaatatg acgttgacct atcagagata   1800
gaccatcagt taatgatatt agttaactat aacgaagata gtaataaagc taaacaagag   1860
acgcgtgcat ttattagtga ttatgttctt gaaatgcacc ctaatgaaaa tttcgaaaat   1920
aaacttgaag aaataattgc agaaaacgct gtcggaaatt atacggagtg tataactgcg   1980
gctaagttgg caattgaaaa gtgtggtgcg aaaagtgtat tgctgtcctt tgaaccaatg   2040
aatgatttga tgagccaaaa aaatgtaatc aatattgttg atgataatat taagaagtac   2100
cacatggaat atacctaagt cgaggaggat ggcaaatatg actaaaaaaa tttcattcat   2160
tattaacggc caggttgaaa tctttcccga aagtgatgat ttagtgcaat ccattaattt   2220
tggtgataat agtgtttacc tgccaatatt gaatgactct catgtaaaaa acattattga   2280
ttgtaatgga aataacgaat tacggttgca taacattgtc aattttctct atacggtagg   2340
gcaaagatgg aaaaatgaag aatactcaag acgcaggaca tacattcgtg acttaaaaaa   2400
atatatggga tattcagaag aaatggctaa gctagaggcc aattggatat ctatgatttt   2460
atgttctaaa ggcggccttt atgatgttgt agaaaatgaa cttggttctc gccatatcat   2520
ggatgaatgg ctacctcagg atgaaagtta tgttcgggct tttccgaaag gtaaatctgt   2580
acatctgttg gcaggtaatg ttccattatc tgggatcatg tctatattac gcgcaatttt   2640
aactaagaat cagtgtatta taaaaacatc gtcaaccgat ccttttaccg ctaatgcatt   2700
agcgttaagt tttattgatg tagaccctaa tcatccgata acgcgctctt tatctgttat   2760
atattggccc caccaaggtg atacatcact cgcaaaagaa attatgcgac atgcggatgt   2820
tattgtcgct tggggagggc cagatgcgat taattgggcg gtagagcatg cgccatctta   2880
tgctgatgtg attaaatttg gttctaaaaa gagtctttgc attatcgata atcctgttga   2940
tttgacgtcc gcagcgacag gtgcggctca tgatgtttgt tttacgatc agcgagcttg   3000
```

```
tttttctgcc caaaacatat attacatggg aaatcattat gaggaattta agttagcgtt   3060

gatagaaaaa cttaatctat atgcgcatat attaccgaat gccaaaaaag attttgatga   3120

aaaggcggcc tattctttag ttcaaaaaga aagcttgttt gctggattaa aagtagaggt   3180

ggatattcat caacgttgga tgattattga gtcaaatgca ggtgtggaat ttaatcaacc   3240

acttggcaga tgtgtgtacc ttcatcacgt cgataatatt gagcaaatat tgccttatgt   3300

tcaaaaaaat aagacgcaaa ccatatctat ttttccttgg gagtcatcat ttaaatatcg   3360

agatgcgtta gcattaaaag gtgcggaaag gattgtagaa gcaggaatga ataacatatt   3420

tcgagttggt ggatctcatg acggaatgag accgttgcaa cgattagtga catatatttc   3480

tcatgaaagg ccatctaact atacggctaa ggatgttgcg gttgaaatag aacagactcg   3540

attcctggaa gaagataagt tccttgtatt tgtcccataa gtcgaggagg agtaaaagta   3600

tggaaaatga atcaaaatat aaaaccatcg accacgttat ttgtgttgaa ggaaataaaa   3660

aaattcatgt ttgggaaacg ctgccagaag aaaacagccc aaagagaaag aatgccatta   3720

ttattgcgtc tggttttgcc cgcaggatgg atcattttgc tggtctggcg gaatatttat   3780

cgcggaatgg atttcatgtg atccgctatg attcgcttca ccacgttgga ttgagttcag   3840

ggacaattga tgaatttaca atgtctatag gaaagcagag cttgttagca gtggttgatt   3900

ggttaactac acgaaaaata aataacttcg gtatgttggc ttcaagctta tctgcgcgga   3960

tagcttatgc aagcctatct gaaatcaatg cttcgttttt aatcaccgca gtcggtgttg   4020

ttaacttaag atattctctt gaaagagctt tagggtttga ttatctcagt ctacccatta   4080

atgaattgcc ggataatcta gattttgaag gccataaatt gggtgctgaa gtctttgcga   4140

gagattgtct tgattttggt tgggaagatt tagcttctac aattaataac atgatgtatc   4200

ttgatatacc gtttattgct tttactgcaa ataacgataa ttgggtcaag caagatgaag   4260

ttatcacatt gttatcaaat attcgtagta atcgatgcaa gatatattct ttgttaggaa   4320

gttcgcatga cttgagtgaa aatttagtgg tcctgcgcaa tttttatcaa tcggttacga   4380

aagccgctat cgcgatggat aatgatcatc tggatattga tgttgatatt actgaaccgt   4440

catttgaaca tttaactatt gcgacagtca atgaacgccg aatgagaatt gagattgaaa   4500

atcaagcaat ttctctgtct taagtcgagg aggaaaacag gtatgacttc atatgttgat   4560

aaacaagaaa ttacagcaag ctcagaaatt gatgatttga ttttttcgag cgatccatta   4620

gtgtggtctt acgacgagca ggaaaaaatc agaaagaaac ttgtgcttga tgcatttcgt   4680

aatcattata aacattgtcg agaatatcgt cactactgtc aggcacacaa agtagatgac   4740

aatattacgg aaattgatga catacctgta ttcccaacat cggtttttaa gtttactcgc   4800

ttattaactt ctcaggaaaa cgagattgaa agttggttta ccagtagcgg cacgaatggt   4860

ttaaaaagtc aggtggcgcg tgacagatta agtattgaga gactcttagg ctctgtgagt   4920

tatggcatga aatatgttgg tagttggttt gatcatcaaa tagaattagt caatttggga   4980

ccagatagat ttaatgctca taatatttgg tttaaatatg ttatgagttt ggtggaattg   5040

ttatatccta cgacatttac cgtaacagaa gaacgaatag attttgttaa aacattgaat   5100

agtcttgaac gaataaaaaa tcaagggaaa gatctttgtc ttattggttc gccatacttt   5160

atttatttac tctgccatta tatgaaagat aaaaaaatct cattttctgg agataaaagc   5220

ctttatatca taaccggagg cggctggaaa agttacgaaa aagaatctct gaaacgtgat   5280

gatttcaatc atcttttatt tgatactttc aatctcagtg atattagtca gatccgagat   5340

atatttaatc aagttgaact caacacttgt ttctttgagg atgaaatgca gcgtaaacat   5400
```

-continued

```
gttccgccgt gggtatatgc gcgagcgctt gatcctgaaa cgttgaaacc tgtacctgat   5460

ggaacgccgg ggttgatgag ttatatggat gcgtcagcaa ccagttatcc agcatttatt   5520

gttaccgatg atgtcgggat aattagcaga gaatatggta agtatcccgg cgtgctcgtt   5580

gaaattttac gtcgcgtcaa tacgaggacg cagaaagggt gtgctttaag cttaaccgaa   5640

gcgtttgata gttaa                                                    5655


<210> SEQ ID NO 22
<211> LENGTH: 101
<212> TYPE: DNA
<213> ORGANISM: ESCHERICHIA COLI

<400> SEQUENCE: 22

aacgcaatta atgtgagtta gctcactcat taggcacccc aggctttaca ctttatgctt     60

ccggctcgta tgttgtgtgg aattgtgagc ggataacaat t                        101
```

METHOD FOR TRACING GRAM-NEGATIVE BACTERIA INSIDE ANIMAL MODEL USING STABLE AND BIOLUMINESCENCE-BASED EXPRESSION SYSTEM THEREFOR

"This application is a divisional application of application Ser. No. 12/895,849, filed on Oct. 1, 2010, the entire contents of which are incorporated by reference."

BACKGROUND OF THE INVENTION

1. Field of Invention

The invention relates to methods for generating bioluminescence-labeled Gram-negative bacteria in order to overcome the drawback of the difficulty to tracking the bacteria inside their hosts, because it offers a powerful tool to tracking Gram-negative bacteria in vivo using a stably and highly bioluminescence expressing plasmid vehicle.

2. Description of Related Art

For observing bacterial distribution and behavior inside the animal body, it conventionally needs the sacrifices of the experimental animals and the analyses of animal organ specimens. Therefore, an ideal method using light-emitting (bioluminescent) gene expression system of bacterial luxABCDE has been developed to observe the dynamic changes of bacterial distribution and behavior without animal sacrifice while bacteria existing inside their host bodies.

Although many methods have been previously provided to study the bacterial behavior and distribution inside their host bodies using light-emitting gene expression in bacteria, there are still certain drawbacks to limit their applications. They are as the follows: (i) the plasmids used to express the bioluminescence could not stably exist in bacteria without any selection stress, as a result of plasmid loss after couple generation; (ii) the delivery method, such as electroporation or competence, is common to transfer plasmid into bacterium, and however, it is restricted by bacterial capsule, which is composited of polysaccharides and can be a crucial barrier to limit the bacterial transformation to very low rate; (iii) the transposons utilized to insert the bioluminescence gene marker into bacterial chromosome usually transpose randomly into uncertain transposition site with unacceptably low transposition rate, and therefore the resulting individuals are different, and difficult to select and to confirm whether their insertion sites are crucial for further characteristic analysis; and (iv) the double crossing-over replacement applied to insert a marker at a specific site in chromosome needs many tedious cloning, and worse, its replacement efficiency is very poor.

Additionally, the bioluminescence genes obtained via transposition or gene replacement are just a single copy in bacterial chromosome, which might not be expressed as highly as in a high copy number of plasmid, such as the plasmid containing ColE1 replication origin. Thus, the need for improvement still exists.

SUMMARY OF THE INVENTION

It is therefore one object of the invention to provide a method for tracing Gram-negative bacteria inside animal model using stable and bioluminescence-based expression system therefor in order to directly observe and detect the dynamic change of steady bioluminescence bacteria inside animal, we built an in vivo-detectable bioluminescence plasmid in Gram-negative bacteria, which can stably exist and efficiently express luciferase genes in Gram-negative bacteria with high copy number.

By utilizing the invention the following advantages can be obtained: Ability to express the bioluminescence genes luxABCDE in Gram-negative bacteria under control by the promoter region of lacZ operon. Efficient expression of the bioluminescence gene luxABCDE contributed by high copy number of ColE1 plasmid replication origin. Steady existence of the bioluminescent luxABCDE-carried plasmid in Gram-negative bacteria due to the built-in pir, parG, parF, stbD, and stbE from the plasmid pSE34 of *Salmonella enterica* serotype *Enteritidis*. Feasible convenience to transmit the bioluminescent luxABCDE-carried plasmid among the Gram-negative bacteria by conjugation using the genes pilX1, pilX2, pilX4, pilX5, pilX6, pilX7, pilX8, pilX9, pilX10, pilX11, taxA, taxB, and taxC from the plasmid pSE34 of *Salmonella enterica* serotype *Enteritidis*.

The above and other objects, features and advantages of the invention will become apparent from the following detailed description taken with the accompanying drawings.

BRIEF DESCRIPTION OF THE DRAWINGS

FIG. 5 is a table showing plasmid stability tests of p3Zlux4 and pSE-Lux1 according to the invention.

DETAILED DESCRIPTION OF THE INVENTION

Figure 1:
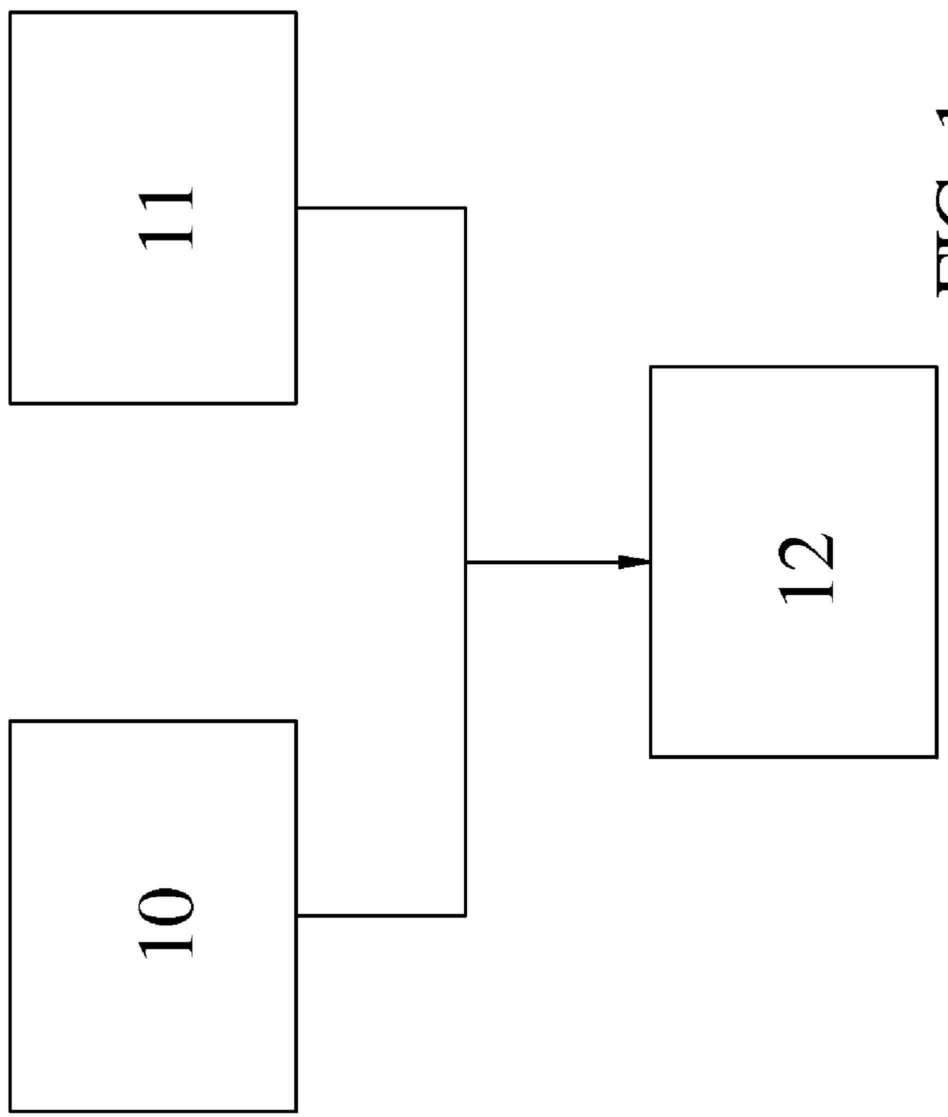
FIG. 1 is a flow chart according to the invention.
Figure 2A:
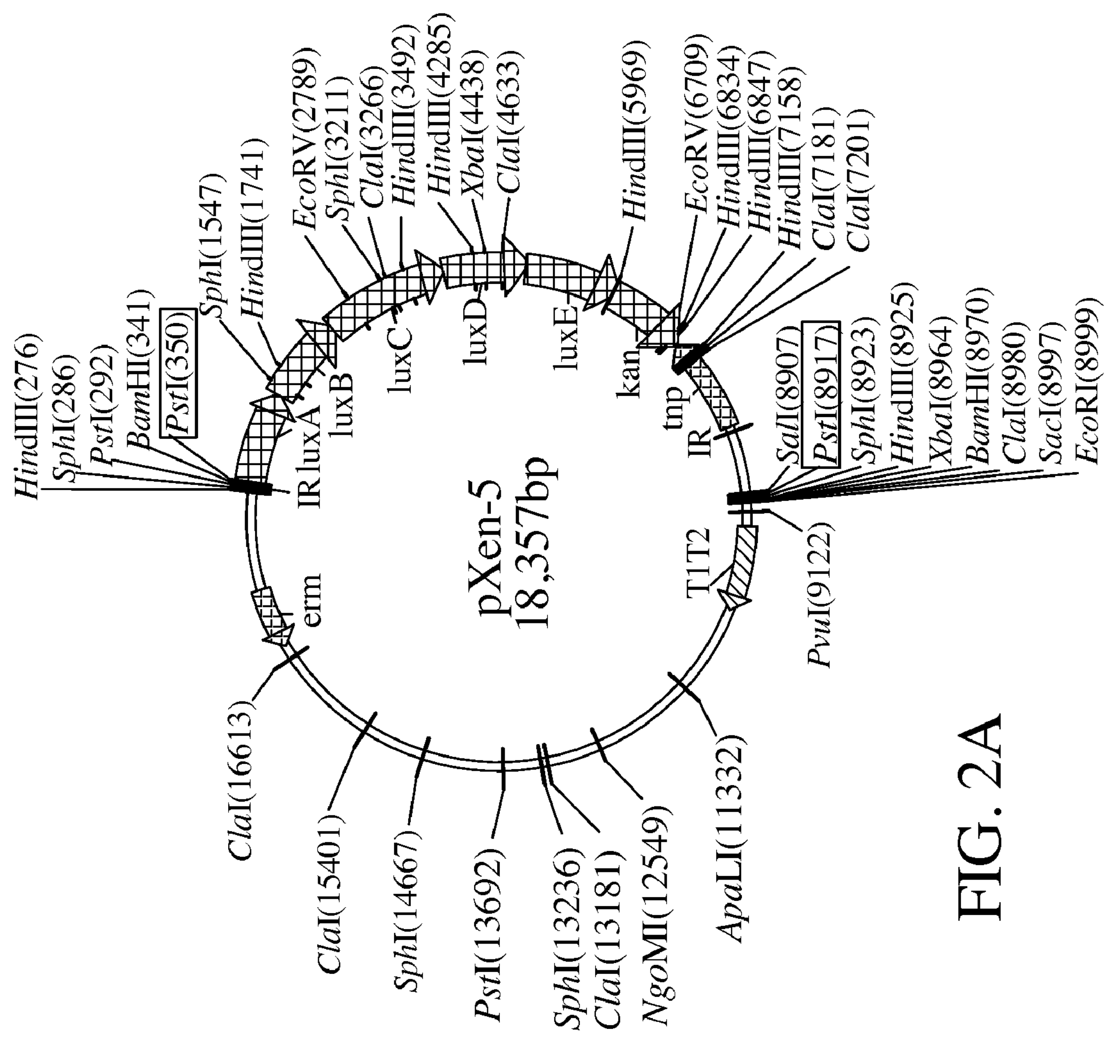
FIG. 2A schematically depicts plasmid pXen-5 of the invention.
Figure 2B:
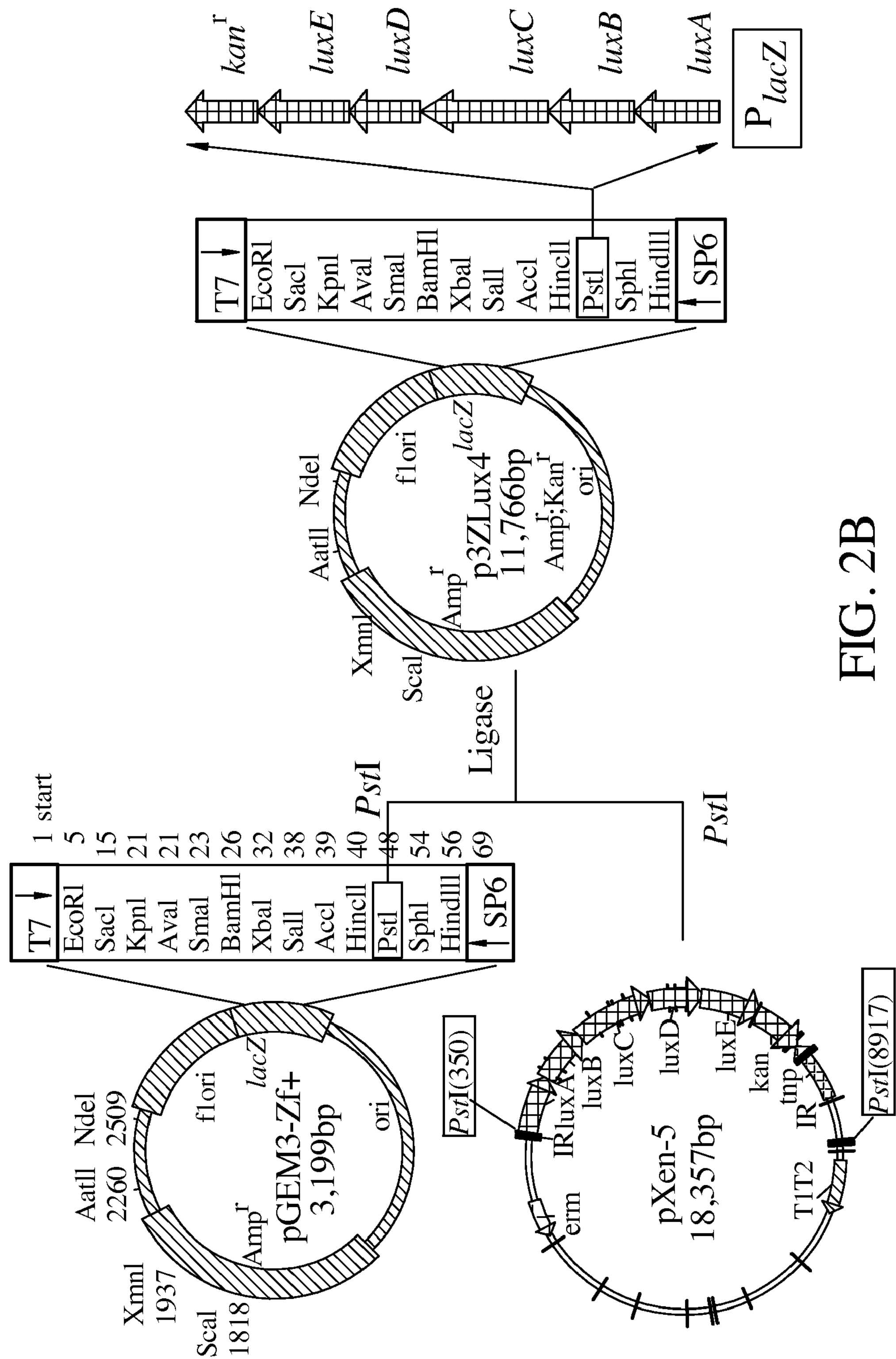
FIG. 2B schematically depicts plasmid p3ZLux4 of the invention.
Figure 3A:
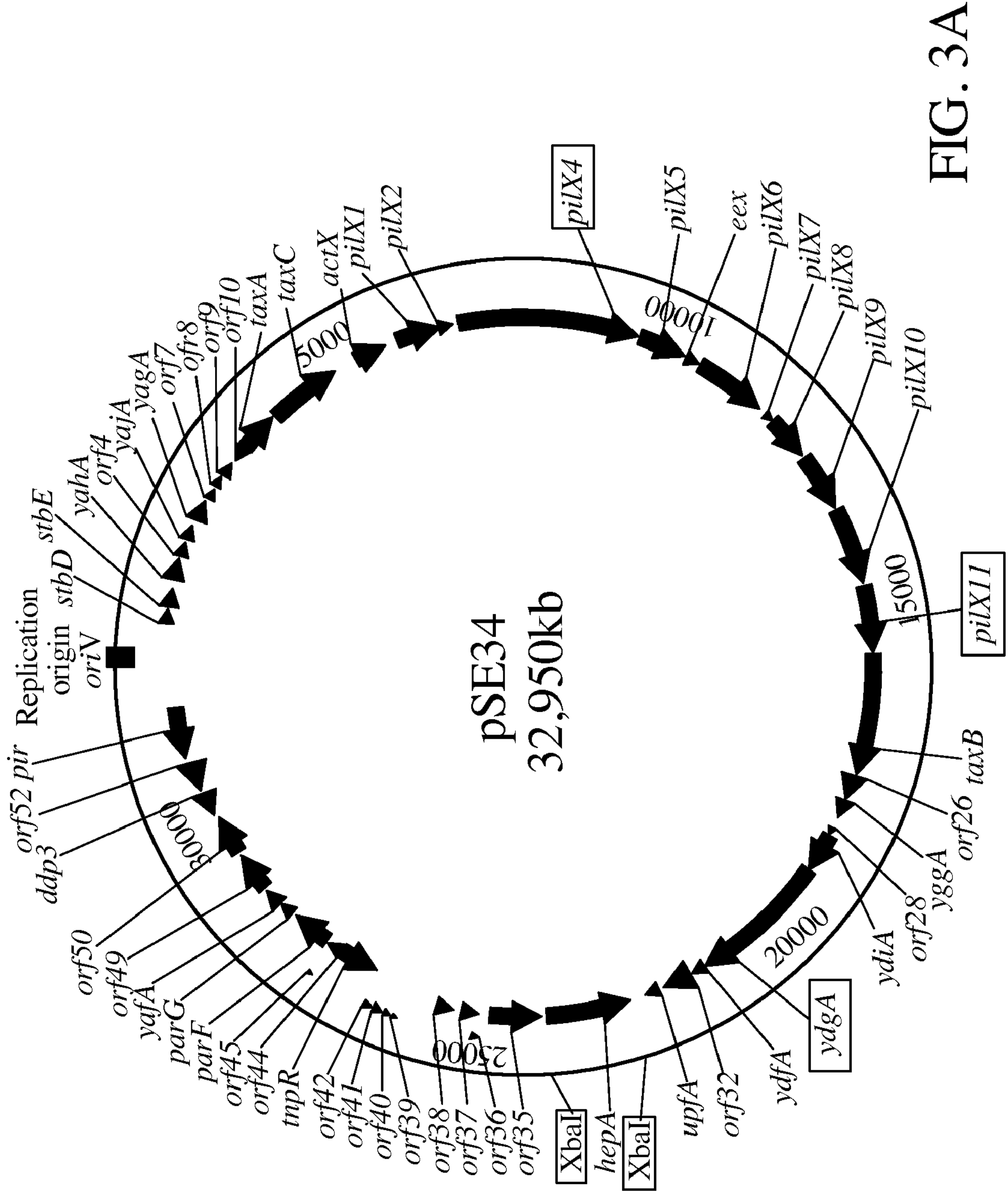
FIG. 3A schematically depicts plasmid pSE34 of the invention.
Figure 3B:
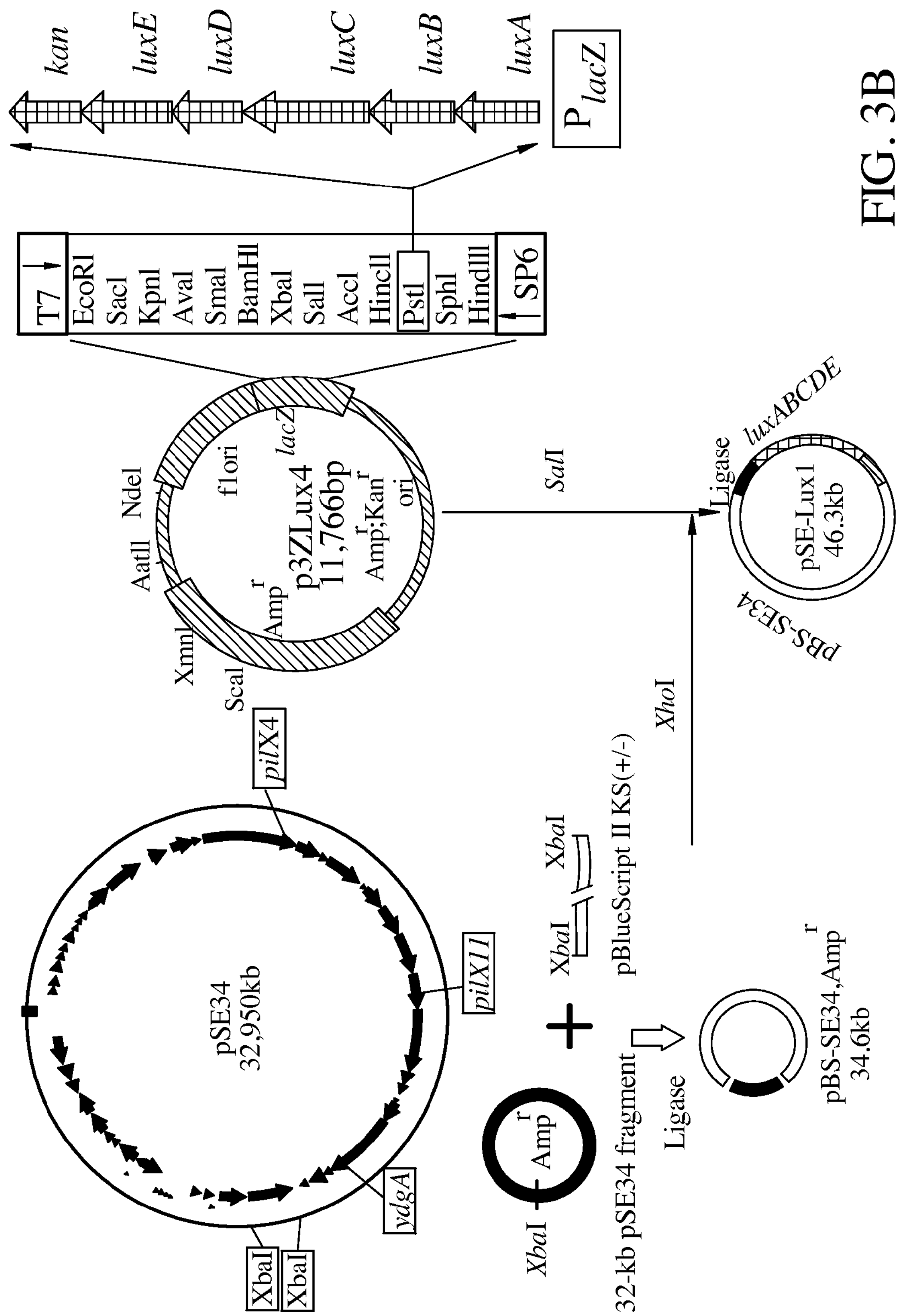
FIG. 3B schematically depicts plasmid pSE-Lux1 of the invention.

Referring to FIGS. 1 to 3B, a flow chart and plasmids in accordance with the invention are illustrated.

Steps of constructing this steady auto-bioluminescence plasmid of the invention are as the follow:

(a) To clone a promoterless luxABCDE into a promoter-containing vector, so as to express the genes luxABCDE from the promoter.

(b) To clone both at least one ColE1 replication origin and at least one drug resistance gene into a plasmid pSE34.

(c) To merge the two clones from steps (a) and (b) together, so as to obtain a vector with the features of auto-bioluminescence, plasmid stability, and high copy number.

Processes of the invention are discussed in detail below:

(a) Construction of p3ZLux4 (10)

The promoterless luxABCDE-ken from a pXen-5 was cut and inserted into a pGEM3-Zf+ using a Pstl as cloning sites based on the *Escherichia coli* cloning system, where luxABCDE genes can be expressed through the control of a lacZ promoter of pGEM3-Zf+.

Plasmid the pXen-5, is 18,357 bp long, and comprises a 5,655-bp promoterless luxABCDE and kanamycin-resistant gene ken. The luxA and luxB are luciferase-encoding genes, and luxC, luxD, and luxE encode lipid acid reductases. LuxC, LuxD, and LuxE can catalyze the reduction of long chain lipid acids, and generate aldehyde compounds, which may be the substrates for LuxA and LuxB luciferases to react and emit light.

Plasmid the pGEM3-Zf+, a 3,199-bp, comprises a ampicillin resistant gene amp, ColE1 replication origin, and a lacZ operon. The lacZ operon constitutes of a promoter, which may promote the downstream gene expression, multiple cloning site, and beta-galactosidase-encoding gene lacZ.

The resulting clone is 11,766-bp p3ZLux4, which is a high copy number, ampicillin resistant, and luxABCDE expression vector; however, it can not stably maintain inside bacteria for long time period without ampicillin selection.

(b) Construction of pBS-SE34 (11)

Plasmid pSE34 from the native *Salmonella enterica* serotype *Enteritidis* SE550 phage type PT34, 32,950 kb, was cut and inserted into a pBlueScript II KS (+/−) at XbaI site, and its insertion direction was determined by DNA sequencing. The resulting clone is named pBS-SE34.

*S. enterica* serotype *Enteritidis* SE550 phage type PT34 is the secondary dominant phage type, and its emerging is due to the presence of conjugative pSE34 (SEQ ID NO 2). This plasmid pSE34 comprises genes pir, parG, parF, stbD, and stbE, which facilitates the equal partition of plasmids into two daughter cells while bacterial cell division. Therefore, pSE34 can stably exist inside bacteria without any selection. In addition, pSE34 comprises genes pilX1, pilX2, pilX4, pilX5, pilX6, pilX7, pilX8, pilX9, pilX10, pilX11, taxA, taxB, and taxC, which may play the role of plasmid dissemination among Gram-negative bacteria through conjugation system.

Plasmid pBlueScript II KS (+/−), 2,961-bp long, comprises high copy number of ColE1 replication origin, ampicillin resistant gene, and multiple cloning sites in lacZ operon.

Therefore, the resulting clone pBS-SE34, 34.6 kb, has the features of high copy number, conjugation, and plasmid stability.

(c) Construction of pSE-Lux1 (12)

Plasmid p3ZLux4 and pBS-SE34 were cut by SalI and XhoI, respectively. The two cut DNA fragments were ligated together. The resulting clone is named pSE-Lux1, 46.3 kb. The plasmid pSE-Lux1 has the features of high copy number, high plasmid stability, auto-bioluminescence, and broad host-ranged conjugation for Gram-negative bacteria.

Figure 4:
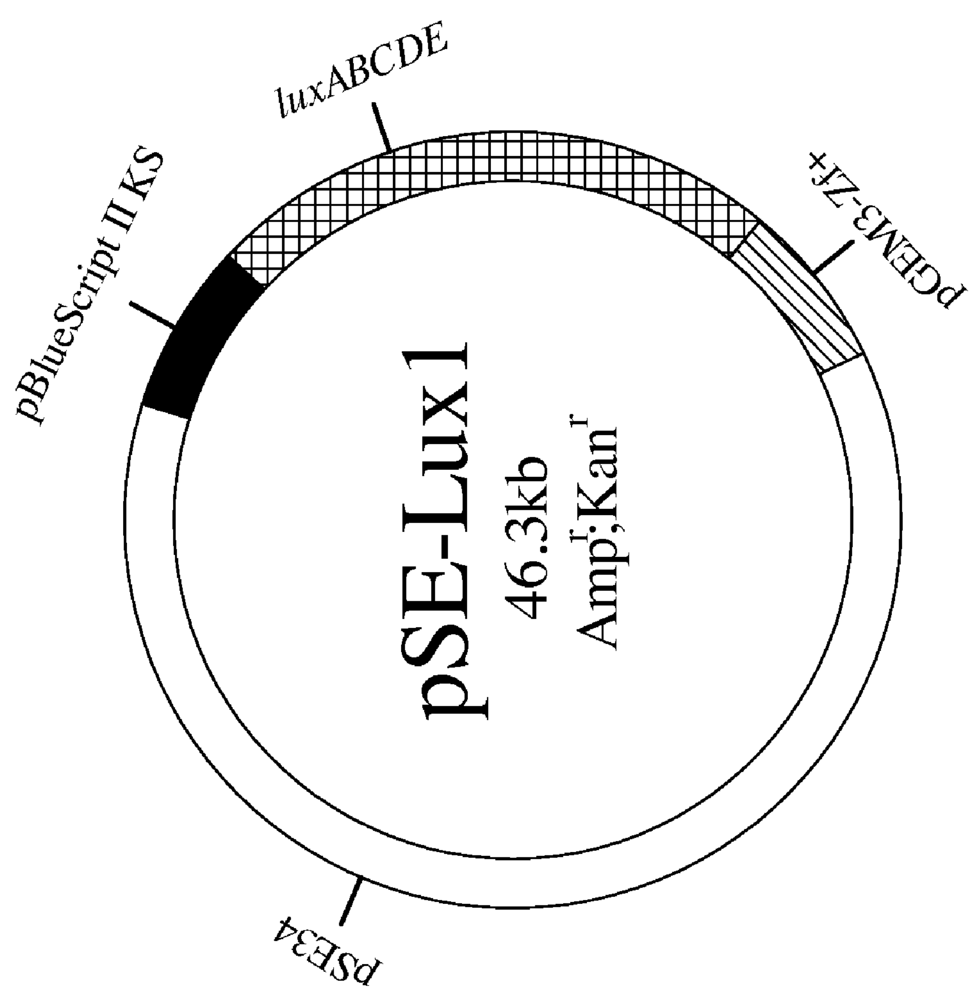
FIG. 4 schematically depicts plasmid pSE-Lux1 of the invention.

Referring to FIG. 4 in conjunction with FIGS. 1 to 3B, plasmid pSE-Lux1 of the invention is discussed in detail below. The auto-bioluminescence plasmid pSE-Lux1 (SEQ ID NO 1) of the invention specific for Gram-negative bacteria comprises at least one luxABCDE gene (SEQ ID NO 21), at least one promoter of luxABCDE gene, at least one high copy number of ColE1 replication origin, at least one drug-resistant gene, at least one gene pir (SEQ ID NO 3), at least one gene parG (SEQ ID NO 4), at least one gene parF (SEQ ID NO 5), at least one gene stbD (SEQ ID NO 6), at least one gene stbE (SEQ ID NO 7), at least one gene pilX1 (SEQ ID NO 8), at least one gene pilX2 (SEQ ID NO 9), at least one gene pilX4 (SEQ ID NO 10), at least one gene pilX5 (SEQ ID NO 11), at least one gene pilX6 (SEQ ID NO 12), at least one gene pilX7 (SEQ ID NO 13), at least one gene pilX8 (SEQ ID NO 14), at least one gene pilX9 (SEQ ID NO 15), at least one gene pilX10 (SEQ ID NO 16), at least one gene pilX11 (SEQ ID NO 17), at least one gene taxA (SEQ ID NO 18), at least one gene taxB (SEQ ID NO 19), and at least one gene taxC (SEQ ID NO 20).

Among those genes in pSE-Lux1, the promoter of luxABCDE gene is PlacZ (SEQ ID NO 22) from lacZ operon.

Among those genes in pSE-Lux1, the drug-resistant gene may be ampicillin resistant, kanamycin resistant, or ampicillin and kanamycin resistant.

Among those genes in pSE-Lux1, pir, parG, parF, stbD, and stbE genes are associated with plasmid partition, which can stabilize plasmids to be equally distributed toward two daughter cells.

Among those genes in pSE-Lux1, pilX1, pilX2, pilX4, pilX5, pilX6, pilX7, pilX8, pilX9, pilX10, pilX11, taxA, taxB, and taxC are associated with plasmid conjugation, and they may facilitate for the gene cloning and plasmid transmission from one bacterium to another, such as to deliver a conjugative plasmid from *Salmonella enterica* to *Escherichia coli*.

Among those genes in pSE-Lux1, the luxABCDE comprises luxA, luxB, luxC, luxD, and luxE. Genes luxA and luxB are luciferase-encoding genes, and luxC, luxD, and luxE encode lipid acid reductases. LuxC, LuxD, and LuxE can catalyze the reduction of long chain lipid acids, and their products are aldehyde compounds.

The aldehydes are the substrates for LuxA and LuxB luciferases to react and emit light. Therefore, it is no need to add any substrate for luciferases to emit light.

Because the pSE-Lux1 in the invention can not only independently assist bacteria to appear bioluminescent, but also steady exist inside bacteria, the advantage of the invention is good for direct observation and detection of the dynamic changes while the bioluminescence bacteria existing inside animals.

Referring to FIG. 5, a plasmid stability test according to the invention is discussed in detailed below.

Two clones with p3Zlux4 and pSE-Lux1 in *E. coli* and *S. enterica Typhimurium* LBNP4471, respectively, were continuously cultured in LB (Luria-Bertani) broth without any supplementation, such as antibiotics. After 79 generation, they were plated onto both LB agar and LB agar with the supplementation of ampicillin and kanamycin in order to count the bacterial cell counts (colony formation units, CFU). The results as shown in FIG. 5 show that there were 76.3% (1550/2030) colonies remaining the resistance to ampicillin and kanamycin in the case of pSE-Lux1, whereas only 8.8×10-4% in the case of p3Zlux4. It means that pSE-Lux1 has much better stability than p3ZLux4 as high as around hundred thousand folds. In addition, all of colonies from the LB agar with the supplementation of ampicillin and kanamycin can appear bioluminescence, indicating that plasmid pSE-Lux1 can stably exit in Gram-negative bacteria and efficient express the bioluminescence gene luxABCDE.

While the invention has been described in terms of preferred embodiments, those skilled in the art will recognize that the invention can be practiced with modifications within the spirit and scope of the appended claims.

What is claimed is:

1. A method of creating a steady bioluminescence vector which has DNA sequences listed in SEQ ID NO 1 and used for Gram-negative bacteria comprising steps of:

(a) cloning a promoterless luxABCDE that comes from a vector pXen-5 into a promoter-containing vector to express the genes luxABCDE, wherein the gene expression of luxABCDE is controlled through a lacZ promotor of a plasmid pGEM3-Zf+;

(b) cloning a conjugative plasmid pSE34 with a plasmid pBlueScript II KS (+/−) that has at least one ColE1 replication origin and at least one drug resistance gene; and (c) ligating said merging the two clones from steps (a) and (b) together so as to obtain the bioluminescence vector which has the DNA sequence listed in SEQ ID NO:1 with the features of auto-bioluminescence, plasmid stability, conjugation and a high copy number.

* * * * *